(12) United States Patent
Ren et al.

(10) Patent No.: US 12,122,392 B2
(45) Date of Patent: Oct. 22, 2024

(54) CONTEXT-BASED STATE ESTIMATION

(71) Applicant: Nvidia Corporation, Santa Clara, CA (US)

(72) Inventors: Yuzhuo Ren, Sunnyvale, CA (US); Niranjan Avadhanam, Saratoga, CA (US)

(73) Assignee: Nvidia Corporation, Santa Clara, CA (US)

( * ) Notice: Subject to any disclaimer, the term of this patent is extended or adjusted under 35 U.S.C. 154(b) by 40 days.

(21) Appl. No.: 17/410,580

(22) Filed: Aug. 24, 2021

(65) Prior Publication Data
US 2023/0065399 A1 Mar. 2, 2023

(51) Int. Cl.
*B60W 40/09* (2012.01)
*G06V 20/59* (2022.01)
*G06V 40/16* (2022.01)

(52) U.S. Cl.
CPC ............ *B60W 40/09* (2013.01); *G06V 20/597* (2022.01); *B60W 2420/403* (2013.01); *B60W 2540/229* (2020.02); *B60W 2554/4046* (2020.02); *B60W 2554/4049* (2020.02); *G06V 40/161* (2022.01); *G06V 40/171* (2022.01); *G06V 40/172* (2022.01)

(58) Field of Classification Search
CPC ............ B60W 40/09; B60W 2420/42; B60W 2540/229; B60W 2554/4046; B60W 2554/4049; G06V 20/597; G06V 40/161; G06V 40/171; G06V 40/172
See application file for complete search history.

(56) References Cited

U.S. PATENT DOCUMENTS

| | | | |
|---|---|---|---|
| 6,496,724 B1 | 12/2002 | Levendowski et al. | |
| 9,545,224 B2 | 1/2017 | Johns et al. | |
| 11,386,679 B2 | 7/2022 | Qin et al. | |
| 2002/0105427 A1 | 8/2002 | Hamamoto et al. | |
| 2004/0233061 A1* | 11/2004 | Johns | A61B 3/113 340/575 |
| 2008/0101659 A1* | 5/2008 | Hammoud | G08B 21/06 382/104 |
| 2014/0172467 A1 | 6/2014 | He et al. | |

(Continued)

OTHER PUBLICATIONS https://www.marketscreener.com/news/latest/Affectiva-nbsp-Awarded-Six-Patents-for-Multi-Modal-Human-Perception-AI-and-Advanced-In-Cabin-Sensi--32764008/.

(Continued)

*Primary Examiner* — Wesley J Tucker
(74) *Attorney, Agent, or Firm* — Hogan Lovells US LLP

(57) ABSTRACT

State information can be determined for a subject that is robust to different inputs or conditions. For drowsiness, facial landmarks can be determined from captured image data and used to determine a set of blink parameters. These parameters can be used, such as with a temporal network, to estimate a state (e.g., drowsiness) of the subject. To improve robustness, an eye state determination network can determine eye state from the image data, without reliance on intermediate landmarks, that can be used, such as with another temporal network, to estimate the state of the subject. A weighted combination of these values can be used to determine an overall state of the subject. To improve accuracy, individual behavior patterns and context information can be utilized to account for variations in the data due to subject variation or current context rather than changes in state.

20 Claims, 22 Drawing Sheets

(56) References Cited

U.S. PATENT DOCUMENTS

| | | |
|---|---|---|
| 2014/0204193 A1 | 7/2014 | Zhang et al. |
| 2014/0205149 A1 | 7/2014 | Nakamura et al. |
| 2015/0314681 A1 | 11/2015 | Riley, Sr. et al. |
| 2017/0220109 A1 | 8/2017 | Liu |
| 2017/0351812 A1 | 12/2017 | Green et al. |
| 2018/0232588 A1* | 8/2018 | Matsumura ........... G06V 20/597 |
| 2019/0300034 A1* | 10/2019 | Molne .................... B61L 25/021 |
| 2020/0151474 A1* | 5/2020 | Zandi ....................... G06F 3/013 |
| 2021/0004618 A1 | 1/2021 | Qin et al. |
| 2021/0004619 A1 | 1/2021 | Qin et al. |
| 2021/0188291 A1 | 6/2021 | el Kaliouby et al. |
| 2021/0380115 A1* | 12/2021 | Alpert ....................... G06N 3/08 |
| 2022/0095975 A1* | 3/2022 | Aluf ................... B60W 60/0051 |
| 2022/0121867 A1 | 4/2022 | Arar et al. |
| 2022/0215200 A1* | 7/2022 | Alpert .................. G06V 20/597 |
| 2022/0230522 A1* | 7/2022 | Myers .................. G06V 10/141 |
| 2022/0366568 A1 | 11/2022 | Arar et al. |
| 2023/0056399 A1* | 2/2023 | Ji ........................... H04W 72/20 |
| 2023/0065399 A1 | 3/2023 | Ren et al. |
| 2023/0065491 A1 | 3/2023 | Ren et al. |
| 2023/0260301 A1 | 8/2023 | Hassani et al. |
| 2023/0351807 A1 | 11/2023 | Ren et al. |
| 2024/0023884 A1 | 1/2024 | Liu et al. |

OTHER PUBLICATIONS

Non-Final Office Action issued in U.S. Appl. No. 17/410,564, dated Mar. 20, 2023.

Notice of Allowance issued in U.S. Appl. No. 17/410,564, dated Jul. 11, 2023.

Non-Final Office Action issued in U.S. Appl. No. 18/516,531, mailed Jun. 17, 2024.

\* cited by examiner

CONTEXT-BASED STATE ESTIMATION

BACKGROUND

There is an ever-present desire to improve safety in various environments. This can include, for example, accurately determining the drowsiness of a person who might be operating a device, such as a vehicle or piece of machinery, that might result in damage or injury if not operated with sufficient attention or awareness. While systems exist to attempt to determine states such as drowsiness or alertness, these systems are not accurate in all situations or sufficiently robust to variations between users, user states, or environmental conditions.

BRIEF DESCRIPTION OF THE DRAWINGS

Various embodiments in accordance with the present disclosure will be described with reference to the drawings, in which.

DETAILED DESCRIPTION

Approaches in accordance with various embodiments can provide for determinations of the state of a person or other such subject. In particular, various embodiments provide for determination of a drowsiness, fatigue, or alertness state of a person based, at least in part, upon an observed blink behavior of a person over time. An end-to-end drowsiness estimation system can be utilized that includes multiple neural networks, and can therefore be relatively robust to changes in input data. One of these neural networks can be used to determine a set of facial landmarks in captured image data, which can be used to determine a set of blink parameters for a subject over a period of time. This set of blink parameters can be used, such as with a temporal network, to infer a state value for the subject, such as a drowsiness level for a person of interest represented in the captured image data. A separate neural network can determine eye state (e.g., open or closed) from the captured image data, without relying on an accuracy of the intermediate facial landmarks, which can improve a robustness of the overall process. The eye state information can be used, such as with another temporal network, to infer another state value for the subject. The state values from these temporal networks can then be used, such as through a weighted combination if each is inferred with at least minimum confidence, to determine an overall state value estimate for the person. This state value can be used to determine whether or not to take an action based on the state of the person, as well as to determine which type of action to take. In order to improve the accuracy of such an estimate, a system can also attempt to account for variations in behavior between individual subjects, as well as variations due to changes in a current context or environment, such as changes in driving context. Subject and/or context data can be provided as input to a temporal network, for example, such that the network can infer more accurate state data by comparing the blink parameters, or other observed behavior data, against baselines that are more relevant for the specific subject under the current context.

Figure 1A:
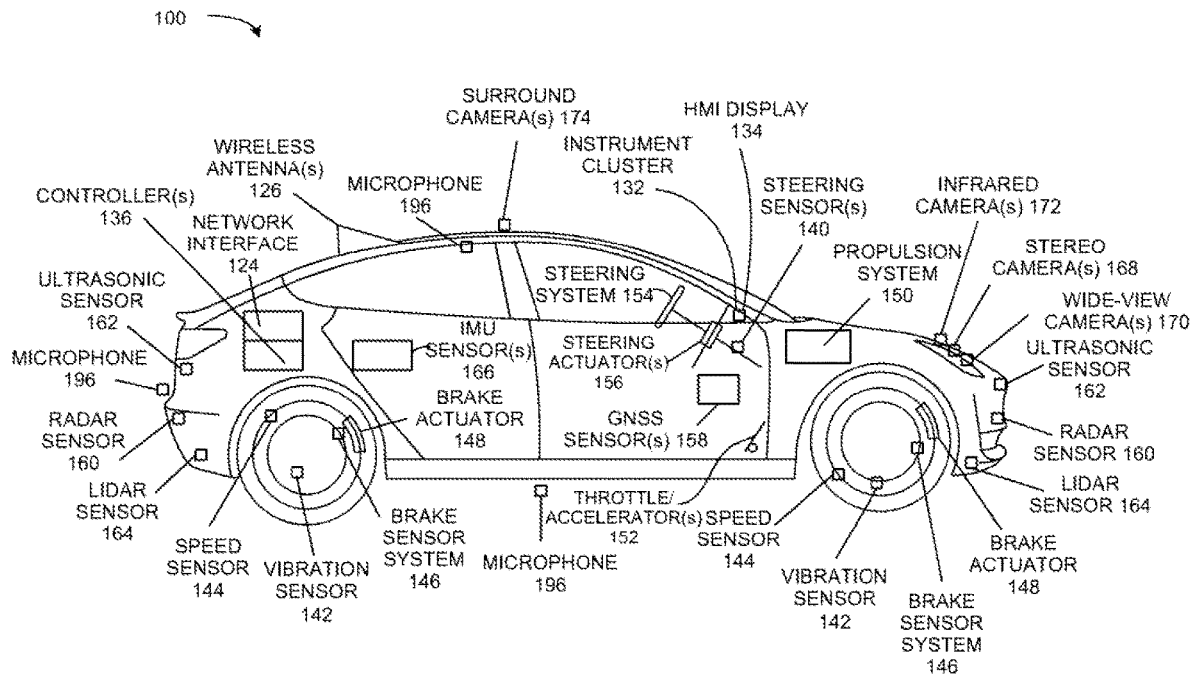
FIGS. 1A and 1B illustrate examples of components of a vehicle, according to at least one embodiment.

Consider a vehicle 100 illustrated in FIG. 1A, such as a semi-autonomous or computer-assisted vehicle that may include one or more drivers or passengers. In at least one embodiment, vehicle 100 may be, without limitation, a passenger vehicle, such as a car, a truck, a bus, and/or another type of vehicle that accommodates one or more passengers. In at least one embodiment, vehicle 100 may be a semi-tractor-trailer truck used for hauling cargo. In at least one embodiment, vehicle 100 may be an airplane, robotic vehicle, or other kind of vehicle.

Autonomous vehicles may be described in terms of automation levels, defined by National Highway Traffic Safety Administration ("NHTSA"), a division of US Department of Transportation, and Society of Automotive Engineers ("SAE") "Taxonomy and Definitions for Terms Related to Driving Automation Systems for On-Road Motor Vehicles" (e.g., Standard No. J3016-201806, published on Jun. 15, 2018, Standard No. J3016-201609, published on Sep. 30, 2016, and previous and future versions of this standard). In one or more embodiments, vehicle 100 may be capable of functionality in accordance with one or more of level 1-level 5 of autonomous driving levels. For example, in at least one embodiment, vehicle 100 may be capable of conditional automation (Level 3), high automation (Level 4), and/or full automation (Level 5), depending on embodiment.

In at least one embodiment, vehicle 100 may include, without limitation, components such as a chassis, a vehicle body, wheels (e.g., 2, 4, 6, 8, 18, etc.), tires, axles, and other components of a vehicle. In at least one embodiment, vehicle 100 may include, without limitation, a propulsion system 150, such as an internal combustion engine, hybrid electric power plant, an all-electric engine, and/or another propulsion system type. In at least one embodiment, propulsion system 150 may be connected to a drive train of vehicle 100, which may include, without limitation, a transmission, to enable propulsion of vehicle 100. In at least one embodiment, propulsion system 150 may be controlled in response to receiving signals from a throttle/accelerator(s) 152.

In at least one embodiment, a steering system 154, which may include, without limitation, a steering wheel, is used to steer a vehicle 100 (e.g., along a desired path or route) when a propulsion system 150 is operating (e.g., when vehicle is in motion). In at least one embodiment, a steering system 154 may receive signals from steering actuator(s) 156. A steering wheel may be optional for full automation (Level 5) functionality. In at least one embodiment, a brake sensor system 146 may be used to operate vehicle brakes in response to receiving signals from brake actuator(s) 148 and/or brake sensors.

In at least one embodiment, controller(s) 136, which may include, without limitation, one or more system on chips ("SoCs") (not shown in FIG. 1A) and/or graphics processing unit(s) ("GPU(s)"), provide signals (e.g., representative of commands) to one or more components and/or systems of vehicle 100. For instance, in at least one embodiment, controller(s) 136 may send signals to operate vehicle brakes via brake actuator(s) 148, to operate steering system 154 via steering actuator(s) 156, and/or to operate propulsion system 150 via throttle/accelerator(s) 152. Controller(s) 136 may include one or more onboard (e.g., integrated) computing devices (e.g., supercomputers) that process sensor signals, and output operation commands (e.g., signals representing commands) to enable autonomous driving and/or to assist a human driver in driving vehicle 100. In at least one embodiment, controller(s) 136 may include a first controller 136 for autonomous driving functions, a second controller 136 for functional safety functions, a third controller 136 for artificial intelligence functionality (e.g., computer vision), a fourth controller 136 for infotainment functionality, a fifth controller 136 for redundancy in emergency conditions, and/or other controllers. In at least one embodiment, a single controller 136 may handle two or more of above functionalities, two or more controllers 136 may handle a single functionality, and/or any combination thereof.

In at least one embodiment, controller(s) 136 provide signals for controlling one or more components and/or systems of vehicle 100 in response to sensor data received from one or more sensors (e.g., sensor inputs). In at least one embodiment, sensor data may be received from, for example and without limitation, global navigation satellite systems ("GNSS") sensor(s) 158 (e.g., Global Positioning System sensor(s)), RADAR sensor(s) 160, ultrasonic sensor(s) 162, LIDAR sensor(s) 164, inertial measurement unit ("IMU") sensor(s) 166 (e.g., accelerometer(s), gyroscope(s), magnetic compass(es), magnetometer(s), etc.), microphone(s) 196, stereo camera(s) 168, wide-view camera(s) 170 (e.g., fisheye cameras), infrared camera(s) 172, surround camera(s) 174 (e.g., 360 degree cameras), long-range cameras (not shown in FIG. 1A), mid-range camera(s) (not shown in FIG. 1A), speed sensor(s) 144 (e.g., for measuring speed of vehicle 100), vibration sensor(s) 142, steering sensor(s) 140, brake sensor(s) (e.g., as part of brake sensor system 146), and/or other sensor types.

In at least one embodiment, one or more of controller(s) 136 may receive inputs (e.g., represented by input data) from an instrument cluster 132 of vehicle 100 and provide outputs (e.g., represented by output data, display data, etc.) via a human-machine interface ("HMI") display 134, an audible annunciator, a loudspeaker, and/or via other components of vehicle 100. In at least one embodiment, outputs may include information such as vehicle velocity, speed, time, map data (e.g., a High Definition map (not shown in FIG. 1A), location data (e.g., vehicle 100's location, such as on a map), direction, location of other vehicles (e.g., an occupancy grid), information about objects and status of objects as perceived by controller(s) 136, etc. For example, in at least one embodiment, HMI display 134 may display information about presence of one or more objects (e.g., a street sign, caution sign, traffic light changing, etc.), and/or information about driving maneuvers vehicle has made, is making, or will make (e.g., changing lanes now, taking exit 34B in two miles, etc.).

In at least one embodiment, vehicle 100 further includes a network interface 124 which may use wireless antenna(s) 126 and/or modem(s) to communicate over one or more networks. For example, in at least one embodiment, network interface 124 may be capable of communication over Long-Term Evolution ("LTE"), Wideband Code Division Multiple Access ("WCDMA"), Universal Mobile Telecommunications System ("UMTS"), Global System for Mobile communication ("GSM"), IMT-CDMA Multi-Carrier ("CDMA2000"), etc. In at least one embodiment, wireless antenna(s) 126 may also enable communication between objects in environment (e.g., vehicles, mobile devices, etc.), using local area network(s), such as Bluetooth, Bluetooth Low Energy ("LE"), Z-Wave, ZigBee, etc., and/or low power wide-area network(s) ("LPWANs"), such as LoRaWAN, SigFox, etc.

Figure 1B:
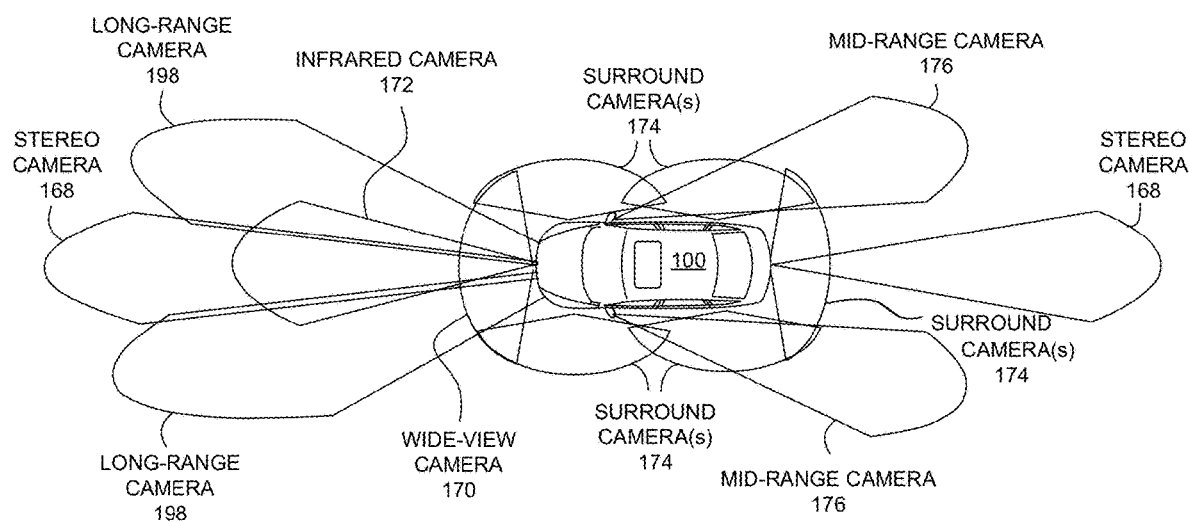

FIG. 1B illustrates an example of camera locations and fields of view for autonomous vehicle 100 of FIG. 1A, according to at least one embodiment. In at least one embodiment, cameras and respective fields of view are one example embodiment and are not intended to be limiting. For instance, in at least one embodiment, additional and/or alternative cameras may be included and/or cameras may be located at different locations on vehicle 100.

In at least one embodiment, camera types for cameras may include, but are not limited to, digital cameras that may be adapted for use with components and/or systems of vehicle 100. In at least one embodiment, one or more of camera(s) may operate at automotive safety integrity level ("ASIL") B and/or at another ASIL. In at least one embodiment, camera types may be capable of any image capture rate, such as 60 frames per second (fps), 120 fps, 240 fps, etc., depending on embodiment. In at least one embodiment, cameras may be capable of using rolling shutters, global shutters, another type of shutter, or a combination thereof. In at least one embodiment, color filter array may include a red clear clear clear ("RCCC") color filter array, a red clear clear blue ("RCCB") color filter array, a red blue green clear ("RBGC") color filter array, a Foveon X3 color filter array, a Bayer sensors ("RGGB") color filter array, a monochrome sensor color filter array, and/or another type of color filter array. In at least one embodiment, clear pixel cameras, such as cameras with an RCCC, an RCCB, and/or an RBGC color filter array, may be used in an effort to increase light sensitivity.

In at least one embodiment, one or more of camera(s) may be used to perform advanced driver assistance systems ("ADAS") functions (e.g., as part of a redundant or fail-safe design). For example, in at least one embodiment, a Multi-Function Mono Camera may be installed to provide functions including lane departure warning, traffic sign assist and intelligent headlamp control. In at least one embodiment, one or more of camera(s) (e.g., all of cameras) may record and provide image data (e.g., video) simultaneously.

In at least one embodiment, one or more of cameras may be mounted in a mounting assembly, such as a custom designed (three-dimensional ("3D") printed) assembly, in order to cut out stray light and reflections from within car (e.g., reflections from dashboard reflected in windshield mirrors) which may interfere with camera's image data capture abilities. With reference to wing-mirror mounting assemblies, in at least one embodiment, wing-mirror assemblies may be custom 3D printed so that camera mounting plate matches shape of wing-mirror. In at least one embodiment, camera(s) may be integrated into wing-mirror. For side-view cameras, camera(s) may also be integrated within four pillars at each corner in at least one embodiment.

In at least one embodiment, cameras with a field of view that include portions of environment in front of vehicle 100 (e.g., front-facing cameras) may be used for surround view, to help identify forward facing paths and obstacles, as well as aid in, with help of one or more of controllers 136 and/or control SoCs, providing information critical to generating an occupancy grid and/or determining preferred vehicle paths. In at least one embodiment, front-facing cameras may be used to perform many of same ADAS functions as LIDAR, including, without limitation, emergency braking, pedestrian detection, and collision avoidance. In at least one embodiment, front-facing cameras may also be used for ADAS functions and systems including, without limitation, Lane Departure Warnings ("LDW"), Autonomous Cruise Control ("ACC"), and/or other functions such as traffic sign recognition.

In at least one embodiment, a variety of cameras may be used in a front-facing configuration, including, for example, a monocular camera platform that includes a CMOS ("complementary metal oxide semiconductor") color imager. In at least one embodiment, wide-view camera 170 may be used to perceive objects coming into view from periphery (e.g., pedestrians, crossing traffic or bicycles). Although only one wide-view camera 170 is illustrated in FIG. 1B, in other embodiments, there may be any number (including zero) of wide-view camera(s) 170 on vehicle 100. In at least one embodiment, any number of long-range camera(s) 198 (e.g., a long-view stereo camera pair) may be used for depth-based object detection, especially for objects for which a neural network has not yet been trained. In at least one embodiment, long-range camera(s) 198 may also be used for object detection and classification, as well as basic object tracking.

In at least one embodiment, any number of stereo camera(s) 168 may also be included in a front-facing configuration. In at least one embodiment, one or more of stereo camera(s) 168 may include an integrated control unit comprising a scalable processing unit, which may provide a programmable logic ("FPGA") and a multi-core microprocessor with an integrated Controller Area Network ("CAN") or Ethernet interface on a single chip. In at least one embodiment, such a unit may be used to generate a 3D map of environment of vehicle 100, including a distance estimate for all points in image. In at least one embodiment, one or more of stereo camera(s) 168 may include, without limitation, compact stereo vision sensor(s) that may include, without limitation, two camera lenses (one each on left and right) and an image processing chip that may measure distance from vehicle 100 to target object and use generated information (e.g., metadata) to activate autonomous emergency braking and lane departure warning functions. In at least one embodiment, other types of stereo camera(s) 168 may be used in addition to, or alternatively from, those described herein.

In at least one embodiment, cameras with a field of view that include portions of environment to side of vehicle 100 (e.g., side-view cameras) may be used for surround view, providing information used to create and update occupancy grid, as well as to generate side impact collision warnings. For example, in at least one embodiment, surround camera(s) 174 (e.g., four surround cameras 174 as illustrated in FIG. 1B) could be positioned on vehicle 100. In at least one embodiment, surround camera(s) 174 may include, without limitation, any number and combination of wide-view camera(s) 170, fisheye camera(s), 360 degree camera(s), and/or like. For instance, in at least one embodiment, four fisheye cameras may be positioned on front, rear, and sides of vehicle 100. In at least one embodiment, vehicle 100 may use three surround camera(s) 174 (e.g., left, right, and rear), and may leverage one or more other camera(s) (e.g., a forward-facing camera) as a fourth surround-view camera.

In at least one embodiment, cameras with a field of view that include portions of environment to rear of vehicle 100 (e.g., rear-view cameras) may be used for park assistance, surround view, rear collision warnings, and creating and updating occupancy grid. In at least one embodiment, a wide variety of cameras may be used including, but not limited to, cameras that are also suitable as a front-facing camera(s) (e.g., long-range cameras 198 and/or mid-range camera(s) 176, stereo camera(s) 168), infrared camera(s) 172, etc.), as described herein.

In various situations, it may be desirable to determine a state of a person in, or associated with, such a vehicle. This may include, for example, determining a state of drowsiness or alertness of a driver of this vehicle. An approach in accordance with various embodiments can take advantage of one or more cameras or imaging sensors, such as those discussed previously for such a vehicle, that can capture image or video data of at least a portion of a person of interest. This can include, for example a driver-facing camera that is able to capture at least a face of a driver or other person sitting in a driver seat, or other position associated with at least some amount of vehicle control. Such a camera may be positioned at any appropriate location, such as on or proximate an instrument cluster, rear view mirror, left pillar, or touch interface, among other such options. Such a camera may be a full color or grayscale camera of any appropriate resolution, and may include infrared (IR) or other sensors as well in various embodiments.

In at least one embodiment, video or images of such a person may be captured at specific times, periodically, or continuously. If captured at specific times, these times may be determined according to a selection algorithm, or may be determined based at least in part upon one or more triggers, such as a signal from a vehicle system sent in response to an action or behavior that may be associated with driver drowsiness. In other embodiments, a trigger may be sent in response to a change in an environment, such as moving into a crowded urban area where more attention may be required, or passing into an evening or nighttime when a driver may be more likely to be drowsy. Such timing may also be user, application, or device configurable.

In at least one embodiment, a series of images or sequence (e.g., stream) of video frames can be captured using one or more cameras. Under typical circumstances, these images or video frames will include a representation of at least a face portion of a person of interest, such as illustrated in the image 200 of FIG. 2A. Depending upon factors such as a location and field of view of the camera relative to the person, the captured image may represent predominantly the face region of the person, or may include a larger view that may include portions of the torso, arms, and so on. In at least one embodiment, such an image may be passed to a face detection network, or other face detector, that can attempt to determine whether a face of a person is present in this image. A face may not be represented if, for example, the person is not currently positioned in that location, is turned away from the camera, or is otherwise in a position such that a sufficient portion of that person's face is not represented in the image to enable a confident face detection. It might also be the case where there is some obstruction blocking a view of the face, such as an arm or hand positioned between the camera and the face during operation of the vehicle.

If a face is detected in an image (or video frame, etc.), then that image may be selected for analysis. For simplicity of explanation, the term "image" or "image data" will be used in many examples, but it should be understood that this may also refer to video frames, video data, sensor data, or any other type of data in any format that can capture or represent information for one or more visual aspects of a person. Not every captured image may be analyzed, such as where a system might analyze every tenth image if the person is in a normal or alert state, but may analyze images more frequently if the person is in a less alert or drowsy state. Images might also be analyzed more frequently for certain environmental conditions or driving context as discussed in more detail elsewhere herein. In at least one embodiment, data corresponding to the face region of an image may be used to select a portion of the image to be analyzed, in order to reduce an amount of memory and processing capacity needed, as well as to focus on a more relevant portion of the image, which can help improve accuracy of inferences or determinations for at least some systems.

Figure 2A:
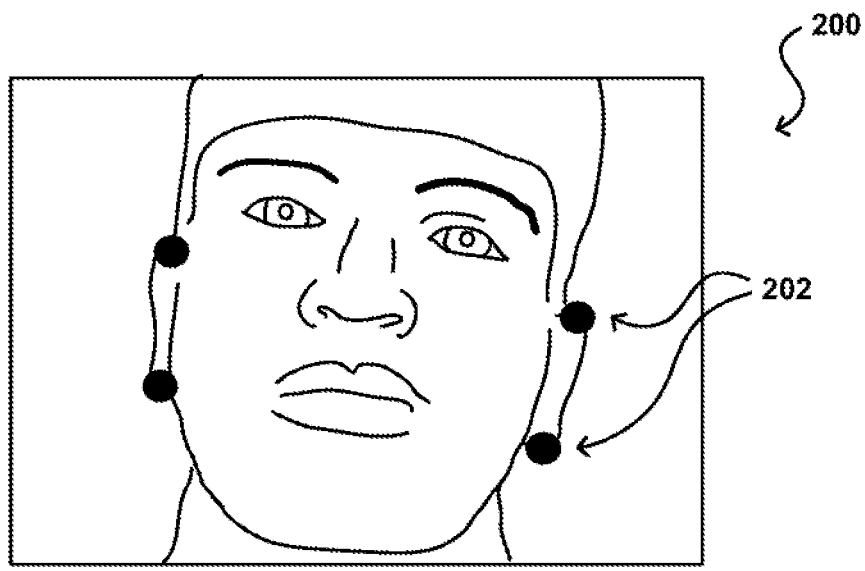
FIGS. 2A, 2B, 2C, 2D, 2E, and 2F illustrate feature data that can be utilized, according to at least one embodiment.
Figure 2B:
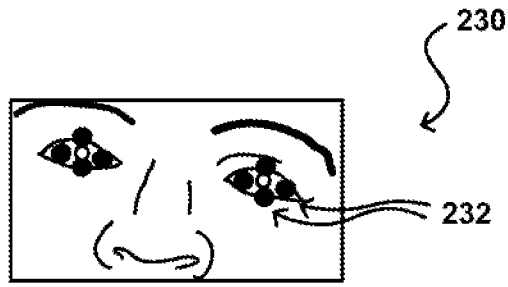
Figure 2C:
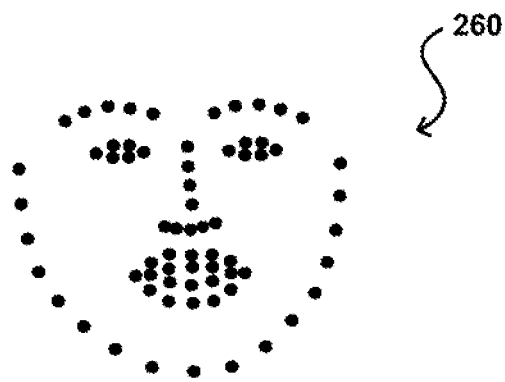

For an image to be analyzed, at least a face portion of that image can be processed using a first neural network, such as a facial landmark detection network. The face portion may be identified by coordinates or a bounding box provided by the face detection network. Other feature detection mechanisms can be used as well within the scope of the various embodiments. A facial landmark detection network can be trained to infer the locations of specific types of landmarks, fiducial points, or features in an image. This may include identifying any of 100 different features or more, for example, that are represented or detectable in an input image. As illustrated in FIG. 2A, this may include identifying landmarks 202 such as the tops and bottoms of the ears of the person. Such landmarks can be useful at least for the fact that they can help to determine a pose or orientation of the head with respect to the camera capturing the image. Other landmarks 232 can be useful as well, such as those illustrated in the image region 230 of FIG. 2B. These landmarks correspond to extrema (here top, bottom, left, and right) of each iris of a person, which can then be used to determine information such as an amount to which this person has opened his or her eye. Changes in the relative positions of these landmarks 232 between successive frames can be used to detect blinks, as well as to determine values such as the amplitude, velocity, or duration of an individual blink. In at least one embodiment, information for any detected landmarks can be output by a facial landmark detection network, such as may include coordinates of a given landmark in the image, as well as an identification of the type of landmark identified.

Data for at least some of these features or landmarks can also be provided as input to other neural networks, algorithms, or modules for determining other aspects or behaviors. For example, facial landmarks related to the eyes of a person may be provided to an eye state determination neural network, along with at least a face portion of an input image, to determine a region of the input image that corresponds to the eyes of a person. In other embodiments, some of the facial landmarks can be used to crop the input image to only the eye region(s) and this cropped image data can be provided as input to the eye state network. This enables the eye state neural network to focus on that portion of the input image that corresponds to the eyes, in order to provide for more accurate inferences as to eye state and to simplify a corresponding network training process. In at least one embodiment, an eye state network may output a state of each eye such as eye open or closed for a binary decision network, or values such as open, closed, or partially open (potentially with some value of openness) for others. This may include some amount of measurement of openness for a partially open state, such as an inferred distance or percentage of overall blink amplitude, along with a confidence value in this state determination.

Data for at least some of these landmarks may also be passed to a neural network, process, or algorithm for determining head pose for the person, at least with respect to a point of view of a camera used to capture the image. As illustrated in FIG. 2A, the relative spacings and locations of at least some of these facial landmarks can be used to determine a pose of the head, such as a roll, pitch, and yaw of the head relative to a default orientation, axis, or coordinate system, as may correspond to a head that is centered in the image and positioned to appear to be looking directly at the camera, or orthogonal to a plane of the 2D image (if the image data is in 2D). Pose information can be useful to determine differences between landmark positions that are due to head pose or orientation, and not due to an action or behavior of the person. The pose information can also be used to normalize the positions of these landmarks, or remove the impact of the pose. For example, the pose information can be used to determine a transformation to be applied to the determined positions of the landmarks, in order to generate a representation 260 of the landmarks that has the impact of the head pose removed, so the features correspond to the face as if the face were in the default orientation or position. Such an approach can help to provide more accurate determinations of distances between features or landmarks, as well as variations in those distances over time. In at least one embodiment, facial landmark data can be compared to a three-dimensional (3D) ground truth head model in order to correlate landmarks to the model and determine a relative orientation of the model in the image. In at least one embodiment, a solvePnP technique can be used to estimate the head position and rotation in three dimensions.

Figure 2D:
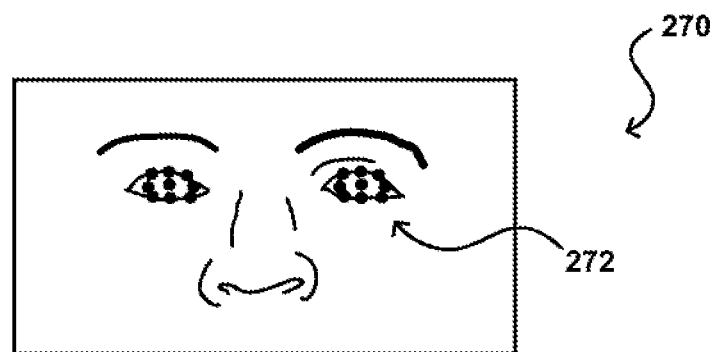
Figure 2E:

In some instances, it may be sufficient to utilize a single network to determine blink-related information, rather than to use both a facial landmark network and an eye state network. For example, as illustrated in image 270 in FIG. 2D, facial landmarks 272 can be utilized to determine when the eyes of a person are open, and as illustrated in FIG. 280, facial landmarks 282 can be used to determine when the eyes of a person are closed, as well as states in-between. These landmarks can then be used to determine information such as blink frequency, in addition to blink parameters such as blink amplitude, duration, and velocity. It may be the case, however, that the face of the user may be in a position, such as an "extreme" position, where these landmarks may be unable to be identified, at least with sufficient confidence or accuracy. This might occur, as mentioned previously, when a user is looking away from a camera, the view of the face is partially obscured, the person is wearing reflective glasses, and so on. Any uncertainty in these landmarks, or intermediate features, can result in uncertainty in blink parameter determination.

Figure 2F:
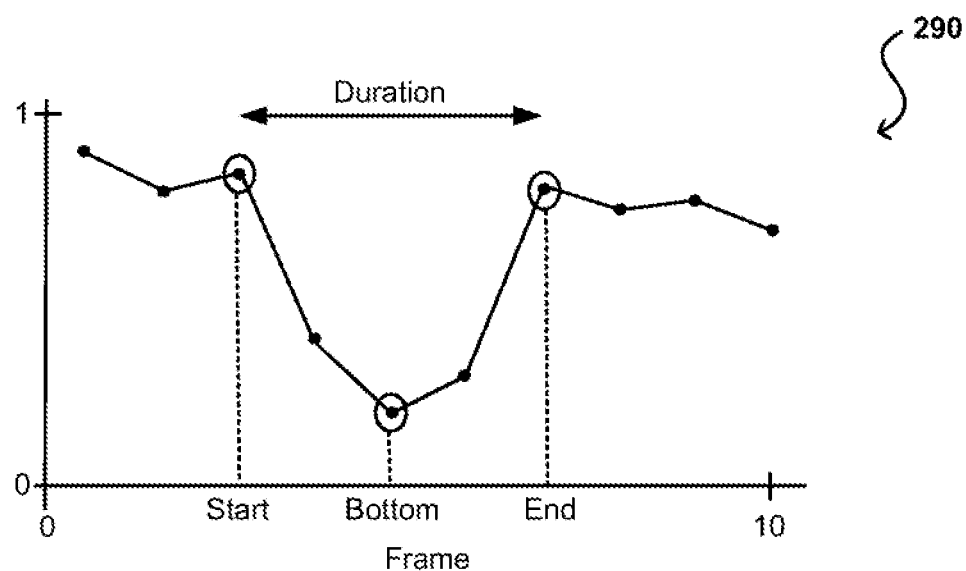

Accordingly, an eye state network can be utilized that can more accurately determine eye state in at least these extreme conditions. An eye state network can be trained in an end-to-end fashion, such that the network makes eye state inferences directly from the input image data without the need for any intermediate features or values. As long as a sufficient amount of at least one eye is represented in input image data, an eye state network can infer the eye state with relative accuracy. For blink determinations, the eye open and closed states can be determined with relative accuracy such that, even if the intermediate values have some uncertainty for partially open or closed eye states, the overall blink frequency can be determined accurately. For example, a plot 290 of eye state (e.g., aspect ratio) over time (e.g., number of frames in sequence) is illustrated in FIG. 2F. In this example it can be seen that many of the measurements correspond to an eye open state, having values (normalized to 1) that are near the maximum open state or blink amplitude. An eye closed state near the bottom of the plot represents approximately the middle of the blink action, or at least the point at which the aspect ratio is at its lowest value. Even if measurements of the eye for partially open states are not highly accurate, the overall shape of the curve will not change substantially, such that the duration between open states on either side of the blink can be determined with accuracy. Thus, as long as enough of at least one eye is visible in captured image data, an eye state network can determine eye state with sufficient accuracy to generate accurate blink frequency determinations, even for extreme positions or conditions. In at least one embodiment, an algorithm for extracting blink features can receive output from an eye state network indicating when an eye is determined to be open or closed in a current frame. The nearest frames in a sequence can be analyzed to determine whether consecutive frames have an eye closure detected. If there are multiple frames with closed eyes, the smallest eye aspect ratio (EAR) can be determined and designated as a bottom point, as illustrated in FIG. 2F, which may be based at least in part upon facial landmark data. The start frame and end frame for the blink can then also be determined using EAR values derived from facial landmark data.

As mentioned, a binary eye state network can be used with a facial landmark network to extract blink features in some embodiments. A binary eye state network can serve as a reliable binary classifier, and can identify for a given blink at least one frame where the eye was detected as closed. Any of these identified frames, as well as potentially nearby frames in a sequence, can be analyzed to determine or infer a bottom point in the aspect ratio determination. The aspect ratio can be calculated based at least in part upon facial landmarks for these frame, and thus can be used to determine a minimum eye aspect ratio for this particular user, which may vary between different individuals. The frames in this sequence can then be analyzed in each direction to identify a blink state point and a blink end point where the eye is fully open, close to fully open, or at least at or near a maximum value over a period of time. The sequence can be analyzed to determine a maximum aspect ratio, which can be set as a normal maximum aspect ratio for an open eye state, at least under current conditions for this particular subject. This value can be used to determine blink start and stop points, which can help to produce more accurate frequency and duration calculations.

Figure 3:
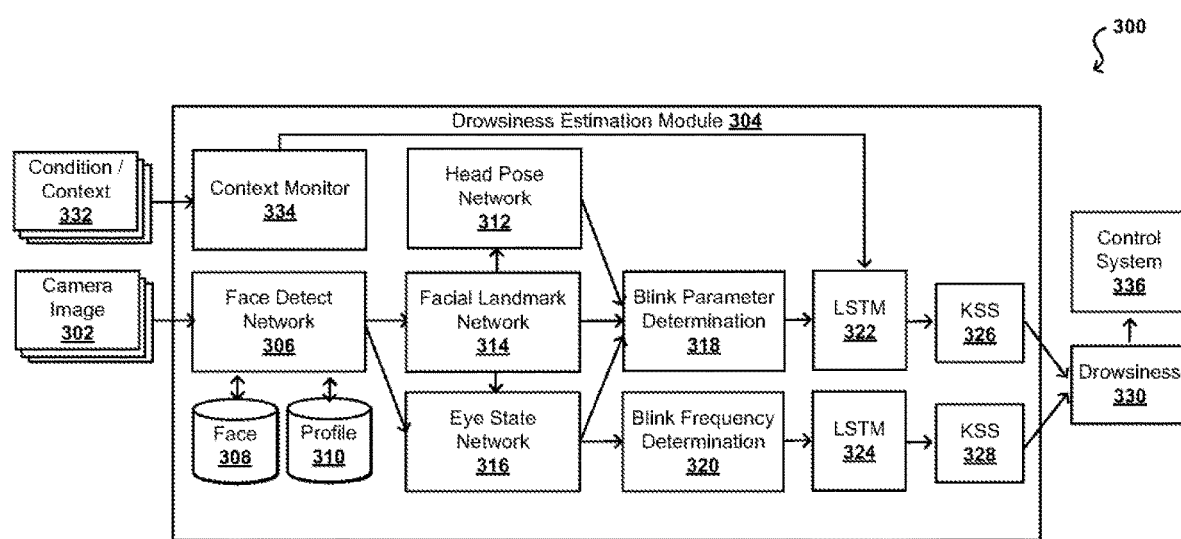
FIG. 3 illustrates an drowsiness estimation system that can be utilized, according to at least one embodiment.

FIG. 3 illustrates components of an example drowsiness estimation system 300 that can be utilized in accordance with various embodiments. In this example, one or more images 302 captured by one or more cameras (or sensors, etc.) at least partially facing a person of interest can be provided as input to a drowsiness estimation module 304 (or system, application, service, or process, etc.). For a vehicle, this module 304 may be on the vehicle itself or remote, as discussed later herein, such as in the cloud or on a remote server accessible over at least one wireless network. In other examples, portions of this functionality as may relate to face detection and/or facial landmark detection might be performed on the vehicle, in order to reduce an amount of data to be transmitted for analysis versus full image data.

In this example, the image data is passed to a face detection network 306. This network can be any appropriate neural network, such as a convolutional neural network (CNN), that is trained to infer the presence of a face in input image data. If no face is detected in an image, at least with minimum confidence, then the image data can be discarded, and no further analysis performed until subsequent data is received. If a face is detected, then at least a portion of the image data may be passed to at least a facial landmark determination network 314 for analysis. In at least some embodiments, information about the location of the detected face in the image may be passed along as well, or the input image data can be cropped to the face region before providing as input to the facial landmark detection network 314. As should be apparent, there may be additional components, processes, or modules utilized for at least some of this functionality, such as a module that is able to crop an input image to a face region given coordinates of the face region provided by the face detection network.

In at least one embodiment, information for a detected face can also be used to attempt to identify a person corresponding to a detected face. This may be performed by the face detection network or by a separate face identification module or network in communication with the face detection network. The input image, detected face data, or other information (including potentially facial landmarks determined by a facial landmark detection network 314 in some embodiments) may be compared against face data in a person database 308 or other such location. If the person is able to be identified with sufficient confidence, such as confidence that at least satisfies a minimum confidence threshold, then another determination can be made as to whether there is a profile for that person stored in a profile database 310 or otherwise accessible. As will be discussed in more detail later herein, such profile information can be used to determine specific blink behaviors of a given user, which can be used to make more accurate drowsiness estimations by accounting for variations in blink behaviors between different individuals.

As illustrated, image data for at least a face region, as well as any output from the face detection network 306 and any person profile data, can be passed to one or more neural networks for analysis. In this example, the data is passed to a facial landmark detection network 314, a head pose determination network 312, and an eye state determination network 316, although other networks, algorithms, or processes could be utilized within the scope of the various embodiments. In this example, the facial landmark network 314 can analyze at least a facial portion of an input image to attempt to infer the locations of as many facial landmarks as possible. The network can be trained to recognize any number of different landmarks, such as over 100 different landmarks in at least one embodiment, and can output a location of each detected landmark in the image, the type of that landmark, and a confidence in that determination or inference.

In at least one embodiment, at least some of the facial landmark data can be provided, potentially along with input image data, to a head pose determination network 312. The head pose determination network can be trained to infer head pose or orientation data, such as roll, pitch, and yaw, based at least in part upon the relative positions of the facial landmarks in the input image. In at least one embodiment, the head pose network can output inferred values for each of roll, pitch, and yaw, or other such orientation determinations, along with one or more corresponding confidence values. In some embodiments, a head pose determination network can be an end-to-end network that infers head pose from input image data without the use of facial landmark data, which would make the head pose determination network more robust, but since facial landmarks are being determined in this system anyway these landmarks can be used to more efficiently determine head pose with similar accuracy under most conditions. If the conditions of the head prevent the landmarks from being accurate, then the head pose information may not be used anyway as discussed elsewhere herein.

The head pose information can be provided, along with the facial landmark data, to a blink parameter determination module 318. In at least one embodiment, this module can use the head pose information to normalize the facial landmark data, or remove variations in relative distances between landmarks due to the orientation of the face in the input image data. The blink parameter determination module can then use data from this image, as well as prior images in this sequence, to determine values for various blink parameters. This can include, for example, determining blink amplitude, velocity, and duration over a recent period of time, such as a last ten seconds, thirty seconds, or minute. Values for other blink or state parameters can be determined as well within the scope of the various embodiments. Further, while these blink parameters may be handcrafted and easily understood, at least some of these parameters may be previously undetermined parameters that are learned by a network during training. In this example, these blink parameter values can then be fed to a temporal network, such as a long short-term memory (LSTM) network 322, transformer, or gate recurrent unit (GRU), or support vector machine (SVM) for analysis. The blink parameter values can be concatenated with other drowsiness indicator signals, such as steering wheel patterns (e.g., amplitude, frequency or standard deviation of steering wheel movement, reversals, etc.), lane keeping patterns (e.g., number of lane cross, standard deviation of lane position), electroencephalography/electrocardiography (EEG/ECG) patterns, and the like, as input to (LSTM) network 322. An LSTM network can apply different weights to blink values determined at different times, such as by applying greater weights to events in the recent past than in the distant past, and can use this information to infer a drowsiness value for the person. Weighting recent data more heavily helps the system to be more robust to changes in environmental data or driving context, or physiological changes in a user over time, while still accounting for patterns observed over time for a given person. As discussed later herein, this may include a determination of a first state value, such as may correspond to a Karolinska Sleepiness Scale (KSS) value for a drowsiness state determination. Other state values may be determined as well, such as may include any sleepiness scale value (e.g., a value on the Stanford Sleepiness Scale or Epworth sleepiness scale), or a value on any scale representative of fatigue due to sleepiness, for sleepiness-related state determinations. Such a value may also be generated with respect to any scale (e.g., subjective or a well-performing objective) that is representative of a loss in performance or ability, such as a loss of driving performance due to sleepiness or fatigue (or other state of interest). In at least some embodiments, a temporal network such as an LSTM may provide more accurate results that models or networks such as an SVM that can be used to attempt to determine drowsiness instantaneously instead of analyzing one or more patterns over a period of time based on multiple blinks.

As mentioned above, a drowsiness value may not always be reliable, particularly for extreme conditions such as a head turned significantly away from the camera during image capture. In order to provide a robustness of drowsiness estimation for such situations, a second estimation of drowsiness can be performed using an eye state network 316. In this example, an eye state network 316 can receive facial landmark data from a facial landmark network, at least for landmarks (or bounding boxes, etc.) relating to the eyes of a person. The eye state network can then use this information to focus on only one or more portions of an input image that represent one or more eyes of a person. In other embodiments, the eye state network may analyze an input image, or at least a face region of the image, without receiving facial landmark data. The eye state network 316 can be trained to determine the state of an eye in an image, such as whether that eye is fully open, fully closed, or partially open/closed. In at least some embodiments, the network can infer a value representative of "openness" or "closedness," such as a value between 0 for fully closed and 1 for fully open. A "fully open" eye can correspond to an eye that is open to a maximum eyelid separation observed, or otherwise possible, for this user. The network can output such a value for each eye detected, or for both eyes together, along with a respective confidence value for each determination. In at least one embodiment, this information can be provided as another input to a blink parameter determination module 318 for use in making more accurate blink parameter determinations. In this example, the eye state information can be provided, along with related information over a recent period of time, to a blink frequency determination module 320, system, device, process, or service. The blink frequency determination module 320 can analyze changes in eye state over a recent period of time to determine the occurrences of blink actions by a person, and can use this to calculate a blink frequency value over a recent period of time. This blink frequency information can be provided, along with blink frequency information for prior periods of time in this example, to another LSTM network 324 which applies different weights to blink frequency data obtained for different periods over a recent past. The frequency information can be concatenated with other drowsiness indicator signals, such as steering wheel patterns (e.g., amplitude, frequency or standard deviation of steering wheel movements, reversals, etc.), lane keeping patterns (e.g., number of lane crosses or standard deviation of lane positions), EEG/ECG data, and the like, as input to (LSTM) network 324. This LSTM network 324 can then infer a second drowsiness value for the person, which may correspond to a determination of a second KSS value. While these values can be provided separately in some embodiments, in this example these values can be used to provide a single output drowsiness estimate. Further, if the confidence values for the facial landmark data do not at least satisfy a minimum confidence threshold, such as for an extreme head position or image with a face partially obscured, then the facial landmark data may not be provided to the first LSTM network and only the second LSTM network may be used to make a drowsiness prediction for that image based on one or more results of the eye state network.

If the drowsiness values agree, at least within an allowable range of agreement, then that estimate can be provided as an output drowsiness value 330. If the values do not agree, the relative confidence values for the separate determinations can be analyzed. If one determination has high confidence but the other does not, then the determination with high confidence can be provided. In other embodiments, the value can be a blending of the two determinations weighted by confidence, such that if one score of 8 has a high confidence and one score of 5 has a low confidence, then a final result of 7 might be determined based on a higher weighting being applied to the score of 8. Various other approaches can be used as well within the scope of the various embodiments.

As mentioned, values can be inferred or generated that can provide a view of the state of a person at a specific point or period in time. While values such as KSS values have been generated previously to attempt to provide a measure or indication of a specific state, prior approaches often did not provide sufficient accuracy and robustness due to factors such as inaccurate feature detection. A system in accordance with various embodiments can overcome such deficiencies by utilizing multiple networks, where those networks can utilize or rely on different information, and thus are not limited by a single set of inaccurate features or values. As mentioned, this can include use of an eye open close network for blink detection which can be used to derive a blink frequency feature (e.g., PerCLOS), as well as a facial landmark network for blink feature extraction including blink amplitude, blink duration, and blink velocity. Such a system can also include two temporal (e.g., LSTM) networks to correlate blink events and features with KSS. Based at least in part upon facial landmark confidence and head pose data, a drowsiness estimation system can select high confidence features to train these temporal networks. If facial landmark confidence is high, a temporal network can be trained using blink frequency features together with blink amplitude, blink duration, and blink velocity feature, and these features can be frontalized (or can have the impact on position due to orientation removed) using head pose data. Otherwise, if facial landmark confidence is low, the temporal network may be trained using blink frequency data only. Such an approach can greatly improve drowsiness estimation accuracy due to use of multiple networks and robust feature selection.

Figure 4:
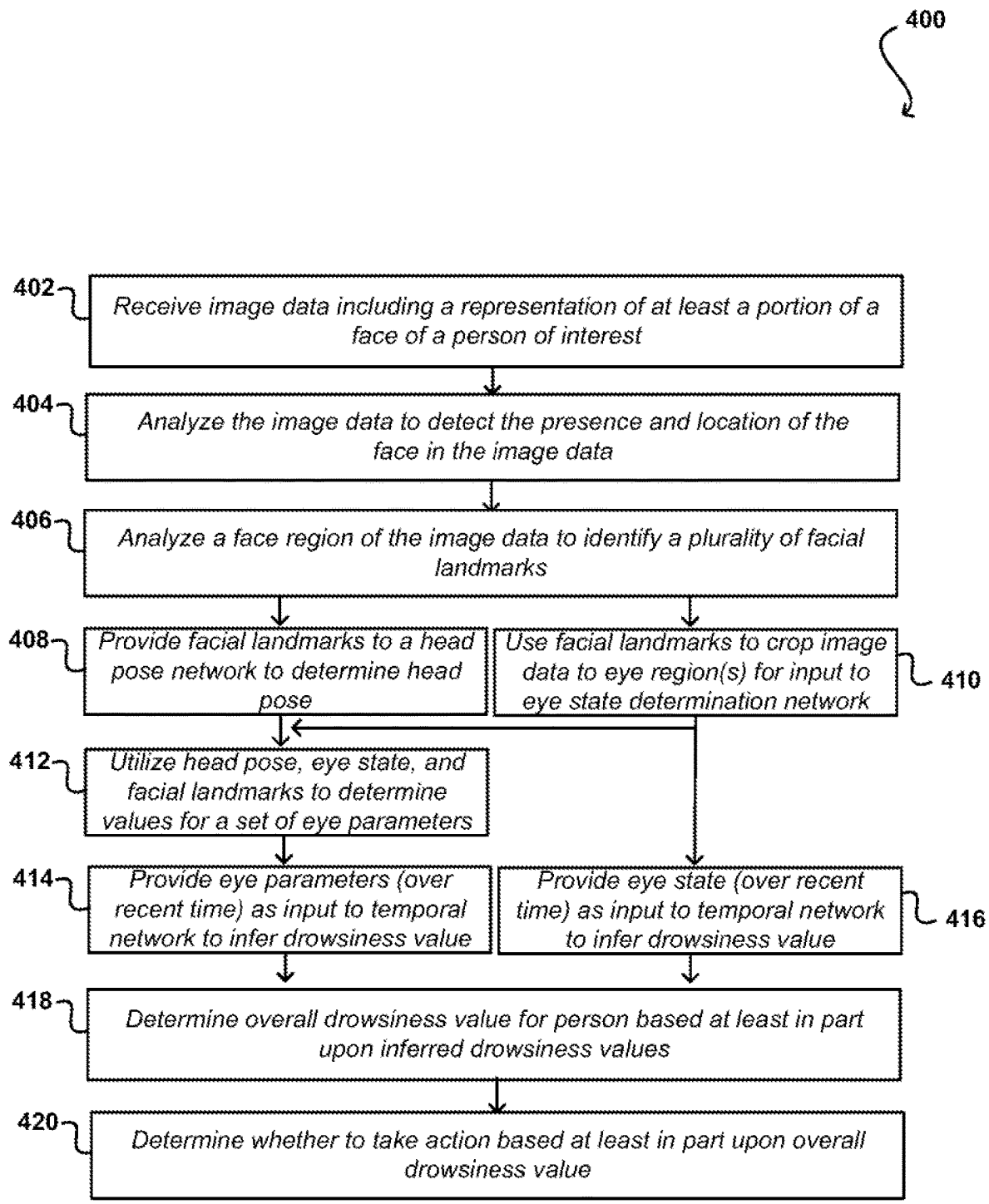
FIG. 4 illustrates an example process for estimating the state of a subject, according to at least one embodiment.

FIG. 4A illustrates an example process 400 for determining drowsiness that can be utilized in accordance with various embodiments. It should be understood that for this and other processes discussed herein that there can be additional, fewer, or alternative steps performed in similar or alternative orders, or at least partially in parallel, within the scope of the various embodiments unless otherwise specifically stated. Further, although this example is described with respect to drowsiness of a person operating a vehicle, determinations of the state of a person can be used for other types of state of a person or subject performing other types of activities as well within the scope of the various embodiments. In this example, image data is received 402 that includes a representation of at least a portion of a face of a person (or other subject) of interest, such as a driver of a vehicle. This image data can be analyzed 404 using a face detector network to determine the presence of the face, as well as information about the location of the face in the image. If no face is detected, or a face cannot be determined with at least a minimum confidence, then the process may discard this image data and wait for subsequent image data where the face can be detected. If a face is detected, at least a face region of this image data can be analyzed 406 to attempt to identify a plurality of facial landmarks that can be useful in determining state information for a person, such as a drowsiness state.

Once at least a determinable subset of the facial landmarks has been identified, these facial landmarks can be used with a number of different tasks. As one such task, at least some of these facial landmarks can be provided 408 to a head pose network to attempt to determine a head pose of the person of interest, at least as represented in the image data. In other embodiments, head pose might be determined directly from the input image data. In this example, the facial landmark data can also be used 410 to crop the input image data, or at least identify a portion of the input image data, to contain primarily one or more eye regions, such as one region for both eyes or a separate region for each eye (if represented in the image data). The image data for these one or more eye regions can be provided as input to an eye state determination network, which can determine a state of the eyes of the person, such as open or closed for a binary network, or a partially open state for a non-binary network. Any or all of the head pose, eye state, and set of facial landmarks can also be utilized 412 to determine values for a set of eye parameters, such as blink velocity, duration, and amplitude. These eye parameter values can be provided 414, along with similar values over a recent period of time, as input to a first temporal network to attempt to infer a state value, such as a drowsiness value, for the person of interest. In some embodiments, this step might only be performed if the facial landmarks and/or set of state parameters can be determined with at least a minimum level or threshold of confidence. In parallel, the eye state data from the eye state determination network can be provided 416, along with similar data over the recent period of time, to another temporal network to infer another drowsiness value that is based on eye state data independent of intermediate facial landmark data, which can make this determination more robust to variations in the input image data. An overall drowsiness value for this person can then be determined 418 based at least in part upon these inferred drowsiness values, where available. This can include, for example, performing a weighted average or selecting a most confident drowsiness value, among other such options. Once an overall drowsiness value has been determined, a system, service, application, module, or process receiving this value can determine 420 whether to take an action based at least in part upon this overall drowsiness (or other such state) value. This can include, for example, providing a notification, generating an alarm, or taking a remedial or proactive action, such as to at least partially take control over a current task being—or to be—performed by the person.

Such an approach can be highly accurate in estimating the current state of a person. It will often be the case, however, that different people will exhibit different behaviors, such as different blink behaviors. In order to improve the accuracy of state estimates for different subjects, it can be beneficial in at last some embodiments to attempt to normalize across users. There can be different base levels or ranges of how certain features or behaviors are manifested in different individuals, as may be connected to physiological states in these individuals. Different individuals can also have different patterns of optometric operation, such as different ways and rates of blinking. Drowsiness and fatigue determination can be quite complex and based on a number of different factors. A good approximation of drowsiness and fatigue can be obtained by analyzing a set of blink parameters, as at drowsiness onset the blink rate of a person can increase, with a corresponding decrease in blink velocity or increase in blink duration. The blink amplitude of that person may decrease as well at the onset of drowsiness. Any of these blink parameters, individually or in combination, can be used to estimate drowsiness of a person or subject. In order for this estimate to be accurate, however, it can be beneficial to determine how the values of these parameters change for individual subjects at different drowsiness states. There can be a significant amount of variation between subjects, as some people blink much more frequently than others, and at potentially different blink velocities, whether they are drowsy or not. As such, global thresholds or evaluations may not provide accurate results for all observed users, as a blink frequency that is normal for one person might represent a state of drowsiness for another. Accordingly, approaches in accordance with various embodiments can attempt to learn or obtain information about the actions or behaviors of individuals, in order to make estimations or evaluations that are more accurate for that particular individual.

As mentioned above, various approaches can be used to identify a person for which state estimation is to be performed. In some embodiments, this may include a user logging in or selecting a profile from an interface in a vehicle. For certain vehicles there may be other ways to identify a person, such as through various biometrics, or a person may be set as a default operator of a vehicle. In some cases, identity may be determined through use of a specific key or input. A face (or other body portion) identification or recognition system may also be used as discussed above, such as where at least one image is captured of a portion of person which can then be analyzed to attempt to determine identity. This can include, for example, comparing facial features against a feature set stored in a user database, among other such options. Once a person is identified, information for that person can be used to improve state estimations. This can include, for example, pulling behavior data from a user profile, or determining a classification or type of behavior for this person, among other such options.

A user profile (or other data repository for one or more people) can include various types of data that may be relevant for one or more types of state estimation. This can include, for example, data such as an average or "normal" blink rate or blink amplitude, as well as a typical range of such values. This enables estimates for states such as drowsiness to be performed relevant to a baseline that is accurate for that particular individual. Data for other actions, characteristics, or patterns can be stored as well, as may relate to different driving skills or behaviors for specific individuals, different reactions speeds, and so on, such as may relate to a frequency with which a person adjusts a steering wheel or pattern a person follows to change lanes. In at least some instances, these values may be vehicle dependent, and a person might have different values for different vehicles, such as for a sports car versus an SUV that might in itself have very different handling or operational characteristics. In at least one embodiment, the robustness of a state estimation system or service can be improved by accounting for population variations, such as by taking individual specifics into account during model training.

In at least one embodiment, a drowsiness model for a person can be trained using data for that individual person. This can include, for example, utilizing self-reported KSS or state data, as well as data from a subject-specific profile. Data from a subject profile can include information such as driving experience level, age, gender, nationality, or any individual difference that may cause, or be correlated with, variations in state, such as drowsiness symptoms. A subject profile can also include baseline signal values corresponding to when a subject is in a specific state, such as a specific drowsiness level, as may relate to a specific blink rate or range of blink rates, or behavior when in an alert state versus drowsy state. Profile baseline signals can be used to normalize data so that results produced using drowsiness estimation models are not significantly impacted by individual differences. For example, two subjects may have different blink rates while in an alert state, and as such will likely have different blink rate when in a drowsy or sleepy state. Without a profile baseline or other such subject-specific data, a model may have difficulty learning a threshold or range to differentiate between states, such as whether a subject is sleepy based on an absolute blink rate value. A profile baseline need not be derived from a specific state, such as an alert state, but may also or alternatively be derived from any drowsiness level. In at least one embodiment, multiple drowsiness estimation models can be trained based on different profile baseline data for any or all drowsiness levels, such that the model can estimate drowsiness given a baseline profile in any drowsiness level. In at least one embodiment, a feature vector generated by a facial landmark network, or including blink parameters determined from the output of the facial landmark network, can be normalized before being passed to an LSTM network for analysis. This can include, for example, taking the feature vector and use as a mean, or normalizing with respect to the range of features, subtracting the mean, and dividing by the standard deviation of the feature vector.

In one embodiment, when a subject enters a vehicle or is present in a monitored location, such as a driver's seat, a system can attempt to identify the person. As mentioned, this may include using facial recognition or biometrics to identify the person. If identified, the system can then attempt to determine whether that person or subject has an available profile, whether stored in non-transitory storage media in the vehicle or accessible over at least one network. If such profile is available and accessible, the system can utilize data in that profile to normalize data for that user and deploy an appropriate state estimation model. If the subject does not have an existing and accessible profile, an attempt can be made to generate such a profile. In some embodiments, this may include monitoring or capturing information related to that user over a period of time to attempt to determine baseline information. In some embodiments, the person may have an option to indicate whether the person would like to have a user calibration process performed, whereby the person can provide certain information, and have other information captured or obtained, that can be useful in generating one or more state baselines for user activity or behavior.

In order to provide accurate estimations, cameras or sensors can also be operated at relatively high capture rates. The blink duration of a user might be a fraction of a second, such that it can be beneficial to run a camera at a rate of at least 30 Hz or 60 Hz to obtain sufficient data for a blink. For example, if a blink duration for a person is around 0.2 seconds, it would be necessary to run at a capture rate of at least 30 Hz to get at least 5-6 data points for the blink, and fewer points can result in greater uncertainty in timing of blink start, middle, and end for purposes of determining values such as blink velocity and duration. In at least some embodiments, it can be desired to make this data collection as unobtrusive as possible, such that the user may even be unaware that data is being collected, and for activities such as driving the data collection will in no way decrease the safety of the activity.

If a person or subject chooses to perform user calibration, the person can be instructed to follow a specific data collection procedure in order to provide one or more rounds of data for the system to use in estimating a profile baseline specific to this subject. The subject may not need to provide a full set of data in this data collection step, as a user may not be able to provide data for all possible user states. The system can take the data that is provided for certain states, and can use this data to locate a closest profile in a profile database using, for example, a nearest neighbor search process, to locate data to use to complete that subject's profile, or at least to use to infer any missing data. As part of a calibration process, a system can allow for user feedback or input. If a subject finds that a drowsiness estimation significantly deviates from a self-reported KSS, or current perception of drowsiness, that subject can provide feedback that can be used to adjust and/or retrain the relevant model, or adjust one or more baseline values or ranges for that subject.

If a person chooses not to perform user calibration, a system can attempt to identify a profile that may approximate behavior of this particular person. This can involve, for example, analyzing captured image data to attempt to determine certain aspects of the person, such as age, gender, breathing pattern, or heart rate, and can select a profile which most closely matches people with at least some of those aspects.

Figure 5A:
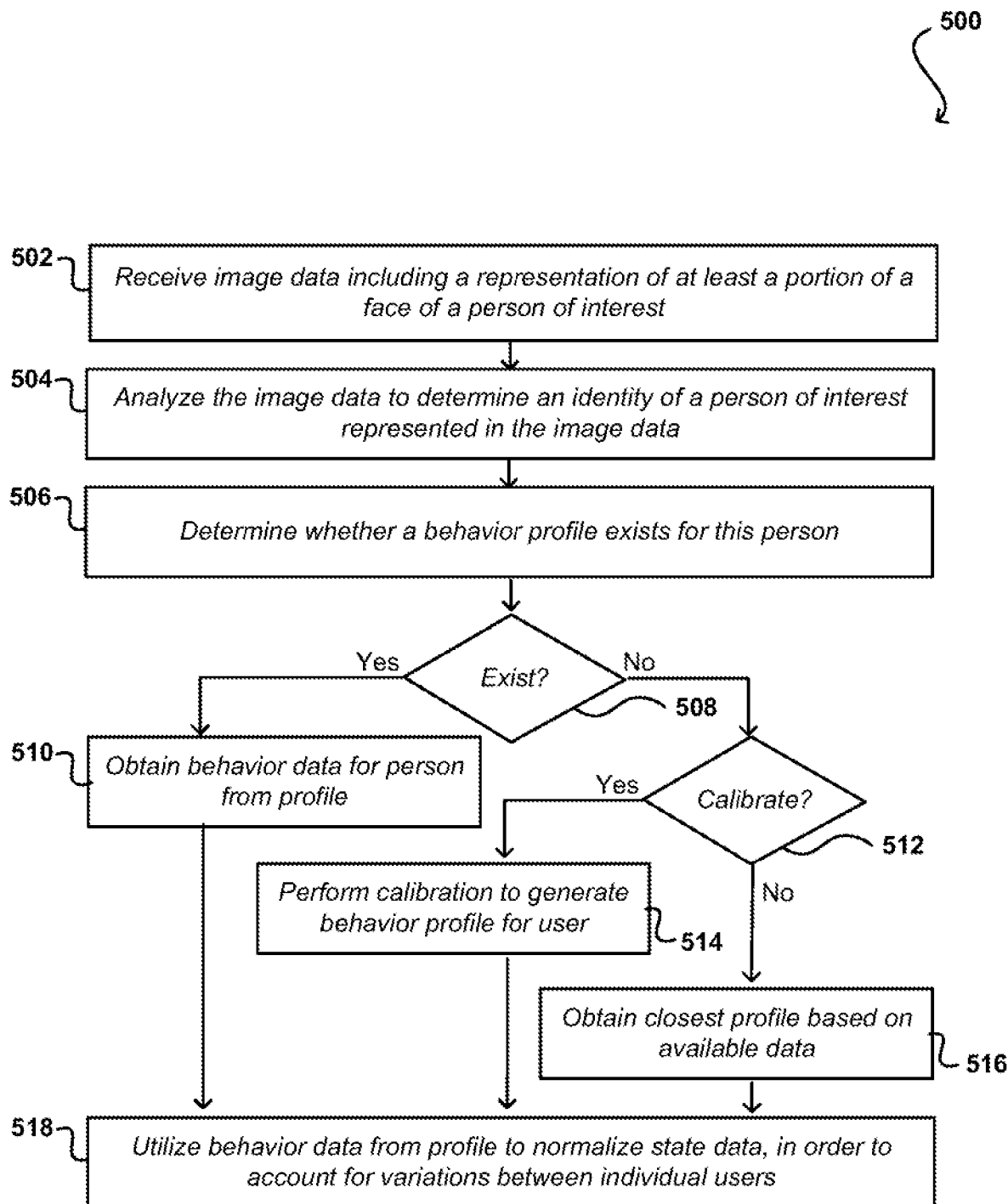
FIGS. 5A and 5B illustrate a processes for accounting for variations or behaviors not due to change in the state of a subject, according to at least one embodiment.

FIG. 5A illustrates an example process 500 for accounting for user variation in behavior data. In this example, image data is received 502 (or otherwise obtained) that includes a representation of at least a portion of a face of a person of interest. In other examples, other information may be received for the person that may help to identify that person, as may relate to biometric, identity, or other such information. In this example, this image data is analyzed 504 using a facial recognition process to determine an identity of a person of interest represented in the captured image data. A determination can then be made 506 as to whether a relevant behavior profile exists and is accessible for this person. If no identification was able to be made, then such a profile will be unable to be determined as well. If such a profile is determined 508 to exist, then relevant behavior data for this person can be obtained 510 from this profile. If such a profile does not exist or is otherwise not accessible, then the user can be requested or prompted to undergo, or participate in, a calibration process to attempt to gather information useful in building such a profile for this person. If it is determined 512 that such a calibration process can proceed, then the calibration process can be performed 514 to generate a behavior profile for that person. As mentioned, this can include collecting image and sensor data for that person, as well as potentially receiving user input as to state, in order to generate calibration, pattern, or baseline data for that person under at least certain conditions or context. Similar profiles may be consulted to attempt to fill any gaps in the profile, or provide starting points for the calibration. If calibration is not to be performed, or if the person unidentified, then a closest or default profile can be selected based upon any available and permitted data, as may relate to an aspect of the person, location, or action to be performed. In some embodiments, if a user is unable to be identified or refuses to perform any calibration, then such a process may determine to avoid usage of user behavior data to attempt to improve state determination accuracy. If a profile is determined or generated, the behavior data from that profile can be utilized 518 to normalize state data, in order to account for variations between individual users. This can include, for example, providing behavior data as an input feature vector to a temporal network that will infer a state value based upon observed input for a user, such as blink parameter values determined over a recent period of time, where person-specific baselines, ranges, or behaviors can be used to more accurately infer a state for this person.

As mentioned, there may also be variations in the behavior or actions of a person due to other factors that may be related to an environment or context in which that person is located or involved. For a person operating a vehicle, this may include various types of driving context information, as may include various environmental and other such factors. For example, a person may blink more often or squint his or her eyes when in a bright environment than in a dark environment. Further, a driver might tend to pay more attention in a crowded urban location than in a rural setting with few other vehicles or objects nearby, and may tend to move his or her eyes more frequently in such an urban setting. At least some of these environmental conditions can be determined by analyzing image or video data captured by one or more cameras associated with a vehicle, such as those illustrated in FIG. 1B. Environmental data can come from other sources as well, such as external data sources (e.g., traffic, weather, or navigation services) accessible over at least one network, internal clocks or temperature sensors, and so on. Other data obtained by sensors of a vehicle, such as some of those discussed above with respect to FIG. 1A, can also be used to determine various environmental conditions or aspects of a current driving context, such as whether a road is curvy or straight based on steering wheel movement, whether there is a lot of traffic or stops based on brake information, and so on. If GPS or navigation data is available, that information can also be used to provide at least some amount of context information for a current route or location. Brightness sensors can be used to determine lighting conditions, vehicle control systems such as steering and braking systems can be used to infer aspects of road or traffic conditions, and so on.

Such driving context can be used to improve a baseline used for state inference or estimation for a person operating within that driving context. Any or all available context information (or other pertinent information or inferences) can be analyzed to attempt to determine one or more state baselines for the person under current conditions. This may include, for example, adjusting ranges or baselines that can be used to infer different drowsiness states based on these conditions. For example, if a person is more likely to blink frequently when in a snowstorm than under normal conditions, then adjusting the baseline for this driving context can help this increase in blink frequency not be interpreted as a change in drowsiness state. Similarly, subject behavior that might normally be viewed as typical might actually indicate that the user is starting to get drowsy if the user would normally behave differently under present driving context, where failing to account for driving context might cause this increase in drowsiness to otherwise go undetected.

In some systems, the driving context can be applied similarly across all users. In other systems, individual profiles can be updated with information for different driving contexts. This can include, for example, monitoring user behavior for different driving contexts over time and updating baselines based on observed behavior. In some systems, a user may authorize collection of information that can help to calibrate the system, such as by responding to questions about drowsiness or other state while a vehicle is operating in a specific set of driving conditions or context. As with individual profiles, there may not be enough information to fill out a complete profile for various driving contexts, so the system may attempt to fill in missing information by pulling information from one or more profiles for other subjects with similar driving context variations.

The use of driving context (or similar types of environmental data for other activities) can enable a state estimation system to generalize well when tested on various individuals under various different driving contexts. In order to further improve accuracy, such a system can utilize input from multiple sources to obtain a more accurate view of user behavior, as well as current driving context or environmental conditions. Many conventional systems that attempt to determine drowsiness rely on data from only one source, such as a single sensor or method, and do not account for any variations in driving context. These systems may look for user actions such as yawning in video data or changes in steering wheel patterns as a sole indicator. Detection systems using only one of these methods without driving context have a risk of low accuracy since these drowsiness signals depend on driving context, as a driver in a same drowsiness level state but in different driving context has different physiological behavior and driving performance. By fusing information from multiple sources and considering driving context in addition to user variation and behavior, a robust drowsiness estimation system can be provided that is accurate across different subjects and conditions.

As mentioned above, for a vehicle various cameras, sensors, or data sources can be used to obtain information about a current driving context. Similar sources can be used for other types of activities. For driving context, this data may include data such as road curvature, amount or type of traffic, lane marker visibility, time of day, season, weather, lightning conditions, speed, construction, type of driving lane, road surface type, wind speed, window state, radio state or volume, interior lighting, or any other data relating to an environmental aspect that may trigger a detectable change in subject behavior, such as blinking behavior. As mentioned, if a profile is not available for a subject or the subject is unable to be identified, then a generic driving context profile may be utilized, or may be selected based at least in part upon determinable (and permissible) aspects of the subject, such as age, gender, health, or region, which may impact driving behavior. At least in part because such data may be sensitive (or impermissible in some instances) to collect or utilize for making decisions, other methods can be used to attempt to predict driving behavior for a user, such as if information can be obtained about the experience level of a driver or familiarity with a particular vehicle. Any of this information can be useful in improving profile baselines for normalizing data, enabling drowsiness or state estimation models to be minimally impacted by variations between users or situations. In at least some embodiments, multiple drowsiness estimation models can be trained based on different profile baseline in all drowsiness levels, such that a model is able to estimate drowsiness given a base line profile in any drowsiness level. Robustness is obtained at least in part because driving context affects physiological behavior and driving performance, and these effects can further vary between subjects. For example, a crowded road driving situation may need the attention of a driver attention more than driving on an empty road, and as a result cognitive load may increases, blink rate decrease, and gaze/saccades fixation increase, among other potential changes. Aspects such as road curvature, weather, route familiarity, and lighting conditions can also impact physiological behavior, as well as driving patterns such as how a driver adjusts a steering wheel and stays within a lane. For example, even for the same route under similar conditions a user may exhibit different behavior if that is the first time the user is driving that route than if the user frequently takes that route and is familiar with the route, and thus may tend to pay less attention or be less alert.

In at least one embodiment, a context monitor 334 can be used to analyze available or received data 332 relating to a driving context or other set of environmental conditions, as illustrated in FIG. 3. This can include, for example, analyzing input data to determine or infer a current driving context from among a set of possible driving contexts. In other embodiments, this can include determining a set of context inputs or features that can be used to select an appropriate baseline from an appropriate model. This context monitor can run continually, periodically, or when a significant change is detected in at least one context input, among other such options. The context monitor in some embodiments can include a neural network trained to determine driving context given a set of input. In other embodiments, one or more algorithms or processes can be used to determine one or more context factors or values from the obtained input. This driving context can then be used to determine, set, select, or calculate an appropriate baseline or range for one or more behaviors or states to be monitored under current conditions.

As with the user profile discussed above, when a subject enters a vehicle or is present in a monitored location, such as a driver's seat, a system can attempt to identify the person. If identified, the system can then attempt to determine whether that person or subject has an available profile and, if such profile is available and accessible, the system can utilize data in that profile to normalize data for that user for the current driving context and deploy an appropriate state estimation model. If the subject does not have an existing and accessible profile, an attempt can be made to generate or obtain such a profile. In some embodiments, this may include monitoring or capturing information related to that user over a period of time to attempt to determine baseline information, as well as pulling missing information from similar profiles.

In some embodiments, the blink parameters may be provided in time increments, such as for a recent minute in time. This might include, for example, a number of blinks determined over that minute, as well as information about those blinks individually or in aggregate. A determined amount of history may be retained in a history buffer, such as for a last sixty minutes or last sixty periods of blink data, and input to an LSTM network can then be a feature vector that is 60 features in length. Any driving context or user profile information can also be provided as vectors, of similar length or otherwise, input to at least one of the LSTM networks. Maintaining history of driving context or user physiological state over time can help to make more accurate determinations based on blink or state behavior over that same period of time. There may be different vectors provided for different types of context information in at least some embodiments. In at least some embodiments, the feature vectors (or make up of a given feature vector) may differ over time based at least in part upon the type or amount of context or condition data available at that time. These feature vectors for user profile and driving context data can then be used to adjust thresholds or otherwise account for expected variations (unrelated to drowsiness) to attempt to normalize the blink parameter data and detect variations in blink behavior that are due only to changes in drowsiness.

Figure 5B:
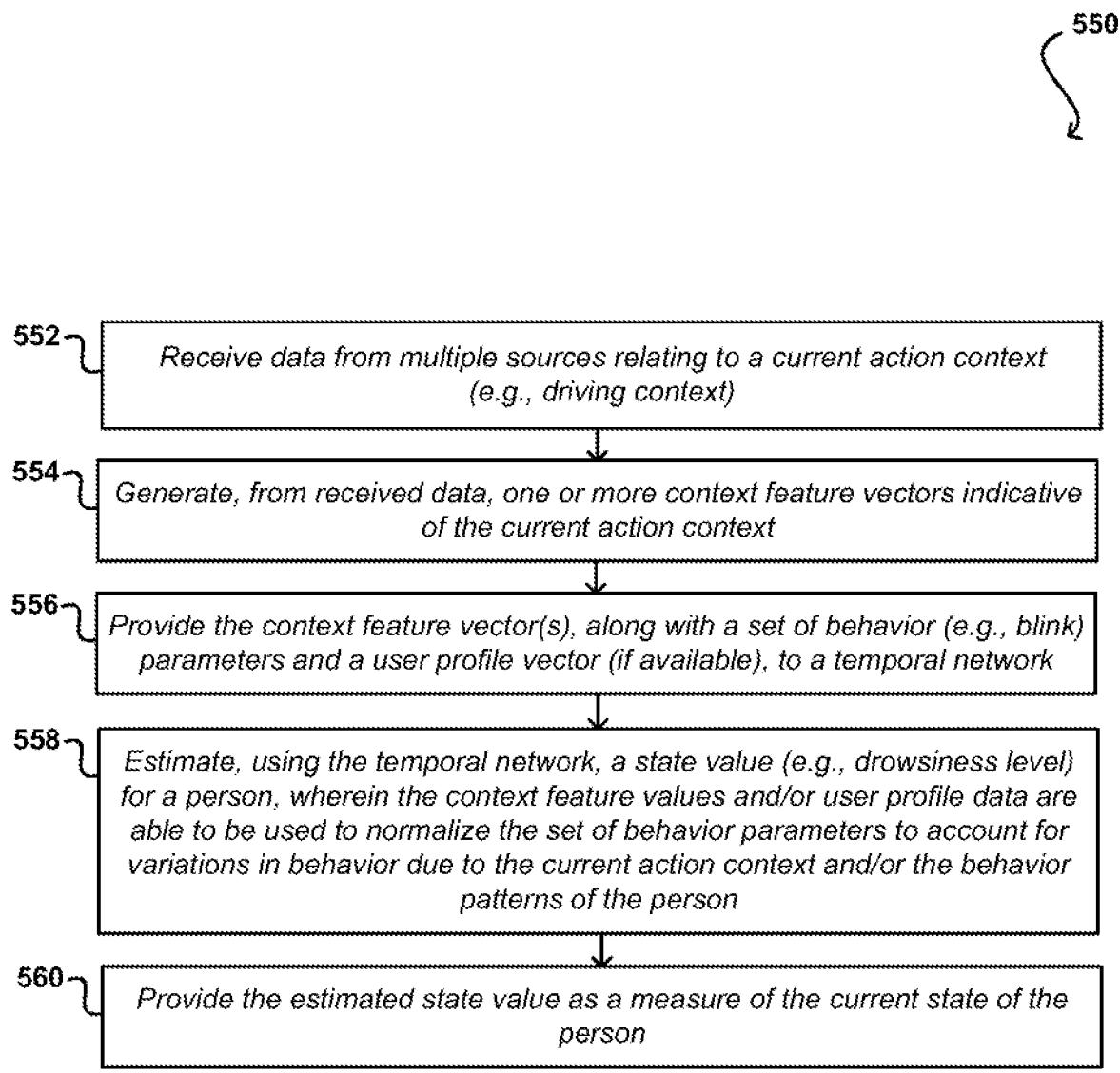

FIG. 5B illustrates an example process 550 for improving an accuracy of state estimation by considering a current action context or other environmental or conditional information. In this example, action-related context data can be received 552 from multiple sources. For a driving action, this can include any driving-context related data, as may include image data captured from cameras on a vehicle, sensor data for the vehicle, operational information for the vehicle, environmental data from a network-connected service, or positional data, among other such options as discussed and suggested elsewhere herein. In some embodiments a superset of information can be received or obtained, and a relevant subset of that data can be determined or selected. This received data can be used to generate 554 one or more content feature vectors that are indicative of a current action context. For example, the received data may be used to determine values for specific context parameters, such as type of location, weather, brightness, congestion, and so on, which can be used to make up the context feature vector(s). Any generated context feature vector, as well as any user profile vector (if available) and a set of behavior parameters measured by any appropriate sensors such as cameras, and as may include information such as steering wheel patterns, lane keeping patterns, or EEG/ECG data, among others, can be provided 556 as input to a temporal network, or other state-determination network or module. This temporal network can be used to estimate 558 a state value, such as a drowsiness level for a person, based at least in part upon this input. The context feature vectors and/or user profile data (which may also be provided in the form of one or more feature vectors) can be used to attempt to normalize the behavior parameters to account for variations in behavior that may not be due to changes in state of the person, but may instead be due to changes in a current action context or person-specific behavior patterns. An estimated state value produced by this network can then be provided 560 as a measure of the current state of the person.

Once an estimate of state is generated, information about that estimate can be used for various purposes. For example, for a drowsiness state of a driver of a vehicle, there may be a value or range of values at the onset of drowsiness that cause certain actions to be taken, such as to notify a user, sound an alarm, or display an icon indicating that the user is detected to be getting drowsy. In some embodiments, the message or alarm can be customized for the user or driving context, as actions relevant to someone on a highway in a city on a sunny day may be different from someone driving on a country road in the middle of a snowstorm. Further, different users may be more likely to take different actions, or may not appreciate certain recommendations (e.g., to drink coffee or caffeine). In at least some embodiments, recommendations may be made based at least in part upon historical or preference data for a user as well, such as where a user has stopped at a coffee shop previously on a long drive or has expressed that they do not drink caffeine. There may be other drowsiness levels or ranges where specific actions are taken by the vehicle. This can include, for example, activating a driver assistance process or changing an amount of driver assistance that is provided. For example, lane maintenance and automated braking may be increased if a driver is determined to be at a specific state of drowsiness. In some situations, a control system 336 of a vehicle may be programmed to take drastic action for high states of drowsiness indicated by the output drowsiness estimate 330, such as to engage a fully autonomous mode or to pull over to the side of the road until such time as the driver is no longer in a high state of drowsiness. In some instances, there may be regularity requirements to sound alarms or take specific actions when a driver is determined to be in a certain state. These actions can vary by location, jurisdiction, vehicle, type of subject, type of activity, or other such factors.

Various approaches presented herein are lightweight enough to execute on a various types of devices, such as personal computers, smart vehicles, or gaming consoles, in real time. Such processing can be performed using data that is captured or generated on that device or received from an external source, such as streaming data received over at least one network. The source can be any appropriate source, such as a separate client device, streaming data provider, or third party data provider, among other such options. In some instances, the processing and/or use of this data may be performed by one of these other devices, systems, or entities, then provided to a client device (or another such recipient) for presentation or another such use.

Figure 6:
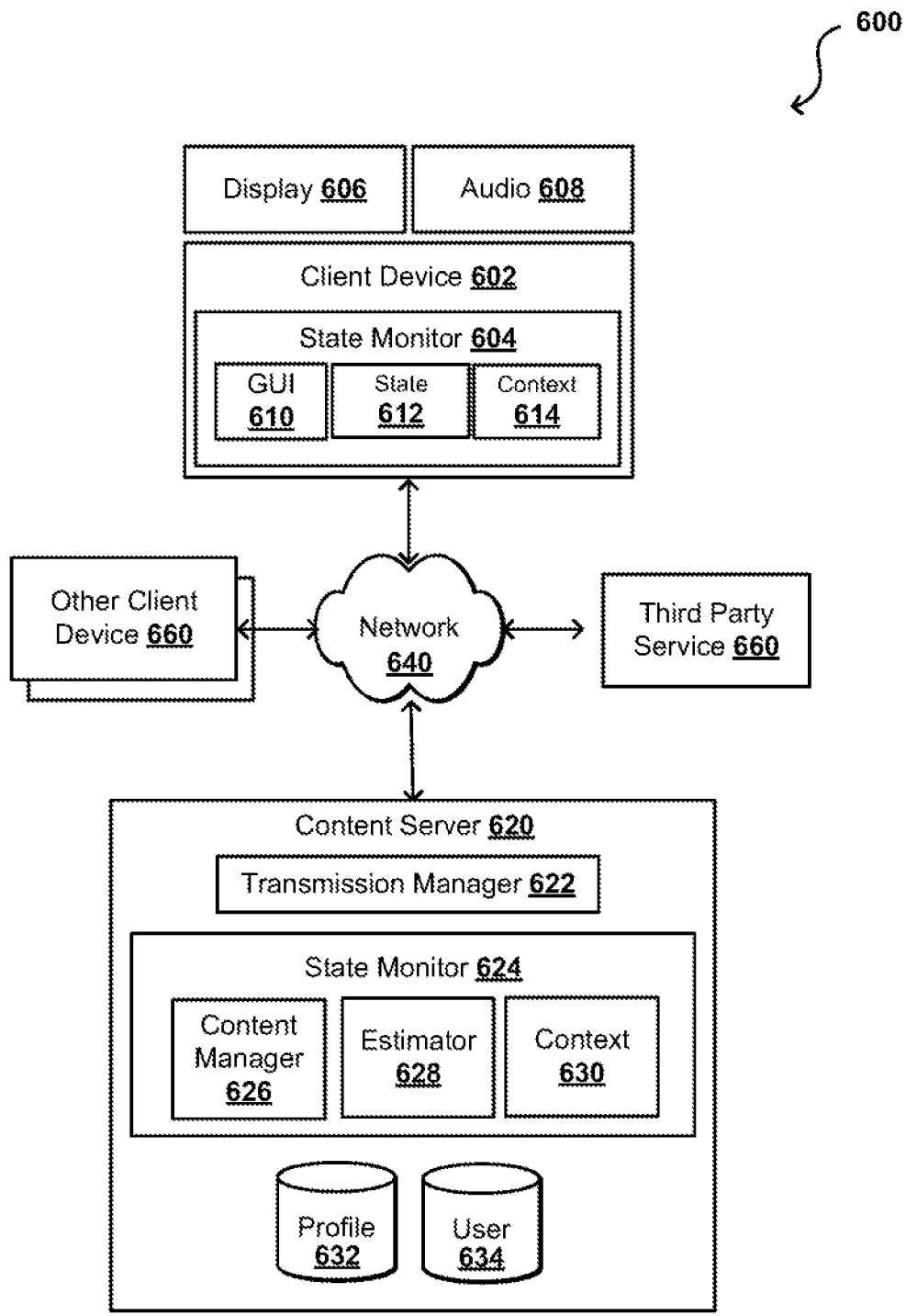
FIG. 6 illustrates components of a system for determining a state of a person, according to at least one embodiment.

As an example, FIG. 6 illustrates an example network configuration 600 that can be used to provide, generate, modify, encode, and/or transmit data. In at least one embodiment, a client device 602 can generate or receive data for a session using components of a state monitoring application 604 on a client device 602 and data stored locally on that client device. In at least one embodiment, a state monitoring application 624 executing on a data or content server 620 (e.g., a cloud server or edge server) may initiate a session associated with at least client device 602, as may utilize a session manager and user data stored in a user database 634, and can cause content to be determined by a content manager 626. An estimator module 628 may attempt to estimate state data for one or more subjects based on received data, and may work with a context module 630 to receive context data determined from received data. At least a portion of that data or state estimate may then be transmitted to client device 602 using an appropriate transmission manager 622 to send by download, streaming, or another such transmission channel. An encoder may be used to encode and/or compress this data before transmitting to the client device 602. In at least one embodiment, this data 632 can include any data relevant for a state estimation, user behavior, or action context. In at least one embodiment, client device 602 receiving this data can provide this data to a corresponding state monitor 604, which may also or alternatively include a state estimator 612 or context determination module 614 for analyzing data received to, or captured by, the client device 602. A decoder may also be used to decode data received over the network(s) 640 for presentation or action via client device 602, such as notification content through a display 606 or audio, such as an alarm or audible notification, through at least one audio playback device 608, such as speakers or headphones. In at least one embodiment, at least some of this data may already be stored on, generated on, or accessible to client device 602 such that transmission over network 640 is not required for at least that portion of data, such as where that data may have been previously downloaded or stored locally on a hard drive or optical disk. In at least one embodiment, a transmission mechanism such as data streaming can be used to transfer this data from server 620, such as from a profile database 632, to client device 602. In at least one embodiment, at least a portion of this data can be obtained, determined, or streamed from another source, such as separate client device 650 or a third party service 660 that may also include functionality for estimating state, determining user behavior patterns, or determining action context. In at least one embodiment, portions of this functionality can be performed using multiple computing devices, or multiple processors within one or more computing devices, such as may include a combination of CPUs and GPUs.

In this example, client devices can include any appropriate computing devices, as may include a desktop computer, notebook computer, set-top box, streaming device, gaming console, smartphone, tablet computer, smart vehicle, robotic-assisted machine, VR headset, AR goggles, wearable computer, or a smart television. Each client device can submit a request across at least one wired or wireless network, as may include the Internet, an Ethernet, a local area network (LAN), or a cellular network, among other such options. In this example, these requests can be submitted to an address associated with a cloud provider, who may operate or control one or more electronic resources in a cloud provider environment, such as may include a data center or server farm. In at least one embodiment, the request may be received or processed by at least one edge server, that sits on a network edge and is outside at least one security layer associated with the cloud provider environment. In this way, latency can be reduced by enabling the client devices to interact with servers that are in closer proximity, while also improving security of resources in the cloud provider environment.

In at least one embodiment, such a system can be used for performing graphical rendering operations. In other embodiments, such a system can be used for other purposes, such as for providing image or video content to test or validate autonomous machine applications, or for performing deep learning operations. In at least one embodiment, such a system can be implemented using an edge device, or may incorporate one or more Virtual Machines (VMs). In at least one embodiment, such a system can be implemented at least partially in a data center or at least partially using cloud computing resources.

Inference and Training Logic

Figure 7A:
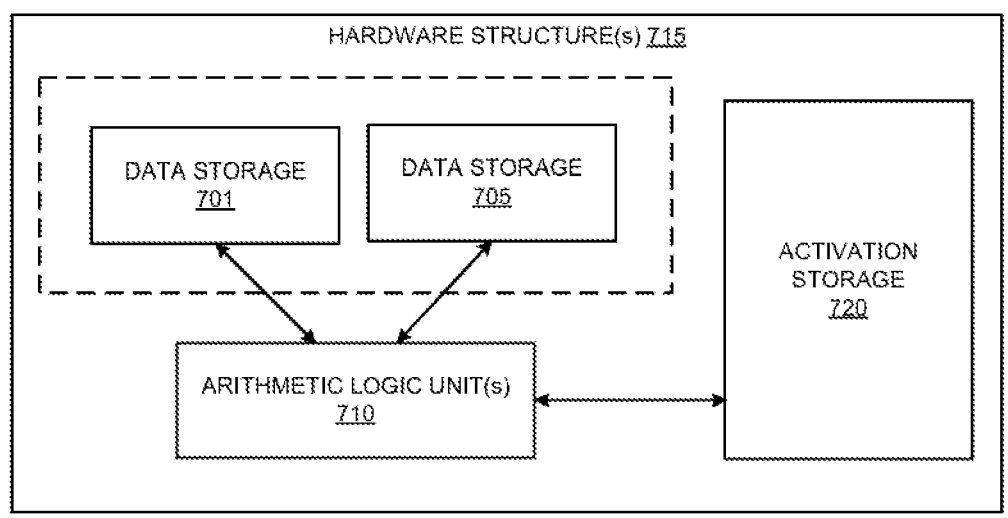
FIG. 7A illustrates inference and/or training logic, according to at least one embodiment.

FIG. 7A illustrates inference and/or training logic 715 used to perform inferencing and/or training operations associated with one or more embodiments. Details regarding inference and/or training logic 715 are provided below in conjunction with FIGS. 7A and/or 7B.

In at least one embodiment, inference and/or training logic 715 may include, without limitation, code and/or data storage 701 to store forward and/or output weight and/or input/output data, and/or other parameters to configure neurons or layers of a neural network trained and/or used for inferencing in aspects of one or more embodiments. In at least one embodiment, training logic 715 may include, or be coupled to code and/or data storage 701 to store graph code or other software to control timing and/or order, in which weight and/or other parameter information is to be loaded to configure, logic, including integer and/or floating point units (collectively, arithmetic logic units (ALUs). In at least one embodiment, code, such as graph code, loads weight or other parameter information into processor ALUs based on an architecture of a neural network to which the code corresponds. In at least one embodiment, code and/or data storage 701 stores weight parameters and/or input/output data of each layer of a neural network trained or used in conjunction with one or more embodiments during forward propagation of input/output data and/or weight parameters during training and/or inferencing using aspects of one or more embodiments. In at least one embodiment, any portion of code and/or data storage 701 may be included with other on-chip or off-chip data storage, including a processor's L1, L2, or L3 cache or system memory.

In at least one embodiment, any portion of code and/or data storage 701 may be internal or external to one or more processors or other hardware logic devices or circuits. In at least one embodiment, code and/or code and/or data storage 701 may be cache memory, dynamic randomly addressable memory ("DRAM"), static randomly addressable memory ("SRAM"), non-volatile memory (e.g., Flash memory), or other storage. In at least one embodiment, choice of whether code and/or code and/or data storage 701 is internal or external to a processor, for example, or comprised of DRAM, SRAM, Flash or some other storage type may depend on available storage on-chip versus off-chip, latency requirements of training and/or inferencing functions being performed, batch size of data used in inferencing and/or training of a neural network, or some combination of these factors.

In at least one embodiment, inference and/or training logic 715 may include, without limitation, a code and/or data storage 705 to store backward and/or output weight and/or input/output data corresponding to neurons or layers of a neural network trained and/or used for inferencing in aspects of one or more embodiments. In at least one embodiment, code and/or data storage 705 stores weight parameters and/or input/output data of each layer of a neural network trained or used in conjunction with one or more embodiments during backward propagation of input/output data and/or weight parameters during training and/or inferencing using aspects of one or more embodiments. In at least one embodiment, training logic 715 may include, or be coupled to code and/or data storage 705 to store graph code or other software to control timing and/or order, in which weight and/or other parameter information is to be loaded to configure, logic, including integer and/or floating point units (collectively, arithmetic logic units (ALUs). In at least one embodiment, code, such as graph code, loads weight or other parameter information into processor ALUs based on an architecture of a neural network to which the code corresponds. In at least one embodiment, any portion of code and/or data storage 705 may be included with other on-chip or off-chip data storage, including a processor's L1, L2, or L3 cache or system memory. In at least one embodiment, any portion of code and/or data storage 705 may be internal or external to on one or more processors or other hardware logic devices or circuits. In at least one embodiment, code and/or data storage 705 may be cache memory, DRAM, SRAM, non-volatile memory (e.g., Flash memory), or other storage. In at least one embodiment, choice of whether code and/or data storage 705 is internal or external to a processor, for example, or comprised of DRAM, SRAM, Flash or some other storage type may depend on available storage on-chip versus off-chip, latency requirements of training and/or inferencing functions being performed, batch size of data used in inferencing and/or training of a neural network, or some combination of these factors.

In at least one embodiment, code and/or data storage 701 and code and/or data storage 705 may be separate storage structures. In at least one embodiment, code and/or data storage 701 and code and/or data storage 705 may be same storage structure. In at least one embodiment, code and/or data storage 701 and code and/or data storage 705 may be partially same storage structure and partially separate storage structures. In at least one embodiment, any portion of code and/or data storage 701 and code and/or data storage 705 may be included with other on-chip or off-chip data storage, including a processor's L1, L2, or L3 cache or system memory.

In at least one embodiment, inference and/or training logic 715 may include, without limitation, one or more arithmetic logic unit(s) ("ALU(s)") 710, including integer and/or floating point units, to perform logical and/or mathematical operations based, at least in part on, or indicated by, training and/or inference code (e.g., graph code), a result of which may produce activations (e.g., output values from layers or neurons within a neural network) stored in an activation storage 720 that are functions of input/output and/or weight parameter data stored in code and/or data storage 701 and/or code and/or data storage 705. In at least one embodiment, activations stored in activation storage 720 are generated according to linear algebraic and or matrix-based mathematics performed by ALU(s) 710 in response to performing instructions or other code, wherein weight values stored in code and/or data storage 705 and/or code and/or data storage 701 are used as operands along with other values, such as bias values, gradient information, momentum values, or other parameters or hyperparameters, any or all of which may be stored in code and/or data storage 705 or code and/or data storage 701 or another storage on or off-chip.

In at least one embodiment, ALU(s) 710 are included within one or more processors or other hardware logic devices or circuits, whereas in another embodiment, ALU(s) 710 may be external to a processor or other hardware logic device or circuit that uses them (e.g., a co-processor). In at least one embodiment, ALUs 710 may be included within a processor's execution units or otherwise within a bank of ALUs accessible by a processor's execution units either within same processor or distributed between different processors of different types (e.g., central processing units, graphics processing units, fixed function units, etc.). In at least one embodiment, code and/or data storage 701, code and/or data storage 705, and activation storage 720 may be on same processor or other hardware logic device or circuit, whereas in another embodiment, they may be in different processors or other hardware logic devices or circuits, or some combination of same and different processors or other hardware logic devices or circuits. In at least one embodiment, any portion of activation storage 720 may be included with other on-chip or off-chip data storage, including a processor's L1, L2, or L3 cache or system memory. Furthermore, inferencing and/or training code may be stored with other code accessible to a processor or other hardware logic or circuit and fetched and/or processed using a processor's fetch, decode, scheduling, execution, retirement and/or other logical circuits.

In at least one embodiment, activation storage 720 may be cache memory, DRAM, SRAM, non-volatile memory (e.g., Flash memory), or other storage. In at least one embodiment, activation storage 720 may be completely or partially within or external to one or more processors or other logical circuits. In at least one embodiment, choice of whether activation storage 720 is internal or external to a processor, for example, or comprised of DRAM, SRAM, Flash or some other storage type may depend on available storage on-chip versus off-chip, latency requirements of training and/or inferencing functions being performed, batch size of data used in inferencing and/or training of a neural network, or some combination of these factors. In at least one embodiment, inference and/or training logic 715 illustrated in FIG. 7a may be used in conjunction with an application-specific integrated circuit ("ASIC"), such as Tensorflow® Processing Unit from Google, an inference processing unit (IPU) from Graphcore™, or a Nervana® (e.g., "Lake Crest") processor from Intel Corp. In at least one embodiment, inference and/or training logic 715 illustrated in FIG. 7a may be used in conjunction with central processing unit ("CPU") hardware, graphics processing unit ("GPU") hardware or other hardware, such as field programmable gate arrays ("FPGAs").

Figure 7B:
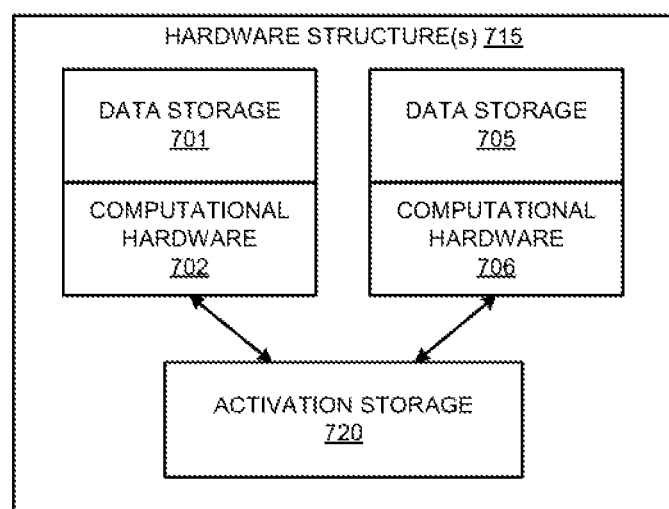
FIG. 7B illustrates inference and/or training logic, according to at least one embodiment.

FIG. 7b illustrates inference and/or training logic 715, according to at least one or more embodiments. In at least one embodiment, inference and/or training logic 715 may include, without limitation, hardware logic in which computational resources are dedicated or otherwise exclusively used in conjunction with weight values or other information corresponding to one or more layers of neurons within a neural network. In at least one embodiment, inference and/or training logic 715 illustrated in FIG. 7b may be used in conjunction with an application-specific integrated circuit (ASIC), such as Tensorflow® Processing Unit from Google, an inference processing unit (IPU) from Graphcore™, or a Nervana® (e.g., "Lake Crest") processor from Intel Corp. In at least one embodiment, inference and/or training logic 715 illustrated in FIG. 7b may be used in conjunction with central processing unit (CPU) hardware, graphics processing unit (GPU) hardware or other hardware, such as field programmable gate arrays (FPGAs). In at least one embodiment, inference and/or training logic 715 includes, without limitation, code and/or data storage 701 and code and/or data storage 705, which may be used to store code (e.g., graph code), weight values and/or other information, including bias values, gradient information, momentum values, and/or other parameter or hyperparameter information. In at least one embodiment illustrated in FIG. 7b, each of code and/or data storage 701 and code and/or data storage 705 is associated with a dedicated computational resource, such as computational hardware 702 and computational hardware 706, respectively. In at least one embodiment, each of computational hardware 702 and computational hardware 706 comprises one or more ALUs that perform mathematical functions, such as linear algebraic functions, only on information stored in code and/or data storage 701 and code and/or data storage 705, respectively, result of which is stored in activation storage 720.

In at least one embodiment, each of code and/or data storage 701 and 705 and corresponding computational hardware 702 and 706, respectively, correspond to different layers of a neural network, such that resulting activation from one "storage/computational pair 701/702" of code and/or data storage 701 and computational hardware 702 is provided as an input to "storage/computational pair 705/706" of code and/or data storage 705 and computational hardware 706, in order to mirror conceptual organization of a neural network. In at least one embodiment, each of storage/computational pairs 701/702 and 705/706 may correspond to more than one neural network layer. In at least one embodiment, additional storage/computation pairs (not shown) subsequent to or in parallel with storage computation pairs 701/702 and 705/706 may be included in inference and/or training logic 715.

Data Center

Figure 8:
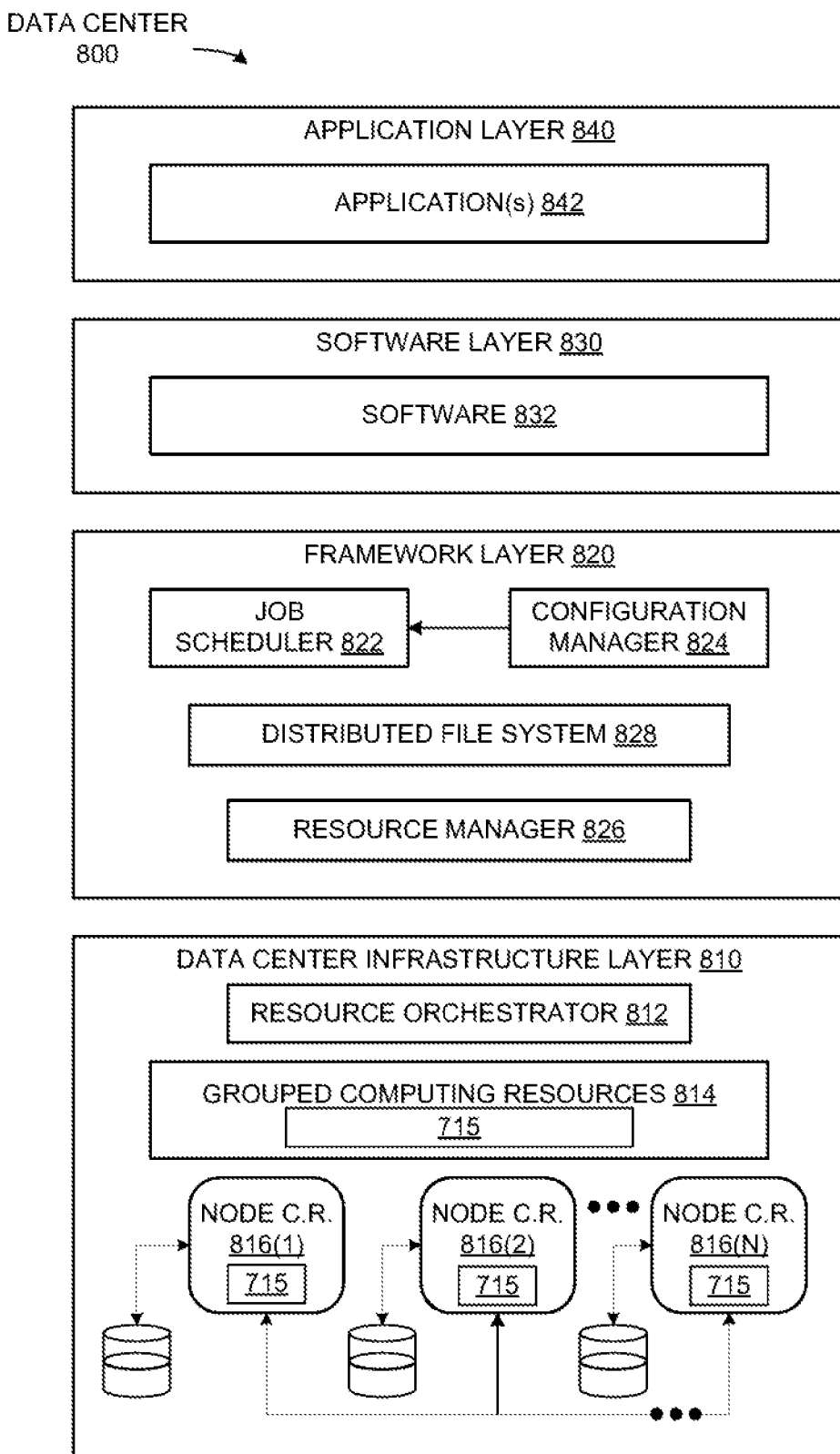
FIG. 8 illustrates an example data center system, according to at least one embodiment.

FIG. 8 illustrates an example data center 800, in which at least one embodiment may be used. In at least one embodiment, data center 800 includes a data center infrastructure layer 810, a framework layer 820, a software layer 830, and an application layer 840.

In at least one embodiment, as shown in FIG. 8, data center infrastructure layer 810 may include a resource orchestrator 812, grouped computing resources 814, and node computing resources ("node C.R.s") 816(1)-816(N), where "N" represents any whole, positive integer. In at least one embodiment, node C.R.s 816(1)-816(N) may include, but are not limited to, any number of central processing units ("CPUs") or other processors (including accelerators, field programmable gate arrays (FPGAs), graphics processors, etc.), memory devices (e.g., dynamic read-only memory), storage devices (e.g., solid state or disk drives), network input/output ("NW I/O") devices, network switches, virtual machines ("VMs"), power modules, and cooling modules, etc. In at least one embodiment, one or more node C.R.s from among node C.R.s 816(1)-816(N) may be a server having one or more of above-mentioned computing resources.

In at least one embodiment, grouped computing resources 814 may include separate groupings of node C.R.s housed within one or more racks (not shown), or many racks housed in data centers at various geographical locations (also not shown). Separate groupings of node C.R.s within grouped computing resources 814 may include grouped compute, network, memory or storage resources that may be configured or allocated to support one or more workloads. In at least one embodiment, several node C.R.s including CPUs or processors may grouped within one or more racks to provide compute resources to support one or more workloads. In at least one embodiment, one or more racks may also include any number of power modules, cooling modules, and network switches, in any combination.

In at least one embodiment, resource orchestrator 812 may configure or otherwise control one or more node C.R.s 816(1)-816(N) and/or grouped computing resources 814. In at least one embodiment, resource orchestrator 812 may include a software design infrastructure ("SDI") management entity for data center 800. In at least one embodiment, resource orchestrator may include hardware, software or some combination thereof.

In at least one embodiment, as shown in FIG. 8, framework layer 820 includes a job scheduler 822, a configuration manager 824, a resource manager 826 and a distributed file system 828. In at least one embodiment, framework layer 820 may include a framework to support software 832 of software layer 830 and/or one or more application(s) 842 of application layer 840. In at least one embodiment, software 832 or application(s) 842 may respectively include web-based service software or applications, such as those provided by Amazon Web Services, Google Cloud and Microsoft Azure. In at least one embodiment, framework layer 820 may be, but is not limited to, a type of free and open-source software web application framework such as Apache Spark™ (hereinafter "Spark") that may utilize distributed file system 828 for large-scale data processing (e.g., "big data"). In at least one embodiment, job scheduler 822 may include a Spark driver to facilitate scheduling of workloads supported by various layers of data center 800. In at least one embodiment, configuration manager 824 may be capable of configuring different layers such as software layer 830 and framework layer 820 including Spark and distributed file system 828 for supporting large-scale data processing. In at least one embodiment, resource manager 826 may be capable of managing clustered or grouped computing resources mapped to or allocated for support of distributed file system 828 and job scheduler 822. In at least one embodiment, clustered or grouped computing resources may include grouped computing resource 814 at data center infrastructure layer 810. In at least one embodiment, resource manager 826 may coordinate with resource orchestrator 812 to manage these mapped or allocated computing resources.

In at least one embodiment, software 832 included in software layer 830 may include software used by at least portions of node C.R.s 816(1)-816(N), grouped computing resources 814, and/or distributed file system 828 of framework layer 820. The one or more types of software may include, but are not limited to, Internet web page search software, e-mail virus scan software, database software, and streaming video content software.

In at least one embodiment, application(s) 842 included in application layer 840 may include one or more types of applications used by at least portions of node C.R.s 816(1)-816(N), grouped computing resources 814, and/or distributed file system 828 of framework layer 820. One or more types of applications may include, but are not limited to, any number of a genomics application, a cognitive compute, and a machine learning application, including training or inferencing software, machine learning framework software (e.g., PyTorch, TensorFlow, Caffe, etc.) or other machine learning applications used in conjunction with one or more embodiments.

In at least one embodiment, any of configuration manager 824, resource manager 826, and resource orchestrator 812 may implement any number and type of self-modifying actions based on any amount and type of data acquired in any technically feasible fashion. In at least one embodiment, self-modifying actions may relieve a data center operator of data center 800 from making possibly bad configuration decisions and possibly avoiding underutilized and/or poor performing portions of a data center.

In at least one embodiment, data center 800 may include tools, services, software or other resources to train one or more machine learning models or predict or infer information using one or more machine learning models according to one or more embodiments described herein. For example, in at least one embodiment, a machine learning model may be trained by calculating weight parameters according to a neural network architecture using software and computing resources described above with respect to data center 800. In at least one embodiment, trained machine learning models corresponding to one or more neural networks may be used to infer or predict information using resources described above with respect to data center 800 by using weight parameters calculated through one or more training techniques described herein.

In at least one embodiment, data center may use CPUs, application-specific integrated circuits (ASICs), GPUs, FPGAs, or other hardware to perform training and/or inferencing using above-described resources. Moreover, one or more software and/or hardware resources described above may be configured as a service to allow users to train or performing inferencing of information, such as image recognition, speech recognition, or other artificial intelligence services.

Inference and/or training logic 715 are used to perform inferencing and/or training operations associated with one or more embodiments. Details regarding inference and/or training logic 715 are provided below in conjunction with FIGS. 7A and/or 7B. In at least one embodiment, inference and/or training logic 715 may be used in system FIG. 8 for inferencing or predicting operations based, at least in part, on weight parameters calculated using neural network training operations, neural network functions and/or architectures, or neural network use cases described herein.

Such components can be used to composite constituent images into a single representation using parameters determined from one or more quality assessment values.

Computer Systems

Figure 9:
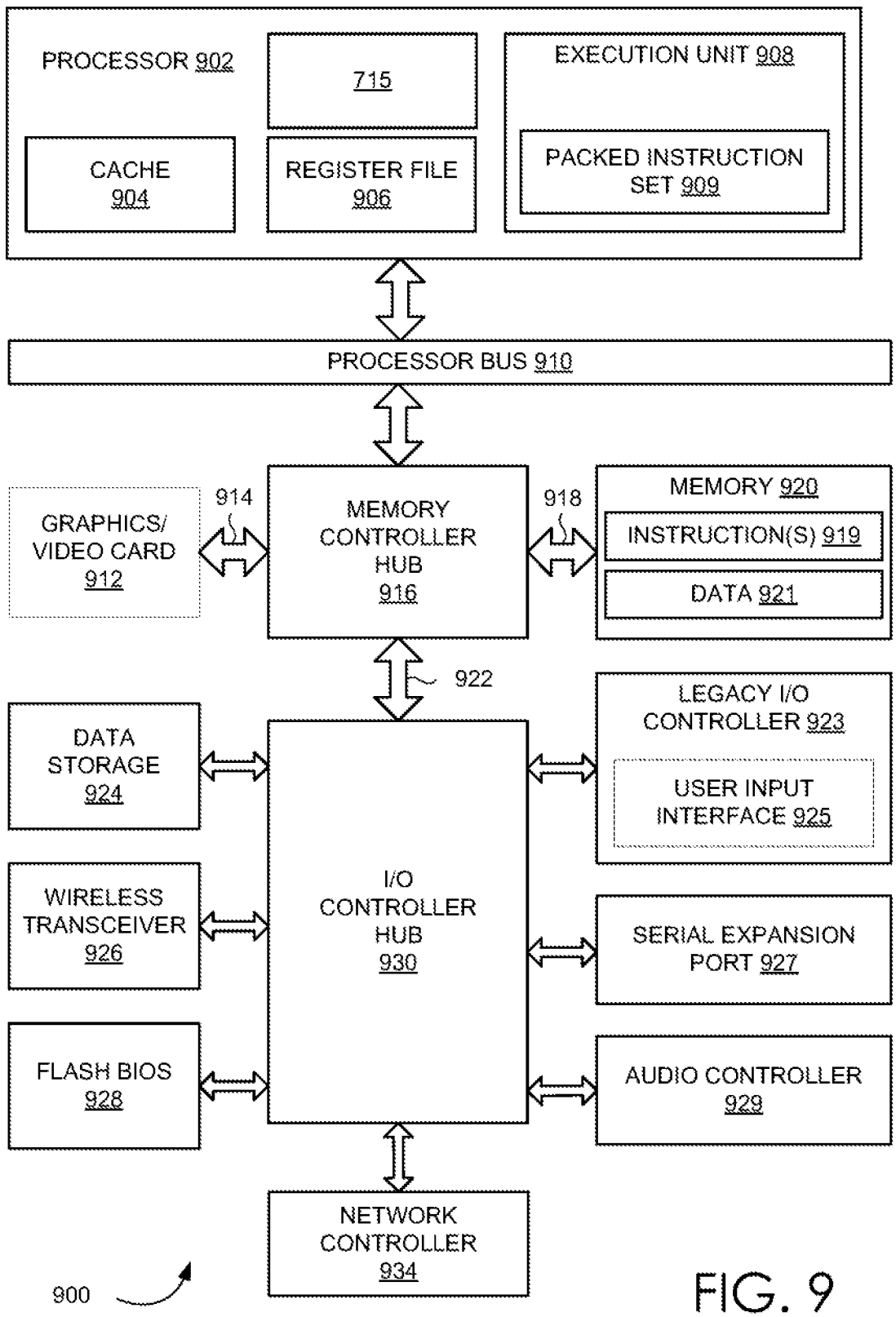
FIG. 9 illustrates a computer system, according to at least one embodiment.

FIG. 9 is a block diagram illustrating an exemplary computer system, which may be a system with interconnected devices and components, a system-on-a-chip (SOC) or some combination thereof 900 formed with a processor that may include execution units to execute an instruction, according to at least one embodiment. In at least one embodiment, computer system 900 may include, without limitation, a component, such as a processor 902 to employ execution units including logic to perform algorithms for process data, in accordance with present disclosure, such as in embodiment described herein. In at least one embodiment, computer system 900 may include processors, such as PENTIUM® Processor family, Xeon™, Itanium®, XScale™ and/or StrongARM™, Intel® Core™, or Intel® Nervana™ microprocessors available from Intel Corporation of Santa Clara, California, although other systems (including PCs having other microprocessors, engineering workstations, set-top boxes and like) may also be used. In at least one embodiment, computer system 900 may execute a version of WINDOWS' operating system available from Microsoft Corporation of Redmond, Wash., although other operating systems (UNIX and Linux for example), embedded software, and/or graphical user interfaces, may also be used.

Embodiments may be used in other devices such as handheld devices and embedded applications. Some examples of handheld devices include cellular phones, Internet Protocol devices, digital cameras, personal digital assistants ("PDAs"), and handheld PCs. In at least one embodiment, embedded applications may include a microcontroller, a digital signal processor ("DSP"), system on a chip, network computers ("NetPCs"), set-top boxes, network hubs, wide area network ("WAN") switches, or any other system that may perform one or more instructions in accordance with at least one embodiment.

In at least one embodiment, computer system 900 may include, without limitation, processor 902 that may include, without limitation, one or more execution units 908 to perform machine learning model training and/or inferencing according to techniques described herein. In at least one embodiment, computer system 900 is a single processor desktop or server system, but in another embodiment computer system 900 may be a multiprocessor system. In at least one embodiment, processor 902 may include, without limitation, a complex instruction set computer ("CISC") microprocessor, a reduced instruction set computing ("RISC") microprocessor, a very long instruction word ("VLIW") microprocessor, a processor implementing a combination of instruction sets, or any other processor device, such as a digital signal processor, for example. In at least one embodiment, processor 902 may be coupled to a processor bus 910 that may transmit data signals between processor 902 and other components in computer system 900.

In at least one embodiment, processor 902 may include, without limitation, a Level 1 ("L1") internal cache memory ("cache") 904. In at least one embodiment, processor 902 may have a single internal cache or multiple levels of internal cache. In at least one embodiment, cache memory may reside external to processor 902. Other embodiments may also include a combination of both internal and external caches depending on particular implementation and needs. In at least one embodiment, register file 906 may store different types of data in various registers including, without limitation, integer registers, floating point registers, status registers, and instruction pointer register.

In at least one embodiment, execution unit 908, including, without limitation, logic to perform integer and floating point operations, also resides in processor 902. In at least one embodiment, processor 902 may also include a microcode ("ucode") read only memory ("ROM") that stores microcode for certain macro instructions. In at least one embodiment, execution unit 908 may include logic to handle a packed instruction set 909. In at least one embodiment, by including packed instruction set 909 in an instruction set of a general-purpose processor 902, along with associated circuitry to execute instructions, operations used by many multimedia applications may be performed using packed data in a general-purpose processor 902. In one or more embodiments, many multimedia applications may be accelerated and executed more efficiently by using full width of a processor's data bus for performing operations on packed data, which may eliminate need to transfer smaller units of data across processor's data bus to perform one or more operations one data element at a time.

In at least one embodiment, execution unit 908 may also be used in microcontrollers, embedded processors, graphics devices, DSPs, and other types of logic circuits. In at least one embodiment, computer system 900 may include, without limitation, a memory 920. In at least one embodiment, memory 920 may be implemented as a Dynamic Random Access Memory ("DRAM") device, a Static Random Access Memory ("SRAM") device, flash memory device, or other memory device. In at least one embodiment, memory 920 may store instruction(s) 919 and/or data 921 represented by data signals that may be executed by processor 902.

In at least one embodiment, system logic chip may be coupled to processor bus 910 and memory 920. In at least one embodiment, system logic chip may include, without limitation, a memory controller hub ("MCH") 916, and processor 902 may communicate with MCH 916 via processor bus 910. In at least one embodiment, MCH 916 may provide a high bandwidth memory path 918 to memory 920 for instruction and data storage and for storage of graphics commands, data and textures. In at least one embodiment, MCH 916 may direct data signals between processor 902, memory 920, and other components in computer system 900 and to bridge data signals between processor bus 910, memory 920, and a system I/O 922. In at least one embodiment, system logic chip may provide a graphics port for coupling to a graphics controller. In at least one embodiment, MCH 916 may be coupled to memory 920 through a high bandwidth memory path 918 and graphics/video card 912 may be coupled to MCH 916 through an Accelerated Graphics Port ("AGP") interconnect 914.

In at least one embodiment, computer system 900 may use system I/O 922 that is a proprietary hub interface bus to couple MCH 916 to I/O controller hub ("ICH") 930. In at least one embodiment, ICH 930 may provide direct connections to some I/O devices via a local I/O bus. In at least one embodiment, local I/O bus may include, without limitation, a high-speed I/O bus for connecting peripherals to memory 920, chipset, and processor 902. Examples may include, without limitation, an audio controller 929, a firmware hub ("flash BIOS") 928, a wireless transceiver 926, a data storage 924, a legacy I/O controller 923 containing user input and keyboard interfaces 925, a serial expansion port 927, such as Universal Serial Bus ("USB"), and a network controller 934. Data storage 924 may comprise a hard disk drive, a floppy disk drive, a CD-ROM device, a flash memory device, or other mass storage device.

In at least one embodiment, FIG. 9 illustrates a system, which includes interconnected hardware devices or "chips", whereas in other embodiments, FIG. 9 may illustrate an exemplary System on a Chip ("SoC"). In at least one embodiment, devices may be interconnected with proprietary interconnects, standardized interconnects (e.g., PCIe) or some combination thereof. In at least one embodiment, one or more components of computer system 900 are interconnected using compute express link (CXL) interconnects.

Inference and/or training logic 715 are used to perform inferencing and/or training operations associated with one or more embodiments. Details regarding inference and/or training logic 715 are provided below in conjunction with FIGS. 7A and/or 7B. In at least one embodiment, inference and/or training logic 715 may be used in system FIG. 9 for inferencing or predicting operations based, at least in part, on weight parameters calculated using neural network training operations, neural network functions and/or architectures, or neural network use cases described herein.

Such components can be used to composite constituent images into a single representation using parameters determined from one or more quality assessment values.

Figure 10:
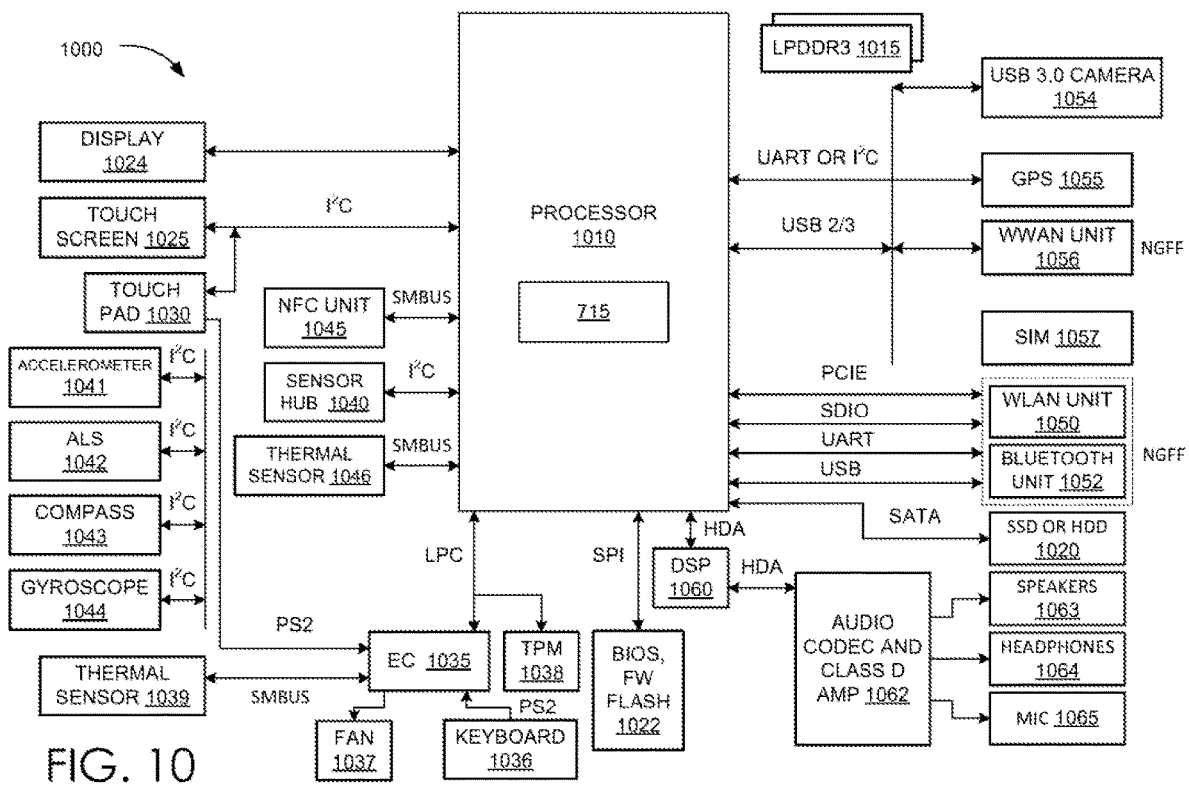
FIG. 10 illustrates a computer system, according to at least one embodiment.

FIG. 10 is a block diagram illustrating an electronic device 1000 for utilizing a processor 1010, according to at least one embodiment. In at least one embodiment, electronic device 1000 may be, for example and without limitation, a notebook, a tower server, a rack server, a blade server, a laptop, a desktop, a tablet, a mobile device, a phone, an embedded computer, or any other suitable electronic device.

In at least one embodiment, system 1000 may include, without limitation, processor 1010 communicatively coupled to any suitable number or kind of components, peripherals, modules, or devices. In at least one embodiment, processor 1010 coupled using a bus or interface, such as a 1° C. bus, a System Management Bus ("SMBus"), a Low Pin Count (LPC) bus, a Serial Peripheral Interface ("SPI"), a High Definition Audio ("HDA") bus, a Serial Advance Technology Attachment ("SATA") bus, a Universal Serial Bus ("USB") (versions 1, 2, 3), or a Universal Asynchronous Receiver/Transmitter ("UART") bus. In at least one embodiment, FIG. 10 illustrates a system, which includes interconnected hardware devices or "chips", whereas in other embodiments, FIG. 10 may illustrate an exemplary System on a Chip ("SoC"). In at least one embodiment, devices illustrated in FIG. 10 may be interconnected with proprietary interconnects, standardized interconnects (e.g., PCIe) or some combination thereof. In at least one embodiment, one or more components of FIG. 10 are interconnected using compute express link (CXL) interconnects.

In at least one embodiment, FIG. 10 may include a display 1024, a touch screen 1025, a touch pad 1030, a Near Field Communications unit ("NFC") 1045, a sensor hub 1040, a thermal sensor 1046, an Express Chipset ("EC") 1035, a Trusted Platform Module ("TPM") 1038, BIOS/firmware/flash memory ("BIOS, FW Flash") 1022, a DSP 1060, a drive 1020 such as a Solid State Disk ("SSD") or a Hard Disk Drive ("HDD"), a wireless local area network unit ("WLAN") 1050, a Bluetooth unit 1052, a Wireless Wide Area Network unit ("WWAN") 1056, a Global Positioning System (GPS) 1055, a camera ("USB 3.0 camera") 1054 such as a USB 3.0 camera, and/or a Low Power Double Data Rate ("LPDDR") memory unit ("LPDDR3") 1015 implemented in, for example, LPDDR3 standard. These components may each be implemented in any suitable manner.

In at least one embodiment, other components may be communicatively coupled to processor 1010 through components discussed above. In at least one embodiment, an accelerometer 1041, Ambient Light Sensor ("ALS") 1042, compass 1043, and a gyroscope 1044 may be communicatively coupled to sensor hub 1040. In at least one embodiment, thermal sensor 1039, a fan 1037, a keyboard 1046, and a touch pad 1030 may be communicatively coupled to EC 1035. In at least one embodiment, speaker 1063, headphones 1064, and microphone ("mic") 1065 may be communicatively coupled to an audio unit ("audio codec and class d amp") 1062, which may in turn be communicatively coupled to DSP 1060. In at least one embodiment, audio unit 1064 may include, for example and without limitation, an audio coder/decoder ("codec") and a class D amplifier. In at least one embodiment, SIM card ("SIM") 1057 may be communicatively coupled to WWAN unit 1056. In at least one embodiment, components such as WLAN unit 1050 and Bluetooth unit 1052, as well as WWAN unit 1056 may be implemented in a Next Generation Form Factor ("NGFF").

Inference and/or training logic 715 are used to perform inferencing and/or training operations associated with one or more embodiments. Details regarding inference and/or training logic 715 are provided below in conjunction with FIGS. 7a and/or 7b. In at least one embodiment, inference and/or training logic 715 may be used in system FIG. 10 for inferencing or predicting operations based, at least in part, on weight parameters calculated using neural network training operations, neural network functions and/or architectures, or neural network use cases described herein.

Such components can be used to composite constituent images into a single representation using parameters determined from one or more quality assessment values.

Figure 11:
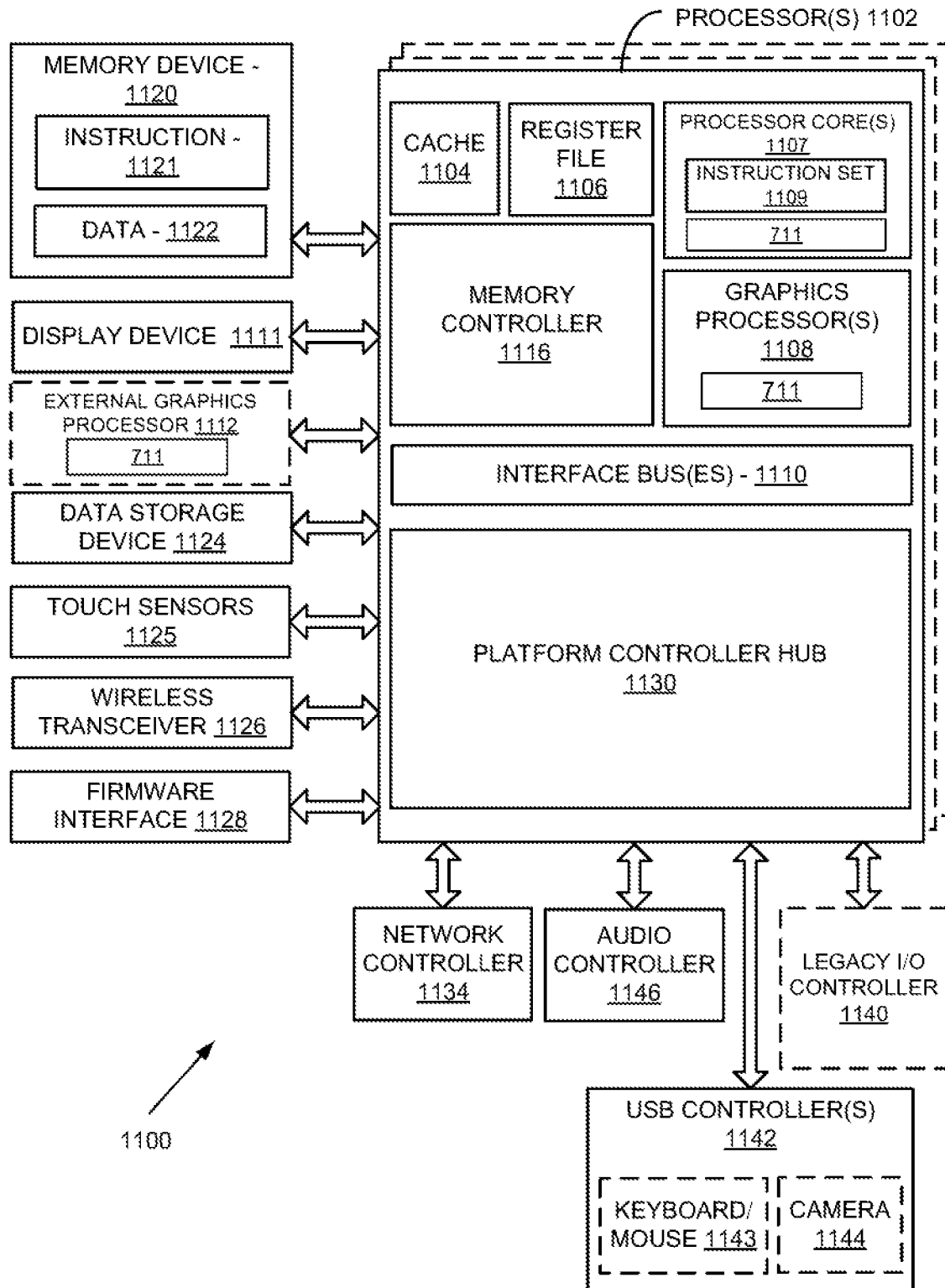
FIG. 11 illustrates at least portions of a graphics processor, according to one or more embodiments.

FIG. 11 is a block diagram of a processing system, according to at least one embodiment. In at least one embodiment, system 1100 includes one or more processors 1102 and one or more graphics processors 1108, and may be a single processor desktop system, a multiprocessor workstation system, or a server system having a large number of processors 1102 or processor cores 1107. In at least one embodiment, system 1100 is a processing platform incorporated within a system-on-a-chip (SoC) integrated circuit for use in mobile, handheld, or embedded devices.

In at least one embodiment, system 1100 can include, or be incorporated within a server-based gaming platform, a game console, including a game and media console, a mobile gaming console, a handheld game console, or an online game console. In at least one embodiment, system 1100 is a mobile phone, smart phone, tablet computing device or mobile Internet device. In at least one embodiment, processing system 1100 can also include, couple with, or be integrated within a wearable device, such as a smart watch wearable device, smart eyewear device, augmented reality device, or virtual reality device. In at least one embodiment, processing system 1100 is a television or set top box device having one or more processors 1102 and a graphical interface generated by one or more graphics processors 1108.

In at least one embodiment, one or more processors 1102 each include one or more processor cores 1107 to process instructions which, when executed, perform operations for system and user software. In at least one embodiment, each of one or more processor cores 1107 is configured to process a specific instruction set 1109. In at least one embodiment, instruction set 1109 may facilitate Complex Instruction Set Computing (CISC), Reduced Instruction Set Computing (RISC), or computing via a Very Long Instruction Word (VLIW). In at least one embodiment, processor cores 1107 may each process a different instruction set 1109, which may include instructions to facilitate emulation of other instruction sets. In at least one embodiment, processor core 1107 may also include other processing devices, such a Digital Signal Processor (DSP).

In at least one embodiment, processor 1102 includes cache memory 1104. In at least one embodiment, processor 1102 can have a single internal cache or multiple levels of internal cache. In at least one embodiment, cache memory is shared among various components of processor 1102. In at least one embodiment, processor 1102 also uses an external cache (e.g., a Level-3 (L3) cache or Last Level Cache (LLC)) (not shown), which may be shared among processor cores 1107 using known cache coherency techniques. In at least one embodiment, register file 1106 is additionally included in processor 1102 which may include different types of registers for storing different types of data (e.g., integer registers, floating point registers, status registers, and an instruction pointer register). In at least one embodiment, register file 1106 may include general-purpose registers or other registers.

In at least one embodiment, one or more processor(s) 1102 are coupled with one or more interface bus(es) 1110 to transmit communication signals such as address, data, or control signals between processor 1102 and other components in system 1100. In at least one embodiment, interface bus 1110, in one embodiment, can be a processor bus, such as a version of a Direct Media Interface (DMI) bus. In at least one embodiment, interface 1110 is not limited to a DMI bus, and may include one or more Peripheral Component Interconnect buses (e.g., PCI, PCI Express), memory busses, or other types of interface busses. In at least one embodiment processor(s) 1102 include an integrated memory controller 1116 and a platform controller hub 1130. In at least one embodiment, memory controller 1116 facilitates communication between a memory device and other components of system 1100, while platform controller hub (PCH) 1130 provides connections to I/O devices via a local I/O bus.

In at least one embodiment, memory device 1120 can be a dynamic random access memory (DRAM) device, a static random access memory (SRAM) device, flash memory device, phase-change memory device, or some other memory device having suitable performance to serve as process memory. In at least one embodiment memory device 1120 can operate as system memory for system 1100, to store data 1122 and instructions 1121 for use when one or more processors 1102 executes an application or process. In at least one embodiment, memory controller 1116 also couples with an optional external graphics processor 1112, which may communicate with one or more graphics processors 1108 in processors 1102 to perform graphics and media operations. In at least one embodiment, a display device 1111 can connect to processor(s) 1102. In at least one embodiment display device 1111 can include one or more of an internal display device, as in a mobile electronic device or a laptop device or an external display device attached via a display interface (e.g., DisplayPort, etc.). In at least one embodiment, display device 1111 can include a head mounted display (HMD) such as a stereoscopic display device for use in virtual reality (VR) applications or augmented reality (AR) applications.

In at least one embodiment, platform controller hub 1130 enables peripherals to connect to memory device 1120 and processor 1102 via a high-speed I/O bus. In at least one embodiment, I/O peripherals include, but are not limited to, an audio controller 1146, a network controller 1134, a firmware interface 1128, a wireless transceiver 1126, touch sensors 1125, a data storage device 1124 (e.g., hard disk drive, flash memory, etc.). In at least one embodiment, data storage device 1124 can connect via a storage interface (e.g., SATA) or via a peripheral bus, such as a Peripheral Component Interconnect bus (e.g., PCI, PCI Express). In at least one embodiment, touch sensors 1125 can include touch screen sensors, pressure sensors, or fingerprint sensors. In at least one embodiment, wireless transceiver 1126 can be a Wi-Fi transceiver, a Bluetooth transceiver, or a mobile network transceiver such as a 3G, 4G, or Long Term Evolution (LTE) transceiver. In at least one embodiment, firmware interface 1128 enables communication with system firmware, and can be, for example, a unified extensible firmware interface (UEFI). In at least one embodiment, network controller 1134 can enable a network connection to a wired network. In at least one embodiment, a high-performance network controller (not shown) couples with interface bus 1110. In at least one embodiment, audio controller 1146 is a multi-channel high definition audio controller. In at least one embodiment, system 1100 includes an optional legacy I/O controller 1140 for coupling legacy (e.g., Personal System 2 (PS/2)) devices to system. In at least one embodiment, platform controller hub 1130 can also connect to one or more Universal Serial Bus (USB) controllers 1142 connect input devices, such as keyboard and mouse 1143 combinations, a camera 1144, or other USB input devices.

In at least one embodiment, an instance of memory controller 1116 and platform controller hub 1130 may be integrated into a discreet external graphics processor, such as external graphics processor 1112. In at least one embodiment, platform controller hub 1130 and/or memory controller 1116 may be external to one or more processor(s) 1102. For example, in at least one embodiment, system 1100 can include an external memory controller 1116 and platform controller hub 1130, which may be configured as a memory controller hub and peripheral controller hub within a system chipset that is in communication with processor(s) 1102.

Inference and/or training logic 715 are used to perform inferencing and/or training operations associated with one or more embodiments. Details regarding inference and/or training logic 715 are provided below in conjunction with FIGS. 7A and/or 7B. In at least one embodiment portions or all of inference and/or training logic 715 may be incorporated into graphics processor 1500. For example, in at least one embodiment, training and/or inferencing techniques described herein may use one or more of ALUs embodied in a graphics processor. Moreover, in at least one embodiment, inferencing and/or training operations described herein may be done using logic other than logic illustrated in FIG. 7A or 7B. In at least one embodiment, weight parameters may be stored in on-chip or off-chip memory and/or registers (shown or not shown) that configure ALUs of a graphics processor to perform one or more machine learning algorithms, neural network architectures, use cases, or training techniques described herein.

Such components can be used to composite constituent images into a single representation using parameters determined from one or more quality assessment values.

Figure 12:
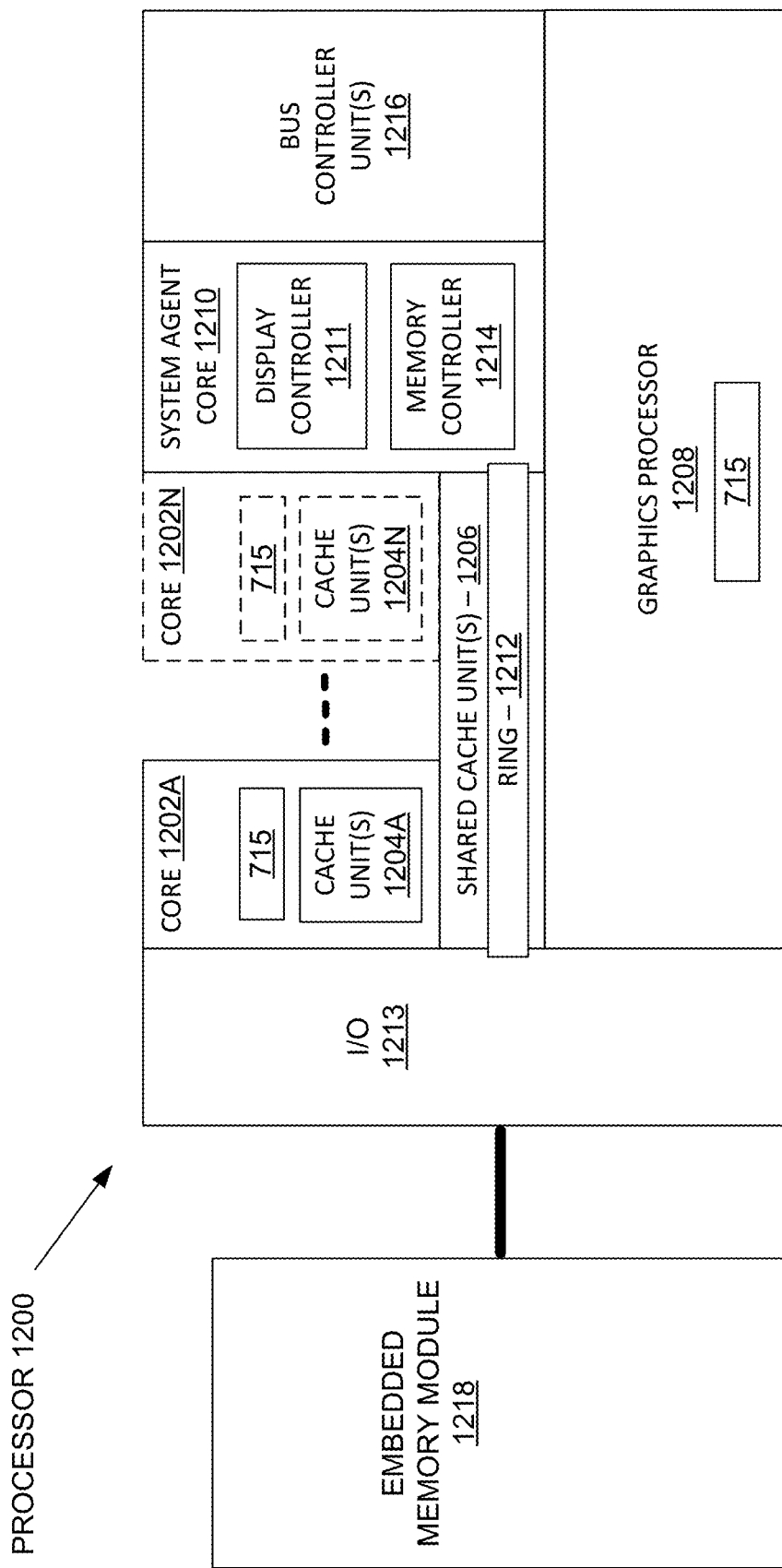
FIG. 12 illustrates at least portions of a graphics processor, according to one or more embodiments.

FIG. 12 is a block diagram of a processor 1200 having one or more processor cores 1202A-1202N, an integrated memory controller 1214, and an integrated graphics processor 1208, according to at least one embodiment. In at least one embodiment, processor 1200 can include additional cores up to and including additional core 1202N represented by dashed lined boxes. In at least one embodiment, each of processor cores 1202A-1202N includes one or more internal cache units 1204A-1204N. In at least one embodiment, each processor core also has access to one or more shared cached units 1206.

In at least one embodiment, internal cache units 1204A-1204N and shared cache units 1206 represent a cache memory hierarchy within processor 1200. In at least one embodiment, cache memory units 1204A-1204N may include at least one level of instruction and data cache within each processor core and one or more levels of shared mid-level cache, such as a Level 2 (L2), Level 3 (L3), Level 4 (L4), or other levels of cache, where a highest level of cache before external memory is classified as an LLC. In at least one embodiment, cache coherency logic maintains coherency between various cache units 1206 and 1204A-1204N.

In at least one embodiment, processor 1200 may also include a set of one or more bus controller units 1216 and a system agent core 1210. In at least one embodiment, one or more bus controller units 1216 manage a set of peripheral buses, such as one or more PCI or PCI express busses. In at least one embodiment, system agent core 1210 provides management functionality for various processor components. In at least one embodiment, system agent core 1210 includes one or more integrated memory controllers 1214 to manage access to various external memory devices (not shown).

In at least one embodiment, one or more of processor cores 1202A-1202N include support for simultaneous multi-threading. In at least one embodiment, system agent core 1210 includes components for coordinating and operating cores 1202A-1202N during multi-threaded processing. In at least one embodiment, system agent core 1210 may additionally include a power control unit (PCU), which includes logic and components to regulate one or more power states of processor cores 1202A-1202N and graphics processor 1208.

In at least one embodiment, processor 1200 additionally includes graphics processor 1208 to execute graphics processing operations. In at least one embodiment, graphics processor 1208 couples with shared cache units 1206, and system agent core 1210, including one or more integrated memory controllers 1214. In at least one embodiment, system agent core 1210 also includes a display controller 1211 to drive graphics processor output to one or more coupled displays. In at least one embodiment, display controller 1211 may also be a separate module coupled with graphics processor 1208 via at least one interconnect, or may be integrated within graphics processor 1208.

In at least one embodiment, a ring based interconnect unit 1212 is used to couple internal components of processor 1200. In at least one embodiment, an alternative interconnect unit may be used, such as a point-to-point interconnect, a switched interconnect, or other techniques. In at least one embodiment, graphics processor 1208 couples with ring interconnect 1212 via an I/O link 1213.

In at least one embodiment, I/O link 1213 represents at least one of multiple varieties of I/O interconnects, including an on package I/O interconnect which facilitates communication between various processor components and a high-performance embedded memory module 1218, such as an eDRAM module. In at least one embodiment, each of processor cores 1202A-1202N and graphics processor 1208 use embedded memory modules 1218 as a shared Last Level Cache.

In at least one embodiment, processor cores 1202A-1202N are homogenous cores executing a common instruction set architecture. In at least one embodiment, processor cores 1202A-1202N are heterogeneous in terms of instruction set architecture (ISA), where one or more of processor cores 1202A-1202N execute a common instruction set, while one or more other cores of processor cores 1202A-1202N executes a subset of a common instruction set or a different instruction set. In at least one embodiment, processor cores 1202A-1202N are heterogeneous in terms of microarchitecture, where one or more cores having a relatively higher power consumption couple with one or more power cores having a lower power consumption. In at least one embodiment, processor 1200 can be implemented on one or more chips or as an SoC integrated circuit.

Inference and/or training logic 715 are used to perform inferencing and/or training operations associated with one or more embodiments. Details regarding inference and/or training logic 715 are provided below in conjunction with FIGS. 7a and/or 7b. In at least one embodiment portions or all of inference and/or training logic 715 may be incorporated into processor 1200. For example, in at least one embodiment, training and/or inferencing techniques described herein may use one or more of ALUs embodied in graphics processor 1512, graphics core(s) 1202A-1202N, or other components in FIG. 12. Moreover, in at least one embodiment, inferencing and/or training operations described herein may be done using logic other than logic illustrated in FIG. 7A or 7B. In at least one embodiment, weight parameters may be stored in on-chip or off-chip memory and/or registers (shown or not shown) that configure ALUs of graphics processor 1200 to perform one or more machine learning algorithms, neural network architectures, use cases, or training techniques described herein.

Such components can be used to composite constituent images into a single representation using parameters determined from one or more quality assessment values.

Virtualized Computing Platform

Figure 13:
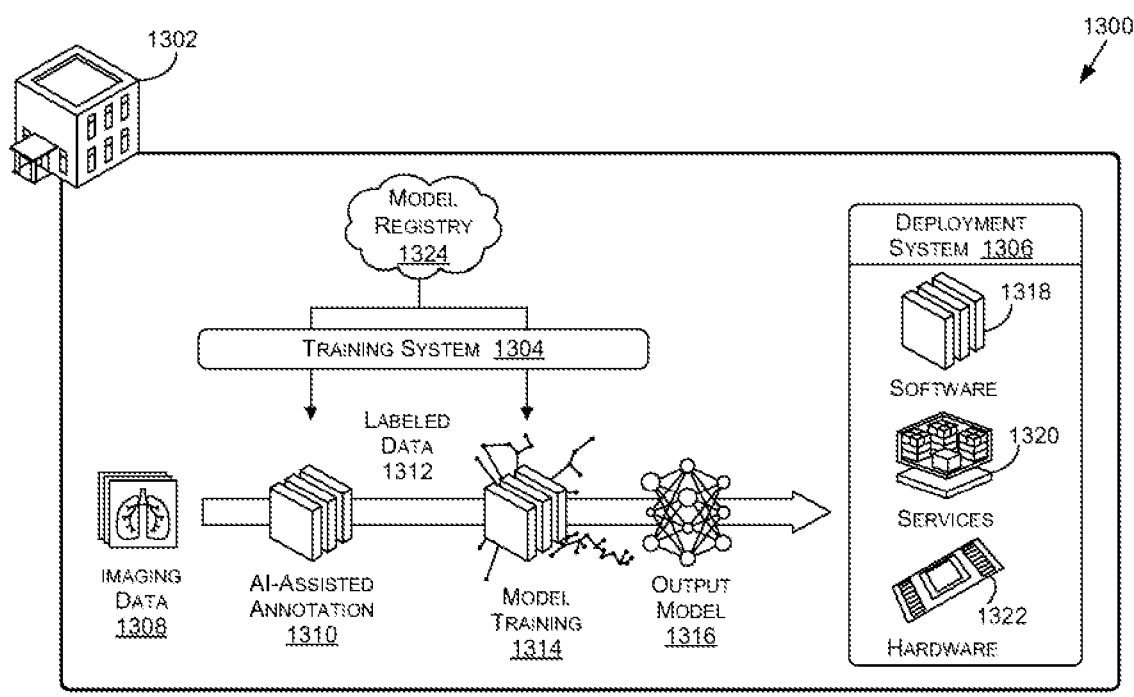
FIG. 13 is an example data flow diagram for an advanced computing pipeline, in accordance with at least one embodiment.

FIG. 13 is an example data flow diagram for a process 1300 of generating and deploying an image processing and inferencing pipeline, in accordance with at least one embodiment. In at least one embodiment, process 1300 may be deployed for use with imaging devices, processing devices, and/or other device types at one or more facilities 1302. Process 1300 may be executed within a training system 1304 and/or a deployment system 1306. In at least one embodiment, training system 1304 may be used to perform training, deployment, and implementation of machine learning models (e.g., neural networks, object detection algorithms, computer vision algorithms, etc.) for use in deployment system 1306. In at least one embodiment, deployment system 1306 may be configured to offload processing and compute resources among a distributed computing environment to reduce infrastructure requirements at facility 1302. In at least one embodiment, one or more applications in a pipeline may use or call upon services (e.g., inference, visualization, compute, AI, etc.) of deployment system 1306 during execution of applications.

In at least one embodiment, some of applications used in advanced processing and inferencing pipelines may use machine learning models or other AI to perform one or more processing steps. In at least one embodiment, machine learning models may be trained at facility 1302 using data 1308 (such as imaging data) generated at facility 1302 (and stored on one or more picture archiving and communication system (PACS) servers at facility 1302), may be trained using imaging or sequencing data 1308 from another facility (ies), or a combination thereof. In at least one embodiment, training system 1304 may be used to provide applications, services, and/or other resources for generating working, deployable machine learning models for deployment system 1306.

In at least one embodiment, model registry 1324 may be backed by object storage that may support versioning and object metadata. In at least one embodiment, object storage may be accessible through, for example, a cloud storage (e.g., cloud 1426 of FIG. 14) compatible application programming interface (API) from within a cloud platform. In at least one embodiment, machine learning models within model registry 1324 may uploaded, listed, modified, or deleted by developers or partners of a system interacting with an API. In at least one embodiment, an API may provide access to methods that allow users with appropriate credentials to associate models with applications, such that models may be executed as part of execution of containerized instantiations of applications.

In at least one embodiment, training pipeline 1404 (FIG. 14) may include a scenario where facility 1302 is training their own machine learning model, or has an existing machine learning model that needs to be optimized or updated. In at least one embodiment, imaging data 1308 generated by imaging device(s), sequencing devices, and/or other device types may be received. In at least one embodiment, once imaging data 1308 is received, AI-assisted annotation 1310 may be used to aid in generating annotations corresponding to imaging data 1308 to be used as ground truth data for a machine learning model. In at least one embodiment, AI-assisted annotation 1310 may include one or more machine learning models (e.g., convolutional neural networks (CNNs)) that may be trained to generate annotations corresponding to certain types of imaging data 1308 (e.g., from certain devices). In at least one embodiment, AI-assisted annotations 1310 may then be used directly, or may be adjusted or fine-tuned using an annotation tool to generate ground truth data. In at least one embodiment, AI-assisted annotations 1310, labeled clinic data 1312, or a combination thereof may be used as ground truth data for training a machine learning model. In at least one embodiment, a trained machine learning model may be referred to as output model 1316, and may be used by deployment system 1306, as described herein.

In at least one embodiment, training pipeline 1404 (FIG. 14) may include a scenario where facility 1302 needs a machine learning model for use in performing one or more processing tasks for one or more applications in deployment system 1306, but facility 1302 may not currently have such a machine learning model (or may not have a model that is optimized, efficient, or effective for such purposes). In at least one embodiment, an existing machine learning model may be selected from a model registry 1324. In at least one embodiment, model registry 1324 may include machine learning models trained to perform a variety of different inference tasks on imaging data. In at least one embodiment, machine learning models in model registry 1324 may have been trained on imaging data from different facilities than facility 1302 (e.g., facilities remotely located). In at least one embodiment, machine learning models may have been trained on imaging data from one location, two locations, or any number of locations. In at least one embodiment, when being trained on imaging data from a specific location, training may take place at that location, or at least in a manner that protects confidentiality of imaging data or restricts imaging data from being transferred off-premises. In at least one embodiment, once a model is trained—or partially trained—at one location, a machine learning model may be added to model registry 1324. In at least one embodiment, a machine learning model may then be retrained, or updated, at any number of other facilities, and a retrained or updated model may be made available in model registry 1324. In at least one embodiment, a machine learning model may then be selected from model registry 1324—and referred to as output model 1316—and may be used in deployment system 1306 to perform one or more processing tasks for one or more applications of a deployment system.

In at least one embodiment, training pipeline 1404 (FIG. 14), a scenario may include facility 1302 requiring a machine learning model for use in performing one or more processing tasks for one or more applications in deployment system 1306, but facility 1302 may not currently have such a machine learning model (or may not have a model that is optimized, efficient, or effective for such purposes). In at least one embodiment, a machine learning model selected from model registry 1324 may not be fine-tuned or optimized for imaging data 1308 generated at facility 1302 because of differences in populations, robustness of training data used to train a machine learning model, diversity in anomalies of training data, and/or other issues with training data. In at least one embodiment, AI-assisted annotation 1310 may be used to aid in generating annotations corresponding to imaging data 1308 to be used as ground truth data for retraining or updating a machine learning model. In at least one embodiment, labeled data 1312 may be used as ground truth data for training a machine learning model. In at least one embodiment, retraining or updating a machine learning model may be referred to as model training 1314. In at least one embodiment, model training 1314—e.g., AI-assisted annotations 1310, labeled clinic data 1312, or a combination thereof—may be used as ground truth data for retraining or updating a machine learning model. In at least one embodiment, a trained machine learning model may be referred to as output model 1316, and may be used by deployment system 1306, as described herein.

In at least one embodiment, deployment system 1306 may include software 1318, services 1320, hardware 1322, and/or other components, features, and functionality. In at least one embodiment, deployment system 1306 may include a software "stack," such that software 1318 may be built on top of services 1320 and may use services 1320 to perform some or all of processing tasks, and services 1320 and software 1318 may be built on top of hardware 1322 and use hardware 1322 to execute processing, storage, and/or other compute tasks of deployment system 1306. In at least one embodiment, software 1318 may include any number of different containers, where each container may execute an instantiation of an application. In at least one embodiment, each application may perform one or more processing tasks in an advanced processing and inferencing pipeline (e.g., inferencing, object detection, feature detection, segmentation, image enhancement, calibration, etc.). In at least one embodiment, an advanced processing and inferencing pipeline may be defined based on selections of different containers that are desired or required for processing imaging data 1308, in addition to containers that receive and configure imaging data for use by each container and/or for use by facility 1302 after processing through a pipeline (e.g., to convert outputs back to a usable data type). In at least one embodiment, a combination of containers within software 1318 (e.g., that make up a pipeline) may be referred to as a virtual instrument (as described in more detail herein), and a virtual instrument may leverage services 1320 and hardware 1322 to execute some or all processing tasks of applications instantiated in containers.

In at least one embodiment, a data processing pipeline may receive input data (e.g., imaging data 1308) in a specific format in response to an inference request (e.g., a request from a user of deployment system 1306). In at least one embodiment, input data may be representative of one or more images, video, and/or other data representations generated by one or more imaging devices. In at least one embodiment, data may undergo pre-processing as part of data processing pipeline to prepare data for processing by one or more applications. In at least one embodiment, post-processing may be performed on an output of one or more inferencing tasks or other processing tasks of a pipeline to prepare an output data for a next application and/or to prepare output data for transmission and/or use by a user (e.g., as a response to an inference request). In at least one embodiment, inferencing tasks may be performed by one or more machine learning models, such as trained or deployed neural networks, which may include output models 1316 of training system 1304.

In at least one embodiment, tasks of data processing pipeline may be encapsulated in a container(s) that each represents a discrete, fully functional instantiation of an application and virtualized computing environment that is able to reference machine learning models. In at least one embodiment, containers or applications may be published into a private (e.g., limited access) area of a container registry (described in more detail herein), and trained or deployed models may be stored in model registry 1324 and associated with one or more applications. In at least one embodiment, images of applications (e.g., container images) may be available in a container registry, and once selected by a user from a container registry for deployment in a pipeline, an image may be used to generate a container for an instantiation of an application for use by a user's system.

In at least one embodiment, developers (e.g., software developers, clinicians, doctors, etc.) may develop, publish, and store applications (e.g., as containers) for performing image processing and/or inferencing on supplied data. In at least one embodiment, development, publishing, and/or storing may be performed using a software development kit (SDK) associated with a system (e.g., to ensure that an application and/or container developed is compliant with or compatible with a system). In at least one embodiment, an application that is developed may be tested locally (e.g., at a first facility, on data from a first facility) with an SDK which may support at least some of services 1320 as a system (e.g., system 1400 of FIG. 14). In at least one embodiment, because DICOM objects may contain anywhere from one to hundreds of images or other data types, and due to a variation in data, a developer may be responsible for managing (e.g., setting constructs for, building pre-processing into an application, etc.) extraction and preparation of incoming data. In at least one embodiment, once validated by system 1400 (e.g., for accuracy), an application may be available in a container registry for selection and/or implementation by a user to perform one or more processing tasks with respect to data at a facility (e.g., a second facility) of a user.

Figure 14:
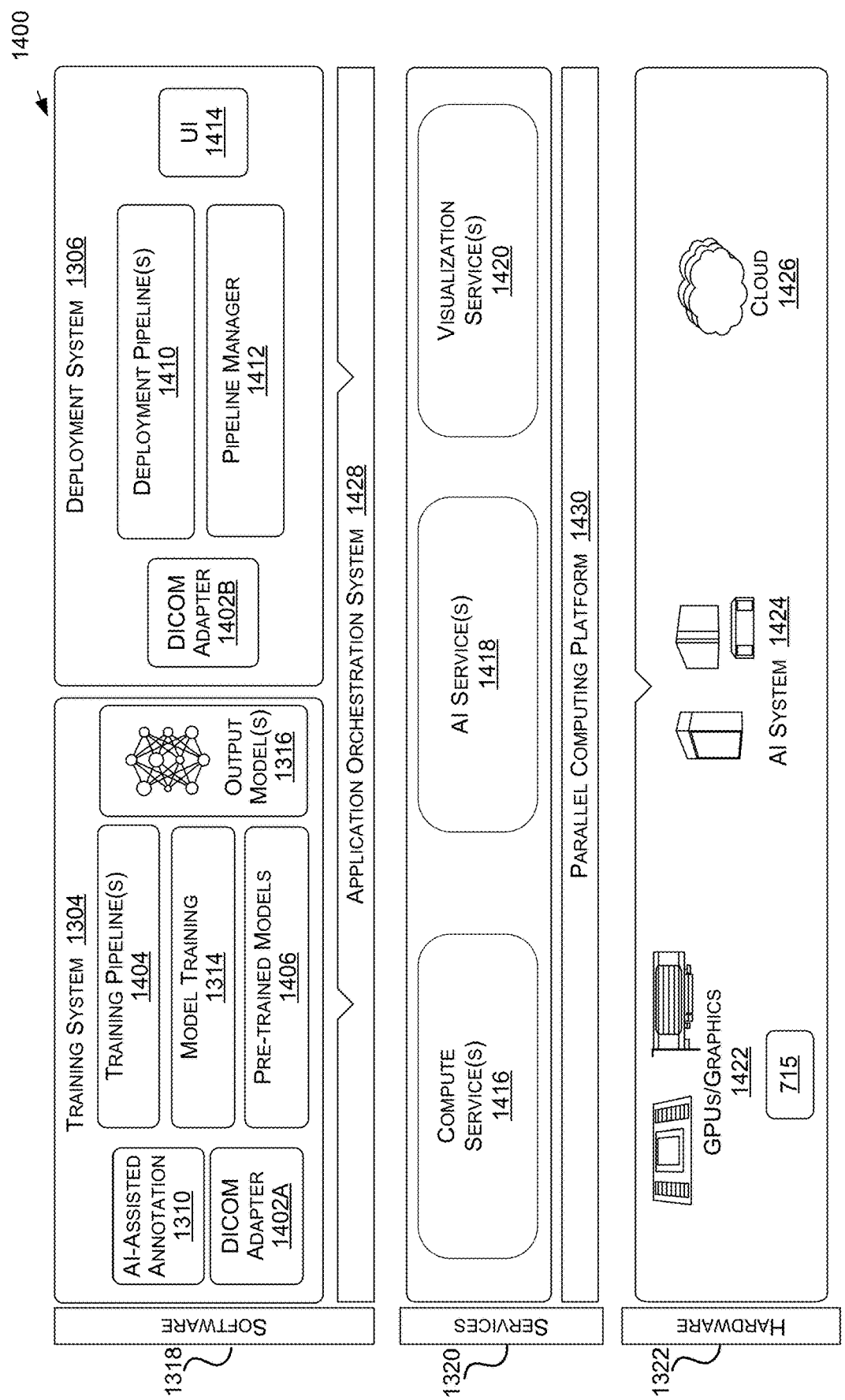
FIG. 14 is a system diagram for an example system for training, adapting, instantiating and deploying machine learning models in an advanced computing pipeline, in accordance with at least one embodiment.

In at least one embodiment, developers may then share applications or containers through a network for access and use by users of a system (e.g., system 1400 of FIG. 14). In at least one embodiment, completed and validated applications or containers may be stored in a container registry and associated machine learning models may be stored in model registry 1324. In at least one embodiment, a requesting entity—who provides an inference or image processing request—may browse a container registry and/or model registry 1324 for an application, container, dataset, machine learning model, etc., select a desired combination of elements for inclusion in data processing pipeline, and submit an imaging processing request. In at least one embodiment, a request may include input data (and associated patient data, in some examples) that is necessary to perform a request, and/or may include a selection of application(s) and/or machine learning models to be executed in processing a request. In at least one embodiment, a request may then be passed to one or more components of deployment system 1306 (e.g., a cloud) to perform processing of data processing pipeline. In at least one embodiment, processing by deployment system 1306 may include referencing selected elements (e.g., applications, containers, models, etc.) from a container registry and/or model registry 1324. In at least one embodiment, once results are generated by a pipeline, results may be returned to a user for reference (e.g., for viewing in a viewing application suite executing on a local, on-premises workstation or terminal).

In at least one embodiment, to aid in processing or execution of applications or containers in pipelines, services 1320 may be leveraged. In at least one embodiment, services 1320 may include compute services, artificial intelligence (AI) services, visualization services, and/or other service types. In at least one embodiment, services 1320 may provide functionality that is common to one or more applications in software 1318, so functionality may be abstracted to a service that may be called upon or leveraged by applications. In at least one embodiment, functionality provided by services 1320 may run dynamically and more efficiently, while also scaling well by allowing applications to process data in parallel (e.g., using a parallel computing platform 1430 (FIG. 14)). In at least one embodiment, rather than each application that shares a same functionality offered by a service 1320 being required to have a respective instance of service 1320, service 1320 may be shared between and among various applications. In at least one embodiment, services may include an inference server or engine that may be used for executing detection or segmentation tasks, as non-limiting examples. In at least one embodiment, a model training service may be included that may provide machine learning model training and/or retraining capabilities. In at least one embodiment, a data augmentation service may further be included that may provide GPU accelerated data (e.g., DICOM, RIS, CIS, REST compliant, RPC, raw, etc.) extraction, resizing, scaling, and/or other augmentation. In at least one embodiment, a visualization service may be used that may add image rendering effects effects—such as ray-tracing, rasterization, denoising, sharpening, etc.—to add realism to two-dimensional (2D) and/or three-dimensional (3D) models. In at least one embodiment, virtual instrument services may be included that provide for beam-forming, segmentation, inferencing, imaging, and/or support for other applications within pipelines of virtual instruments.

In at least one embodiment, where a service 1320 includes an AI service (e.g., an inference service), one or more machine learning models may be executed by calling upon (e.g., as an API call) an inference service (e.g., an inference server) to execute machine learning model(s), or processing thereof, as part of application execution. In at least one embodiment, where another application includes one or more machine learning models for segmentation tasks, an application may call upon an inference service to execute machine learning models for performing one or more of processing operations associated with segmentation tasks. In at least one embodiment, software 1318 implementing advanced processing and inferencing pipeline that includes segmentation application and anomaly detection application may be streamlined because each application may call upon a same inference service to perform one or more inferencing tasks.

In at least one embodiment, hardware 1322 may include GPUs, CPUs, graphics cards, an AI/deep learning system (e.g., an AI supercomputer, such as NVIDIA's DGX), a cloud platform, or a combination thereof. In at least one embodiment, different types of hardware 1322 may be used to provide efficient, purpose-built support for software 1318 and services 1320 in deployment system 1306. In at least one embodiment, use of GPU processing may be implemented for processing locally (e.g., at facility 1302), within an AI/deep learning system, in a cloud system, and/or in other processing components of deployment system 1306 to improve efficiency, accuracy, and efficacy of image processing and generation. In at least one embodiment, software 1318 and/or services 1320 may be optimized for GPU processing with respect to deep learning, machine learning, and/or high-performance computing, as non-limiting examples. In at least one embodiment, at least some of computing environment of deployment system 1306 and/or training system 1304 may be executed in a datacenter one or more supercomputers or high performance computing systems, with GPU optimized software (e.g., hardware and software combination of NVIDIA's DGX System). In at least one embodiment, hardware 1322 may include any number of GPUs that may be called upon to perform processing of data in parallel, as described herein. In at least one embodiment, cloud platform may further include GPU processing for GPU-optimized execution of deep learning tasks, machine learning tasks, or other computing tasks. In at least one embodiment, cloud platform (e.g., NVIDIA's NGC) may be executed using an AI/deep learning supercomputer(s) and/or GPU-optimized software (e.g., as provided on NVIDIA's DGX Systems) as a hardware abstraction and scaling platform. In at least one embodiment, cloud platform may integrate an application container clustering system or orchestration system (e.g., KUBERNETES) on multiple GPUs to enable seamless scaling and load balancing.

FIG. 14 is a system diagram for an example system 1400 for generating and deploying an imaging deployment pipeline, in accordance with at least one embodiment. In at least one embodiment, system 1400 may be used to implement process 1300 of FIG. 13 and/or other processes including advanced processing and inferencing pipelines. In at least one embodiment, system 1400 may include training system 1304 and deployment system 1306. In at least one embodiment, training system 1304 and deployment system 1306 may be implemented using software 1318, services 1320, and/or hardware 1322, as described herein.

In at least one embodiment, system 1400 (e.g., training system 1304 and/or deployment system 1306) may implemented in a cloud computing environment (e.g., using cloud 1426). In at least one embodiment, system 1400 may be implemented locally with respect to a healthcare services facility, or as a combination of both cloud and local computing resources. In at least one embodiment, access to APIs in cloud 1426 may be restricted to authorized users through enacted security measures or protocols. In at least one embodiment, a security protocol may include web tokens that may be signed by an authentication (e.g., AuthN, AuthZ, Gluecon, etc.) service and may carry appropriate authorization. In at least one embodiment, APIs of virtual instruments (described herein), or other instantiations of system 1400, may be restricted to a set of public IPs that have been vetted or authorized for interaction.

In at least one embodiment, various components of system 1400 may communicate between and among one another using any of a variety of different network types, including but not limited to local area networks (LANs) and/or wide area networks (WANs) via wired and/or wireless communication protocols. In at least one embodiment, communication between facilities and components of system 1400 (e.g., for transmitting inference requests, for receiving results of inference requests, etc.) may be communicated over data bus(ses), wireless data protocols (Wi-Fi), wired data protocols (e.g., Ethernet), etc.

In at least one embodiment, training system 1304 may execute training pipelines 1404, similar to those described herein with respect to FIG. 13. In at least one embodiment, where one or more machine learning models are to be used in deployment pipelines 1410 by deployment system 1306, training pipelines 1404 may be used to train or retrain one or more (e.g. pre-trained) models, and/or implement one or more of pre-trained models 1406 (e.g., without a need for retraining or updating). In at least one embodiment, as a result of training pipelines 1404, output model(s) 1316 may be generated. In at least one embodiment, training pipelines 1404 may include any number of processing steps, such as but not limited to imaging data (or other input data) conversion or adaption In at least one embodiment, for different machine learning models used by deployment system 1306, different training pipelines 1404 may be used. In at least one embodiment, training pipeline 1404 similar to a first example described with respect to FIG. 13 may be used for a first machine learning model, training pipeline 1404 similar to a second example described with respect to FIG. 13 may be used for a second machine learning model, and training pipeline 1404 similar to a third example described with respect to FIG. 13 may be used for a third machine learning model. In at least one embodiment, any combination of tasks within training system 1304 may be used depending on what is required for each respective machine learning model. In at least one embodiment, one or more of machine learning models may already be trained and ready for deployment so machine learning models may not undergo any processing by training system 1304, and may be implemented by deployment system 1306.

In at least one embodiment, output model(s) 1316 and/or pre-trained model(s) 1406 may include any types of machine learning models depending on implementation or embodiment. In at least one embodiment, and without limitation, machine learning models used by system 1400 may include machine learning model(s) using linear regression, logistic regression, decision trees, support vector machines (SVM), Naïve Bayes, k-nearest neighbor (Knn), K means clustering, random forest, dimensionality reduction algorithms, gradient boosting algorithms, neural networks (e.g., auto-encoders, convolutional, recurrent, perceptrons, Long/Short Term Memory (LSTM), Hopfield, Boltzmann, deep belief, deconvolutional, generative adversarial, liquid state machine, etc.), and/or other types of machine learning models.

Figure 15A:
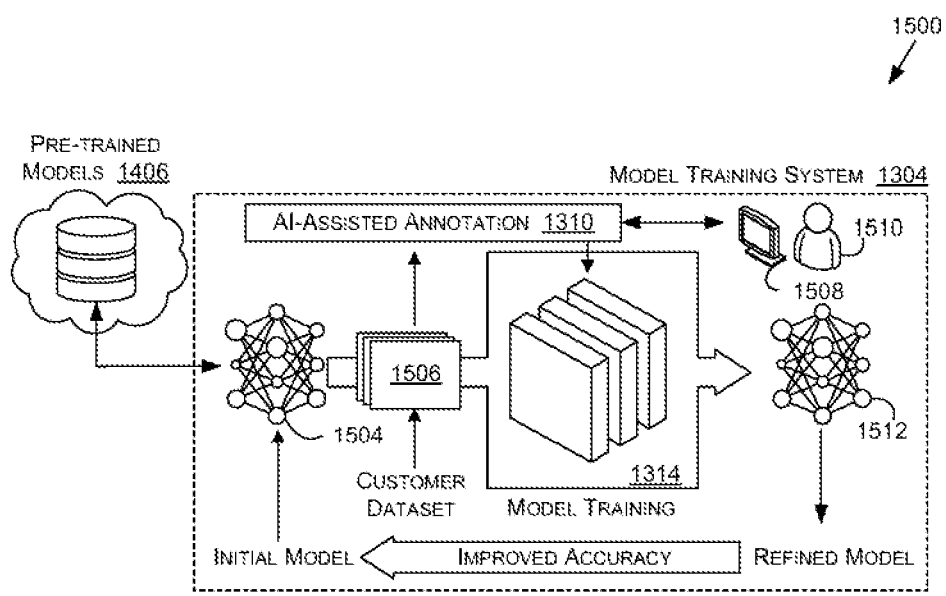
FIGS. 15A and 15B illustrate a data flow diagram for a process to train a machine learning model, as well as client-server architecture to enhance annotation tools with pre-trained annotation models, in accordance with at least one embodiment.
Figure 15B:
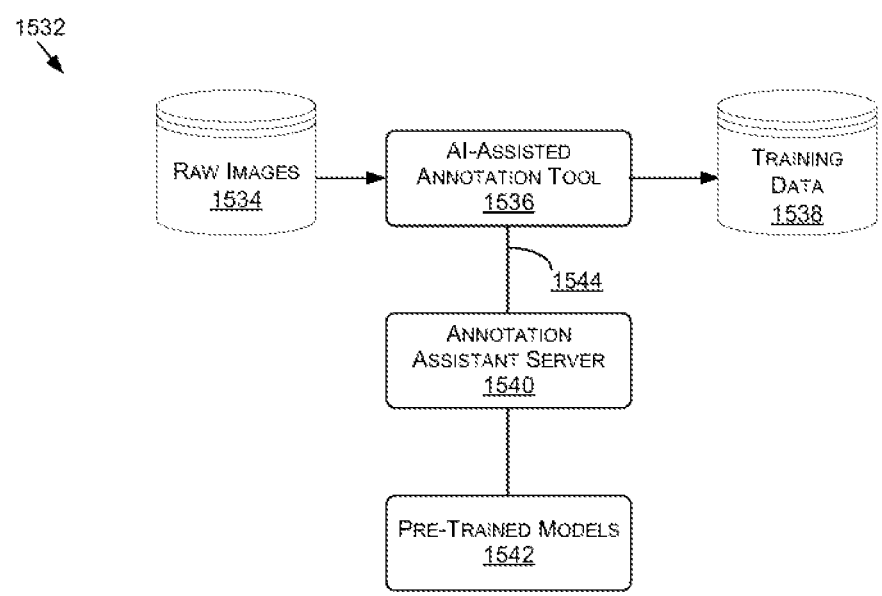

In at least one embodiment, training pipelines 1404 may include AI-assisted annotation, as described in more detail herein with respect to at least FIG. 15B. In at least one embodiment, labeled data 1312 (e.g., traditional annotation) may be generated by any number of techniques. In at least one embodiment, labels or other annotations may be generated within a drawing program (e.g., an annotation program), a computer aided design (CAD) program, a labeling program, another type of program suitable for generating annotations or labels for ground truth, and/or may be hand drawn, in some examples. In at least one embodiment, ground truth data may be synthetically produced (e.g., generated from computer models or renderings), real produced (e.g., designed and produced from real-world data), machine-automated (e.g., using feature analysis and learning to extract features from data and then generate labels), human annotated (e.g., labeler, or annotation expert, defines location of labels), and/or a combination thereof. In at least one embodiment, for each instance of imaging data 1308 (or other data type used by machine learning models), there may be corresponding ground truth data generated by training system 1304. In at least one embodiment, AI-assisted annotation may be performed as part of deployment pipelines 1410; either in addition to, or in lieu of AI-assisted annotation included in training pipelines 1404. In at least one embodiment, system 1400 may include a multi-layer platform that may include a software layer (e.g., software 1318) of diagnostic applications (or other application types) that may perform one or more medical imaging and diagnostic functions. In at least one embodiment, system 1400 may be communicatively coupled to (e.g., via encrypted links) PACS server networks of one or more facilities. In at least one embodiment, system 1400 may be configured to access and referenced data from PACS servers to perform operations, such as training machine learning models, deploying machine learning models, image processing, inferencing, and/or other operations.

In at least one embodiment, a software layer may be implemented as a secure, encrypted, and/or authenticated API through which applications or containers may be invoked (e.g., called) from an external environment(s) (e.g., facility 1302). In at least one embodiment, applications may then call or execute one or more services 1320 for performing compute, AI, or visualization tasks associated with respective applications, and software 1318 and/or services 1320 may leverage hardware 1322 to perform processing tasks in an effective and efficient manner.

In at least one embodiment, deployment system 1306 may execute deployment pipelines 1410. In at least one embodiment, deployment pipelines 1410 may include any number of applications that may be sequentially, non-sequentially, or otherwise applied to imaging data (and/or other data types) generated by imaging devices, sequencing devices, genomics devices, etc.—including AI-assisted annotation, as described above. In at least one embodiment, as described herein, a deployment pipeline 1410 for an individual device may be referred to as a virtual instrument for a device (e.g., a virtual ultrasound instrument, a virtual CT scan instrument, a virtual sequencing instrument, etc.). In at least one embodiment, for a single device, there may be more than one deployment pipeline 1410 depending on information desired from data generated by a device. In at least one embodiment, where detections of anomalies are desired from an MRI machine, there may be a first deployment pipeline 1410, and where image enhancement is desired from output of an MRI machine, there may be a second deployment pipeline 1410.

In at least one embodiment, an image generation application may include a processing task that includes use of a machine learning model. In at least one embodiment, a user may desire to use their own machine learning model, or to select a machine learning model from model registry 1324. In at least one embodiment, a user may implement their own machine learning model or select a machine learning model for inclusion in an application for performing a processing task. In at least one embodiment, applications may be selectable and customizable, and by defining constructs of applications, deployment and implementation of applications for a particular user are presented as a more seamless user experience. In at least one embodiment, by leveraging other features of system 1400—such as services 1320 and hardware 1322—deployment pipelines 1410 may be even more user friendly, provide for easier integration, and produce more accurate, efficient, and timely results.

In at least one embodiment, deployment system 1306 may include a user interface 1414 (e.g., a graphical user interface, a web interface, etc.) that may be used to select applications for inclusion in deployment pipeline(s) 1410, arrange applications, modify or change applications or parameters or constructs thereof, use and interact with deployment pipeline(s) 1410 during set-up and/or deployment, and/or to otherwise interact with deployment system 1306. In at least one embodiment, although not illustrated with respect to training system 1304, user interface 1414 (or a different user interface) may be used for selecting models for use in deployment system 1306, for selecting models for training, or retraining, in training system 1304, and/or for otherwise interacting with training system 1304.

In at least one embodiment, pipeline manager 1412 may be used, in addition to an application orchestration system 1428, to manage interaction between applications or containers of deployment pipeline(s) 1410 and services 1320 and/or hardware 1322. In at least one embodiment, pipeline manager 1412 may be configured to facilitate interactions from application to application, from application to service 1320, and/or from application or service to hardware 1322. In at least one embodiment, although illustrated as included in software 1318, this is not intended to be limiting, and in some examples (e.g., as illustrated in FIG. 12cc) pipeline manager 1412 may be included in services 1320. In at least one embodiment, application orchestration system 1428 (e.g., Kubernetes, DOCKER, etc.) may include a container orchestration system that may group applications into containers as logical units for coordination, management, scaling, and deployment. In at least one embodiment, by associating applications from deployment pipeline(s) 1410 (e.g., a reconstruction application, a segmentation application, etc.) with individual containers, each application may execute in a self-contained environment (e.g., at a kernel level) to increase speed and efficiency.

In at least one embodiment, each application and/or container (or image thereof) may be individually developed, modified, and deployed (e.g., a first user or developer may develop, modify, and deploy a first application and a second user or developer may develop, modify, and deploy a second application separate from a first user or developer), which may allow for focus on, and attention to, a task of a single application and/or container(s) without being hindered by tasks of another application(s) or container(s). In at least one embodiment, communication, and cooperation between different containers or applications may be aided by pipeline manager 1412 and application orchestration system 1428. In at least one embodiment, so long as an expected input and/or output of each container or application is known by a system (e.g., based on constructs of applications or containers), application orchestration system 1428 and/or pipeline manager 1412 may facilitate communication among and between, and sharing of resources among and between, each of applications or containers. In at least one embodiment, because one or more of applications or containers in deployment pipeline(s) 1410 may share same services and resources, application orchestration system 1428 may orchestrate, load balance, and determine sharing of services or resources between and among various applications or containers. In at least one embodiment, a scheduler may be used to track resource requirements of applications or containers, current usage or planned usage of these resources, and resource availability. In at least one embodiment, a scheduler may thus allocate resources to different applications and distribute resources between and among applications in view of requirements and availability of a system. In some examples, a scheduler (and/or other component of application orchestration system 1428) may determine resource availability and distribution based on constraints imposed on a system (e.g., user constraints), such as quality of service (QoS), urgency of need for data outputs (e.g., to determine whether to execute real-time processing or delayed processing), etc.

In at least one embodiment, services 1320 leveraged by and shared by applications or containers in deployment system 1306 may include compute services 1416, AI services 1418, visualization services 1420, and/or other service types. In at least one embodiment, applications may call (e.g., execute) one or more of services 1320 to perform processing operations for an application. In at least one embodiment, compute services 1416 may be leveraged by applications to perform super-computing or other high-performance computing (HPC) tasks. In at least one embodiment, compute service(s) 1416 may be leveraged to perform parallel processing (e.g., using a parallel computing platform 1430) for processing data through one or more of applications and/or one or more tasks of a single application, substantially simultaneously. In at least one embodiment, parallel computing platform 1430 (e.g., NVIDIA's CUDA) may enable general purpose computing on GPUs (GPGPU) (e.g., GPUs 1422). In at least one embodiment, a software layer of parallel computing platform 1430 may provide access to virtual instruction sets and parallel computational elements of GPUs, for execution of compute kernels. In at least one embodiment, parallel computing platform 1430 may include memory and, in some embodiments, a memory may be shared between and among multiple containers, and/or between and among different processing tasks within a single container. In at least one embodiment, inter-process communication (IPC) calls may be generated for multiple containers and/or for multiple processes within a container to use same data from a shared segment of memory of parallel computing platform 1430 (e.g., where multiple different stages of an application or multiple applications are processing same information). In at least one embodiment, rather than making a copy of data and moving data to different locations in memory (e.g., a read/write operation), same data in same location of a memory may be used for any number of processing tasks (e.g., at a same time, at different times, etc.). In at least one embodiment, as data is used to generate new data as a result of processing, this information of a new location of data may be stored and shared between various applications. In at least one embodiment, location of data and a location of updated or modified data may be part of a definition of how a payload is understood within containers.

In at least one embodiment, AI services 1418 may be leveraged to perform inferencing services for executing machine learning model(s) associated with applications (e.g., tasked with performing one or more processing tasks of an application). In at least one embodiment, AI services 1418 may leverage AI system 1424 to execute machine learning model(s) (e.g., neural networks, such as CNNs) for segmentation, reconstruction, object detection, feature detection, classification, and/or other inferencing tasks. In at least one embodiment, applications of deployment pipeline(s) 1410 may use one or more of output models 1316 from training system 1304 and/or other models of applications to perform inference on imaging data. In at least one embodiment, two or more examples of inferencing using application orchestration system 1428 (e.g., a scheduler) may be available. In at least one embodiment, a first category may include a high priority/low latency path that may achieve higher service level agreements, such as for performing inference on urgent requests during an emergency, or for a radiologist during diagnosis. In at least one embodiment, a second category may include a standard priority path that may be used for requests that may be non-urgent or where analysis may be performed at a later time. In at least one embodiment, application orchestration system 1428 may distribute resources (e.g., services 1320 and/or hardware 1322) based on priority paths for different inferencing tasks of AI services 1418.

In at least one embodiment, shared storage may be mounted to AI services 1418 within system 1400. In at least one embodiment, shared storage may operate as a cache (or other storage device type) and may be used to process inference requests from applications. In at least one embodiment, when an inference request is submitted, a request may be received by a set of API instances of deployment system 1306, and one or more instances may be selected (e.g., for best fit, for load balancing, etc.) to process a request. In at least one embodiment, to process a request, a request may be entered into a database, a machine learning model may be located from model registry 1324 if not already in a cache, a validation step may ensure appropriate machine learning model is loaded into a cache (e.g., shared storage), and/or a copy of a model may be saved to a cache. In at least one embodiment, a scheduler (e.g., of pipeline manager 1412) may be used to launch an application that is referenced in a request if an application is not already running or if there are not enough instances of an application. In at least one embodiment, if an inference server is not already launched to execute a model, an inference server may be launched. Any number of inference servers may be launched per model. In at least one embodiment, in a pull model, in which inference servers are clustered, models may be cached whenever load balancing is advantageous. In at least one embodiment, inference servers may be statically loaded in corresponding, distributed servers.

In at least one embodiment, inferencing may be performed using an inference server that runs in a container. In at least one embodiment, an instance of an inference server may be associated with a model (and optionally a plurality of versions of a model). In at least one embodiment, if an instance of an inference server does not exist when a request to perform inference on a model is received, a new instance may be loaded. In at least one embodiment, when starting an inference server, a model may be passed to an inference server such that a same container may be used to serve different models so long as inference server is running as a different instance.

In at least one embodiment, during application execution, an inference request for a given application may be received, and a container (e.g., hosting an instance of an inference server) may be loaded (if not already), and a start procedure may be called. In at least one embodiment, pre-processing logic in a container may load, decode, and/or perform any additional pre-processing on incoming data (e.g., using a CPU(s) and/or GPU(s)). In at least one embodiment, once data is prepared for inference, a container may perform inference as necessary on data. In at least one embodiment, this may include a single inference call on one image (e.g., a hand X-ray), or may require inference on hundreds of images (e.g., a chest CT). In at least one embodiment, an application may summarize results before completing, which may include, without limitation, a single confidence score, pixel level-segmentation, voxel-level segmentation, generating a visualization, or generating text to summarize findings. In at least one embodiment, different models or applications may be assigned different priorities. For example, some models may have a real-time (TAT<1 min) priority while others may have lower priority (e.g., TAT<10 min). In at least one embodiment, model execution times may be measured from requesting institution or entity and may include partner network traversal time, as well as execution on an inference service.

In at least one embodiment, transfer of requests between services 1320 and inference applications may be hidden behind a software development kit (SDK), and robust transport may be provide through a queue. In at least one embodiment, a request will be placed in a queue via an API for an individual application/tenant ID combination and an SDK will pull a request from a queue and give a request to an application. In at least one embodiment, a name of a queue may be provided in an environment from where an SDK will pick it up. In at least one embodiment, asynchronous communication through a queue may be useful as it may allow any instance of an application to pick up work as it becomes available. Results may be transferred back through a queue, to ensure no data is lost. In at least one embodiment, queues may also provide an ability to segment work, as highest priority work may go to a queue with most instances of an application connected to it, while lowest priority work may go to a queue with a single instance connected to it that processes tasks in an order received. In at least one embodiment, an application may run on a GPU-accelerated instance generated in cloud 1426, and an inference service may perform inferencing on a GPU.

In at least one embodiment, visualization services 1420 may be leveraged to generate visualizations for viewing outputs of applications and/or deployment pipeline(s) 1410. In at least one embodiment, GPUs 1422 may be leveraged by visualization services 1420 to generate visualizations. In at least one embodiment, rendering effects, such as ray-tracing, may be implemented by visualization services 1420 to generate higher quality visualizations. In at least one embodiment, visualizations may include, without limitation, 2D image renderings, 3D volume renderings, 3D volume reconstruction, 2D tomographic slices, virtual reality displays, augmented reality displays, etc. In at least one embodiment, virtualized environments may be used to generate a virtual interactive display or environment (e.g., a virtual environment) for interaction by users of a system (e.g., doctors, nurses, radiologists, etc.). In at least one embodiment, visualization services 1420 may include an internal visualizer, cinematics, and/or other rendering or image processing capabilities or functionality (e.g., ray tracing, rasterization, internal optics, etc.).

In at least one embodiment, hardware 1322 may include GPUs 1422, AI system 1424, cloud 1426, and/or any other hardware used for executing training system 1304 and/or deployment system 1306. In at least one embodiment, GPUs 1422 (e.g., NVIDIA's TESLA and/or QUADRO GPUs) may include any number of GPUs that may be used for executing processing tasks of compute services 1416, AI services 1418, visualization services 1420, other services, and/or any of features or functionality of software 1318. For example, with respect to AI services 1418, GPUs 1422 may be used to perform pre-processing on imaging data (or other data types used by machine learning models), post-processing on outputs of machine learning models, and/or to perform inferencing (e.g., to execute machine learning models). In at least one embodiment, cloud 1426, AI system 1424, and/or other components of system 1400 may use GPUs 1422. In at least one embodiment, cloud 1426 may include a GPU-optimized platform for deep learning tasks. In at least one embodiment, AI system 1424 may use GPUs, and cloud 1426—or at least a portion tasked with deep learning or inferencing—may be executed using one or more AI systems 1424. As such, although hardware 1322 is illustrated as discrete components, this is not intended to be limiting, and any components of hardware 1322 may be combined with, or leveraged by, any other components of hardware 1322.

In at least one embodiment, AI system 1424 may include a purpose-built computing system (e.g., a super-computer or an HPC) configured for inferencing, deep learning, machine learning, and/or other artificial intelligence tasks. In at least one embodiment, AI system 1424 (e.g., NVIDIA's DGX) may include GPU-optimized software (e.g., a software stack) that may be executed using a plurality of GPUs 1422, in addition to CPUs, RAM, storage, and/or other components, features, or functionality. In at least one embodiment, one or more AI systems 1424 may be implemented in cloud 1426 (e.g., in a data center) for performing some or all of AI-based processing tasks of system 1400.

In at least one embodiment, cloud 1426 may include a GPU-accelerated infrastructure (e.g., NVIDIA's NGC) that may provide a GPU-optimized platform for executing processing tasks of system 1400. In at least one embodiment, cloud 1426 may include an AI system(s) 1424 for performing one or more of AI-based tasks of system 1400 (e.g., as a hardware abstraction and scaling platform). In at least one embodiment, cloud 1426 may integrate with application orchestration system 1428 leveraging multiple GPUs to enable seamless scaling and load balancing between and among applications and services 1320. In at least one embodiment, cloud 1426 may tasked with executing at least some of services 1320 of system 1400, including compute services 1416, AI services 1418, and/or visualization services 1420, as described herein. In at least one embodiment, cloud 1426 may perform small and large batch inference (e.g., executing NVIDIA's TENSOR RT), provide an accelerated parallel computing API and platform 1430 (e.g., NVIDIA's CUDA), execute application orchestration system 1428 (e.g., KUBERNETES), provide a graphics rendering API and platform (e.g., for ray-tracing, 2D graphics, 3D graphics, and/or other rendering techniques to produce higher quality cinematics), and/or may provide other functionality for system 1400.

FIG. 15A illustrates a data flow diagram for a process 1500 to train, retrain, or update a machine learning model, in accordance with at least one embodiment. In at least one embodiment, process 1500 may be executed using, as a non-limiting example, system 1400 of FIG. 14. In at least one embodiment, process 1500 may leverage services 1320 and/or hardware 1322 of system 1400, as described herein. In at least one embodiment, refined models 1512 generated by process 1500 may be executed by deployment system 1306 for one or more containerized applications in deployment pipelines 1410.

In at least one embodiment, model training 1314 may include retraining or updating an initial model 1504 (e.g., a pre-trained model) using new training data (e.g., new input data, such as customer dataset 1506, and/or new ground truth data associated with input data). In at least one embodiment, to retrain, or update, initial model 1504, output or loss layer(s) of initial model 1504 may be reset, or deleted, and/or replaced with an updated or new output or loss layer(s). In at least one embodiment, initial model 1504 may have previously fine-tuned parameters (e.g., weights and/or biases) that remain from prior training, so training or retraining 1314 may not take as long or require as much processing as training a model from scratch. In at least one embodiment, during model training 1314, by having reset or replaced output or loss layer(s) of initial model 1504, parameters may be updated and re-tuned for a new data set based on loss calculations associated with accuracy of output or loss layer(s) at generating predictions on new, customer dataset 1506 (e.g., image data 1308 of FIG. 13).

In at least one embodiment, pre-trained models 1406 may be stored in a data store, or registry (e.g., model registry 1324 of FIG. 13). In at least one embodiment, pre-trained models 1406 may have been trained, at least in part, at one or more facilities other than a facility executing process 1500. In at least one embodiment, to protect privacy and rights of patients, subjects, or clients of different facilities, pre-trained models 1406 may have been trained, on-premise, using customer or patient data generated on-premise. In at least one embodiment, pre-trained models 1406 may be trained using cloud 1426 and/or other hardware 1322, but confidential, privacy protected patient data may not be transferred to, used by, or accessible to any components of cloud 1426 (or other off premise hardware). In at least one embodiment, where a pre-trained model 1406 is trained at using patient data from more than one facility, pre-trained model 1406 may have been individually trained for each facility prior to being trained on patient or customer data from another facility. In at least one embodiment, such as where a customer or patient data has been released of privacy concerns (e.g., by waiver, for experimental use, etc.), or where a customer or patient data is included in a public data set, a customer or patient data from any number of facilities may be used to train pre-trained model 1406 on-premise and/or off premise, such as in a datacenter or other cloud computing infrastructure.

In at least one embodiment, when selecting applications for use in deployment pipelines 1410, a user may also select machine learning models to be used for specific applications. In at least one embodiment, a user may not have a model for use, so a user may select a pre-trained model 1406 to use with an application. In at least one embodiment, pre-trained model 1406 may not be optimized for generating accurate results on customer dataset 1506 of a facility of a user (e.g., based on patient diversity, demographics, types of medical imaging devices used, etc.). In at least one embodiment, prior to deploying pre-trained model 1406 into deployment pipeline 1410 for use with an application(s), pre-trained model 1406 may be updated, retrained, and/or fine-tuned for use at a respective facility.

In at least one embodiment, a user may select pre-trained model 1406 that is to be updated, retrained, and/or fine-tuned, and pre-trained model 1406 may be referred to as initial model 1504 for training system 1304 within process 1500. In at least one embodiment, customer dataset 1506 (e.g., imaging data, genomics data, sequencing data, or other data types generated by devices at a facility) may be used to perform model training 1314 (which may include, without limitation, transfer learning) on initial model 1504 to generate refined model 1512. In at least one embodiment, ground truth data corresponding to customer dataset 1506 may be generated by training system 1304. In at least one embodiment, ground truth data may be generated, at least in part, by clinicians, scientists, doctors, practitioners, at a facility (e.g., as labeled clinic data 1312 of FIG. 13).

In at least one embodiment, AI-assisted annotation 1310 may be used in some examples to generate ground truth data. In at least one embodiment, AI-assisted annotation 1310 (e.g., implemented using an AI-assisted annotation SDK) may leverage machine learning models (e.g., neural networks) to generate suggested or predicted ground truth data for a customer dataset. In at least one embodiment, user 1510 may use annotation tools within a user interface (a graphical user interface (GUI)) on computing device 1508.

In at least one embodiment, user 1510 may interact with a GUI via computing device 1508 to edit or fine-tune (auto)annotations. In at least one embodiment, a polygon editing feature may be used to move vertices of a polygon to more accurate or fine-tuned locations.

In at least one embodiment, once customer dataset 1506 has associated ground truth data, ground truth data (e.g., from AI-assisted annotation, manual labeling, etc.) may be used by during model training 1314 to generate refined model 1512. In at least one embodiment, customer dataset 1506 may be applied to initial model 1504 any number of times, and ground truth data may be used to update parameters of initial model 1504 until an acceptable level of accuracy is attained for refined model 1512. In at least one embodiment, once refined model 1512 is generated, refined model 1512 may be deployed within one or more deployment pipelines 1410 at a facility for performing one or more processing tasks with respect to medical imaging data.

In at least one embodiment, refined model 1512 may be uploaded to pre-trained models 1406 in model registry 1324 to be selected by another facility. In at least one embodiment, his process may be completed at any number of facilities such that refined model 1512 may be further refined on new datasets any number of times to generate a more universal model.

FIG. 15B is an example illustration of a client-server architecture 1532 to enhance annotation tools with pre-trained annotation models, in accordance with at least one embodiment. In at least one embodiment, AI-assisted annotation tools 1536 may be instantiated based on a client-server architecture 1532. In at least one embodiment, annotation tools 1536 in imaging applications may aid radiologists, for example, identify organs and abnormalities. In at least one embodiment, imaging applications may include software tools that help user 1510 to identify, as a non-limiting example, a few extreme points on a particular organ of interest in raw images 1534 (e.g., in a 3D MRI or CT scan) and receive auto-annotated results for all 2D slices of a particular organ. In at least one embodiment, results may be stored in a data store as training data 1538 and used as (for example and without limitation) ground truth data for training. In at least one embodiment, when computing device 1508 sends extreme points for AI-assisted annotation 1310, a deep learning model, for example, may receive this data as input and return inference results of a segmented organ or abnormality. In at least one embodiment, pre-instantiated annotation tools, such as AI-Assisted Annotation Tool 1536B in FIG. 15B, may be enhanced by making API calls (e.g., API Call 1544) to a server, such as an Annotation Assistant Server 1540 that may include a set of pre-trained models 1542 stored in an annotation model registry, for example. In at least one embodiment, an annotation model registry may store pre-trained models 1542 (e.g., machine learning models, such as deep learning models) that are pre-trained to perform AI-assisted annotation on a particular organ or abnormality. These models may be further updated by using training pipelines 1404. In at least one embodiment, pre-installed annotation tools may be improved over time as new labeled clinic data 1312 is added.

Such components can be used to composite constituent images into a single representation using parameters determined from one or more quality assessment values.

Automated Technology

Figure 16A:
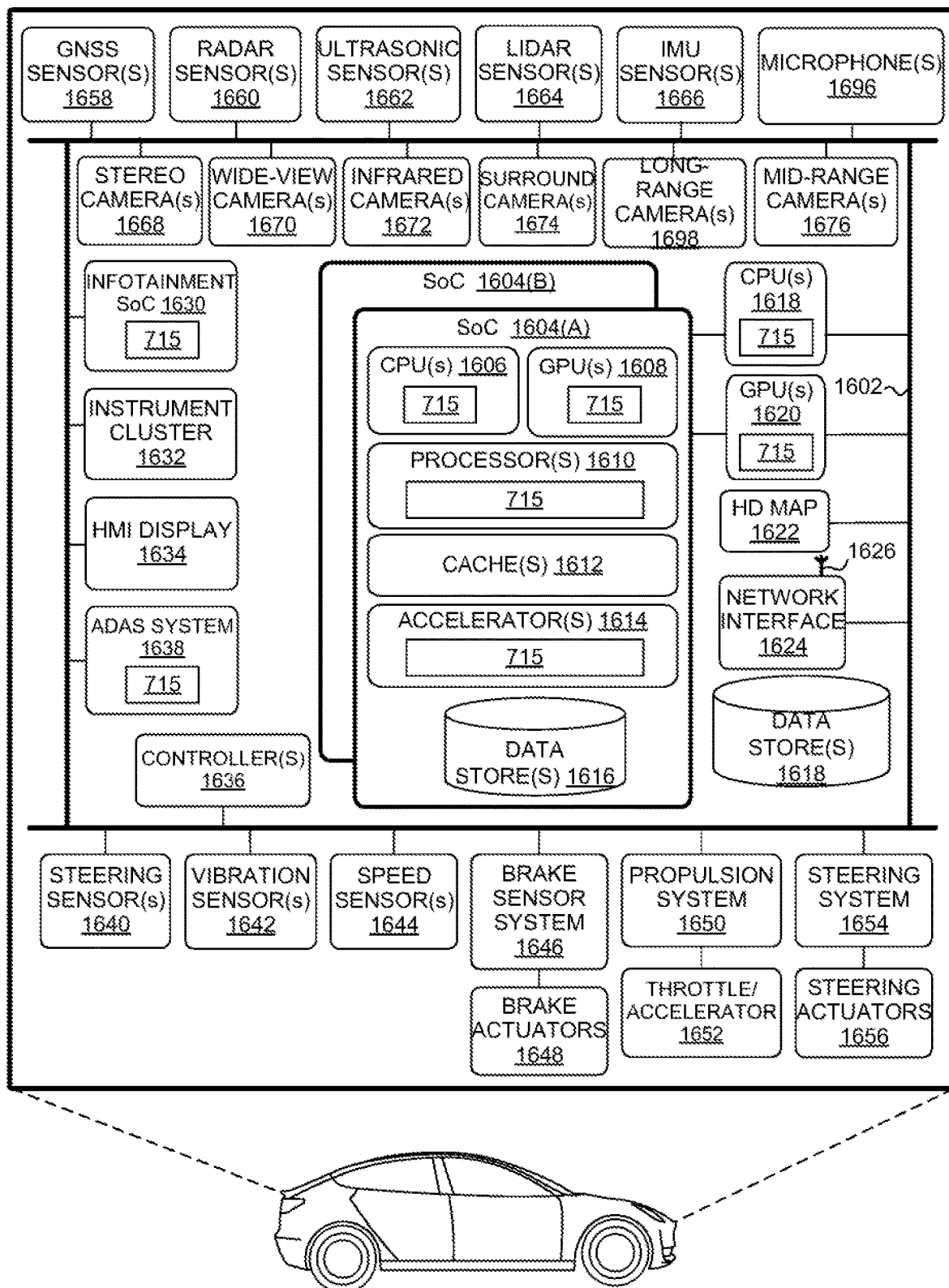
FIGS. 16A and 16B illustrate components that can be used with a vehicle system, in accordance with at least one embodiment.

FIG. 16A is a block diagram illustrating an example system architecture for autonomous vehicle 1600 of FIG. 16A, according to at least one embodiment. In at least one embodiment, each of components, features, and systems of vehicle 1600 in FIG. 16A are illustrated as being connected via a bus 1602. In at least one embodiment, bus 1602 may include, without limitation, a CAN data interface (alternatively referred to herein as a "CAN bus"). In at least one embodiment, a CAN bus may be a network inside vehicle 1600 used to aid in control of various features and functionality of vehicle 1600, such as actuation of brakes, acceleration, braking, steering, windshield wipers, etc. In at least one embodiment, bus 1602 may be configured to have dozens or even hundreds of nodes, each with its own unique identifier (e.g., a CAN ID). In at least one embodiment, bus 1602 may be read to find steering wheel angle, ground speed, engine revolutions per minute ("RPMs"), button positions, and/or other vehicle status indicators. In at least one embodiment, bus 1602 may be a CAN bus that is ASIL B compliant.

In at least one embodiment, in addition to, or alternatively from CAN, FlexRay and/or Ethernet may be used. In at least one embodiment, there may be any number of busses 1602, which may include, without limitation, zero or more CAN busses, zero or more FlexRay busses, zero or more Ethernet busses, and/or zero or more other types of busses using a different protocol. In at least one embodiment, two or more busses 1602 may be used to perform different functions, and/or may be used for redundancy. For example, a first bus 1602 may be used for collision avoidance functionality and a second bus 1602 may be used for actuation control. In at least one embodiment, each bus 1602 may communicate with any of components of vehicle 1600, and two or more busses 1602 may communicate with same components. In at least one embodiment, each of any number of system(s) on chip(s) ("SoC(s)") 1604, each of controller(s) 1636, and/or each computer within vehicle may have access to same input data (e.g., inputs from sensors of vehicle 1600), and may be connected to a common bus, such CAN bus.

In at least one embodiment, vehicle 1600 may include one or more controller(s) 1636, such as those described herein with respect to FIG. 1A. Controller(s) 1636 may be used for a variety of functions. In at least one embodiment, controller(s) 1636 may be coupled to any of various other components and systems of vehicle 1600, and may be used for control of vehicle 1600, artificial intelligence of vehicle 1600, infotainment for vehicle 1600, and/or like.

In at least one embodiment, vehicle 1600 may include any number of SoCs 1604. Each of SoCs 1604 may include, without limitation, central processing units ("CPU(s)") 1606, graphics processing units ("GPU(s)") 1608, processor(s) 1610, cache(s) 1612, accelerator(s) 1614, data store(s) 1616, and/or other components and features not illustrated. In at least one embodiment, SoC(s) 1604 may be used to control vehicle 1600 in a variety of platforms and systems. For example, in at least one embodiment, SoC(s) 1604 may be combined in a system (e.g., system of vehicle 1600) with a High Definition ("HD") map 1622 which may obtain map refreshes and/or updates via network interface 1624 from one or more servers (not shown in FIG. 16A).

In at least one embodiment, CPU(s) 1606 may include a CPU cluster or CPU complex (alternatively referred to herein as a "CCPLEX"). In at least one embodiment, CPU(s) 1606 may include multiple cores and/or level two ("L2") caches. For instance, in at least one embodiment, CPU(s) 1606 may include eight cores in a coherent multi-processor configuration. In at least one embodiment, CPU(s) 1606 may include four dual-core clusters where each cluster has a dedicated L2 cache (e.g., a 2 MB L2 cache). In at least one embodiment, CPU(s) 1606 (e.g., CCPLEX) may be configured to support simultaneous cluster operation enabling any combination of clusters of CPU(s) 1606 to be active at any given time.

In at least one embodiment, one or more of CPU(s) 1606 may implement power management capabilities that include, without limitation, one or more of following features: individual hardware blocks may be clock-gated automatically when idle to save dynamic power; each core clock may be gated when core is not actively executing instructions due to execution of Wait for Interrupt ("WFI")/Wait for Event ("WFE") instructions; each core may be independently power-gated; each core cluster may be independently clock-gated when all cores are clock-gated or power-gated; and/or each core cluster may be independently power-gated when all cores are power-gated. In at least one embodiment, CPU(s) 1606 may further implement an enhanced algorithm for managing power states, where allowed power states and expected wakeup times are specified, and hardware/microcode determines best power state to enter for core, cluster, and CCPLEX. In at least one embodiment, processing cores may support simplified power state entry sequences in software with work offloaded to microcode.

In at least one embodiment, GPU(s) 1608 may include an integrated GPU (alternatively referred to herein as an "iGPU"). In at least one embodiment, GPU(s) 1608 may be programmable and may be efficient for parallel workloads. In at least one embodiment, GPU(s) 1608, in at least one embodiment, may use an enhanced tensor instruction set. In at least one embodiment, GPU(s) 1608 may include one or more streaming microprocessors, where each streaming microprocessor may include a level one ("L1") cache (e.g., an L1 cache with at least 96 KB storage capacity), and two or more of streaming microprocessors may share an L2 cache (e.g., an L2 cache with a 512 KB storage capacity). In at least one embodiment, GPU(s) 1608 may include at least eight streaming microprocessors. In at least one embodiment, GPU(s) 1608 may use compute application programming interface(s) (API(s)). In at least one embodiment, GPU(s) 1608 may use one or more parallel computing platforms and/or programming models (e.g., NVIDIA's CUDA).

In at least one embodiment, one or more of GPU(s) 1608 may be power-optimized for best performance in automotive and embedded use cases. For example, in on embodiment, GPU(s) 1608 could be fabricated on a Fin field-effect transistor ("FinFET"). In at least one embodiment, each streaming microprocessor may incorporate a number of mixed-precision processing cores partitioned into multiple blocks. For example, and without limitation, 64 PF32 cores and 32 PF64 cores could be partitioned into four processing blocks. In at least one embodiment, each processing block could be allocated 16 FP32 cores, 8 FP64 cores, 16 INT32 cores, two mixed-precision NVIDIA TENSOR COREs for deep learning matrix arithmetic, a level zero ("L0") instruction cache, a warp scheduler, a dispatch unit, and/or a 64 KB register file. In at least one embodiment, streaming microprocessors may include independent parallel integer and floating-point data paths to provide for efficient execution of workloads with a mix of computation and addressing calculations. In at least one embodiment, streaming microprocessors may include independent thread scheduling capability to enable finer-grain synchronization and cooperation between parallel threads. In at least one embodiment, streaming microprocessors may include a combined L1 data cache and shared memory unit in order to improve performance while simplifying programming.

In at least one embodiment, one or more of GPU(s) 1608 may include a high bandwidth memory ("HBM") and/or a 16 GB HBM2 memory subsystem to provide, in some examples, about 900 GB/second peak memory bandwidth. In at least one embodiment, in addition to, or alternatively from, HBM memory, a synchronous graphics random-access memory ("SGRAM") may be used, such as a graphics double data rate type five synchronous random-access memory ("GDDR5").

In at least one embodiment, GPU(s) 1608 may include unified memory technology. In at least one embodiment, address translation services ("ATS") support may be used to allow GPU(s) 1608 to access CPU(s) 1606 page tables directly. In at least one embodiment, embodiment, when GPU(s) 1608 memory management unit ("MMU") experiences a miss, an address translation request may be transmitted to CPU(s) 1606. In response, CPU(s) 1606 may look in its page tables for virtual-to-physical mapping for address and transmits translation back to GPU(s) 1608, in at least one embodiment. In at least one embodiment, unified memory technology may allow a single unified virtual address space for memory of both CPU(s) 1606 and GPU(s) 1608, thereby simplifying GPU(s) 1608 programming and porting of applications to GPU(s) 1608.

In at least one embodiment, GPU(s) 1608 may include any number of access counters that may keep track of frequency of access of GPU(s) 1608 to memory of other processors. In at least one embodiment, access counter(s) may help ensure that memory pages are moved to physical memory of processor that is accessing pages most frequently, thereby improving efficiency for memory ranges shared between processors.

In at least one embodiment, one or more of SoC(s) 1604 may include any number of cache(s) 1612, including those described herein. For example, in at least one embodiment, cache(s) 1612 could include a level three ("L3") cache that is available to both CPU(s) 1606 and GPU(s) 1608 (e.g., that is connected both CPU(s) 1606 and GPU(s) 1608). In at least one embodiment, cache(s) 1612 may include a write-back cache that may keep track of states of lines, such as by using a cache coherence protocol (e.g., MEI, MESI, MSI, etc.). In at least one embodiment, L3 cache may include 4 MB or more, depending on embodiment, although smaller cache sizes may be used.

In at least one embodiment, one or more of SoC(s) 1604 may include one or more accelerator(s) 1614 (e.g., hardware accelerators, software accelerators, or a combination thereof). In at least one embodiment, SoC(s) 1604 may include a hardware acceleration cluster that may include optimized hardware accelerators and/or large on-chip memory. In at least one embodiment, large on-chip memory (e.g., 4 MB of SRAM), may enable hardware acceleration cluster to accelerate neural networks and other calculations. In at least one embodiment, hardware acceleration cluster may be used to complement GPU(s) 1608 and to off-load some of tasks of GPU(s) 1608 (e.g., to free up more cycles of GPU(s) 1608 for performing other tasks). In at least one embodiment, accelerator(s) 1614 could be used for targeted workloads (e.g., perception, convolutional neural networks ("CNNs"), recurrent neural networks ("RNNs"), etc.) that are stable enough to be amenable to acceleration. In at least one embodiment, a CNN may include a region-based or regional convolutional neural networks ("RCNNs") and Fast RCNNs (e.g., as used for object detection) or other type of CNN.

In at least one embodiment, accelerator(s) 1614 (e.g., hardware acceleration cluster) may include a deep learning accelerator(s) ("DLA(s)"). DLA(s) may include, without limitation, one or more Tensor processing units ("TPU(s)") that may be configured to provide an additional ten trillion operations per second for deep learning applications and inferencing. In at least one embodiment, TPU(s) may be accelerators configured to, and optimized for, performing image processing functions (e.g., for CNNs, RCNNs, etc.). DLA(s) may further be optimized for a specific set of neural network types and floating point operations, as well as inferencing. In at least one embodiment, design of DLA(s) may provide more performance per millimeter than a typical general-purpose GPU, and typically vastly exceeds performance of a CPU. In at least one embodiment, TPU(s) may perform several functions, including a single-instance convolution function, supporting, for example, INT8, INT16, and FP16 data types for both features and weights, as well as post-processor functions. In at least one embodiment, DLA(s) may quickly and efficiently execute neural networks, especially CNNs, on processed or unprocessed data for any of a variety of functions, including, for example and without limitation: a CNN for object identification and detection using data from camera sensors; a CNN for distance estimation using data from camera sensors; a CNN for emergency vehicle detection and identification and detection using data from microphones 1696; a CNN for facial recognition and vehicle owner identification using data from camera sensors; and/or a CNN for security and/or safety related events.

In at least one embodiment, DLA(s) may perform any function of GPU(s) 1608, and by using an inference accelerator, for example, a designer may target either DLA(s) or GPU(s) 1608 for any function. For example, in at least one embodiment, designer may focus processing of CNNs and floating point operations on DLA(s) and leave other functions to GPU(s) 1608 and/or other accelerator(s) 1614.

In at least one embodiment, accelerator(s) 1614 (e.g., hardware acceleration cluster) may include a programmable vision accelerator(s) ("PVA"), which may alternatively be referred to herein as a computer vision accelerator. In at least one embodiment, PVA(s) may be designed and configured to accelerate computer vision algorithms for advanced driver assistance system ("ADAS") 1638, autonomous driving, augmented reality ("AR") applications, and/or virtual reality ("VR") applications. PVA(s) may provide a balance between performance and flexibility. For example, in at least one embodiment, each PVA(s) may include, for example and without limitation, any number of reduced instruction set computer ("RISC") cores, direct memory access ("DMA"), and/or any number of vector processors.

In at least one embodiment, RISC cores may interact with image sensors (e.g., image sensors of any of cameras described herein), image signal processor(s), and/or like. In at least one embodiment, each of RISC cores may include any amount of memory. In at least one embodiment, RISC cores may use any of a number of protocols, depending on embodiment. In at least one embodiment, RISC cores may execute a real-time operating system ("RTOS"). In at least one embodiment, RISC cores may be implemented using one or more integrated circuit devices, application specific integrated circuits ("ASICs"), and/or memory devices. For example, in at least one embodiment, RISC cores could include an instruction cache and/or a tightly coupled RAM.

In at least one embodiment, DMA may enable components of PVA(s) to access system memory independently of CPU(s) 1606. In at least one embodiment, DMA may support any number of features used to provide optimization to PVA including, but not limited to, supporting multi-dimensional addressing and/or circular addressing. In at least one embodiment, DMA may support up to six or more dimensions of addressing, which may include, without limitation, block width, block height, block depth, horizontal block stepping, vertical block stepping, and/or depth stepping.

In at least one embodiment, vector processors may be programmable processors that may be designed to efficiently and flexibly execute programming for computer vision algorithms and provide signal processing capabilities. In at least one embodiment, PVA may include a PVA core and two vector processing subsystem partitions. In at least one embodiment, PVA core may include a processor subsystem, DMA engine(s) (e.g., two DMA engines), and/or other peripherals. In at least one embodiment, vector processing subsystem may operate as primary processing engine of PVA, and may include a vector processing unit ("VPU"), an instruction cache, and/or vector memory (e.g., "VMEM"). In at least one embodiment, VPU may include a digital signal processor such as, for example, a single instruction, multiple data ("SIMD"), very long instruction word ("VLIW") digital signal processor. In at least one embodiment, a combination of SIMD and VLIW may enhance throughput and speed.

In at least one embodiment, each of vector processors may include an instruction cache and may be coupled to dedicated memory. As a result, in at least one embodiment, each of vector processors may be configured to execute independently of other vector processors. In at least one embodiment, vector processors that are included in a particular PVA may be configured to employ data parallelism. For instance, in at least one embodiment, plurality of vector processors included in a single PVA may execute same computer vision algorithm, but on different regions of an image. In at least one embodiment, vector processors included in a particular PVA may simultaneously execute different computer vision algorithms, on same image, or even execute different algorithms on sequential images or portions of an image. In at least one embodiment, among other things, any number of PVAs may be included in hardware acceleration cluster and any number of vector processors may be included in each of PVAs. In at least one embodiment, PVA(s) may include additional error correcting code ("ECC") memory, to enhance overall system safety.

In at least one embodiment, accelerator(s) 1614 (e.g., hardware acceleration cluster) may include a computer vision network on-chip and static random-access memory ("SRAM"), for providing a high-bandwidth, low latency SRAM for accelerator(s) 1614. In at least one embodiment, on-chip memory may include at least 4 MB SRAM, consisting of, for example and without limitation, eight field-configurable memory blocks, that may be accessible by both PVA and DLA. In at least one embodiment, each pair of memory blocks may include an advanced peripheral bus ("APB") interface, configuration circuitry, a controller, and a multiplexer. In at least one embodiment, any type of memory may be used. In at least one embodiment, PVA and DLA may access memory via a backbone that provides PVA and DLA with high-speed access to memory. In at least one embodiment, backbone may include a computer vision network on-chip that interconnects PVA and DLA to memory (e.g., using APB).

In at least one embodiment, computer vision network on-chip may include an interface that determines, before transmission of any control signal/address/data, that both PVA and DLA provide ready and valid signals. In at least one embodiment, an interface may provide for separate phases and separate channels for transmitting control signals/addresses/data, as well as burst-type communications for continuous data transfer. In at least one embodiment, an interface may comply with International Organization for Standardization ("ISO") 26262 or International Electrotechnical Commission ("IEC") 61508 standards, although other standards and protocols may be used.

In at least one embodiment, one or more of SoC(s) 1604 may include a real-time ray-tracing hardware accelerator. In at least one embodiment, real-time ray-tracing hardware accelerator may be used to quickly and efficiently determine positions and extents of objects (e.g., within a world model), to generate real-time visualization simulations, for RADAR signal interpretation, for sound propagation synthesis and/or analysis, for simulation of SONAR systems, for general wave propagation simulation, for comparison to LIDAR data for purposes of localization and/or other functions, and/or for other uses.

In at least one embodiment, accelerator(s) 1614 (e.g., hardware accelerator cluster) have a wide array of uses for autonomous driving. In at least one embodiment, PVA may be a programmable vision accelerator that may be used for key processing stages in ADAS and autonomous vehicles. In at least one embodiment, PVA's capabilities are a good match for algorithmic domains needing predictable processing, at low power and low latency. In other words, PVA performs well on semi-dense or dense regular computation, even on small data sets, which need predictable run-times with low latency and low power. In at least one embodiment, autonomous vehicles, such as vehicle 1600, PVAs are designed to run classic computer vision algorithms, as they are efficient at object detection and operating on integer math.

For example, according to at least one embodiment of technology, PVA is used to perform computer stereo vision. In at least one embodiment, semi-global matching-based algorithm may be used in some examples, although this is not intended to be limiting. In at least one embodiment, applications for Level 3-5 autonomous driving use motion estimation/stereo matching on-the-fly (e.g., structure from motion, pedestrian recognition, lane detection, etc.). In at least one embodiment, PVA may perform computer stereo vision function on inputs from two monocular cameras.

In at least one embodiment, PVA may be used to perform dense optical flow. For example, in at least one embodiment, PVA could process raw RADAR data (e.g., using a 4D Fast Fourier Transform) to provide processed RADAR data. In at least one embodiment, PVA is used for time of flight depth processing, by processing raw time of flight data to provide processed time of flight data, for example.

In at least one embodiment, DLA may be used to run any type of network to enhance control and driving safety, including for example and without limitation, a neural network that outputs a measure of confidence for each object detection. In at least one embodiment, confidence may be represented or interpreted as a probability, or as providing a relative "weight" of each detection compared to other detections. In at least one embodiment, confidence enables a system to make further decisions regarding which detections should be considered as true positive detections rather than false positive detections. For example, In at least one embodiment, a system may set a threshold value for confidence and consider only detections exceeding threshold value as true positive detections. In an embodiment in which an automatic emergency braking ("AEB") system is used, false positive detections would cause vehicle to automatically perform emergency braking, which is obviously undesirable. In at least one embodiment, highly confident detections may be considered as triggers for AEB. In at least one embodiment, DLA may run a neural network for regressing confidence value. In at least one embodiment, neural network may take as its input at least some subset of parameters, such as bounding box dimensions, ground plane estimate obtained (e.g. from another subsystem), output from IMU sensor(s) 1666 that correlates with vehicle 1600 orientation, distance, 3D location estimates of object obtained from neural network and/or other sensors (e.g., LIDAR sensor(s) 1664 or RADAR sensor(s) 1660), among others.

In at least one embodiment, one or more of SoC(s) 1604 may include data store(s) 1616 (e.g., memory). In at least one embodiment, data store(s) 1616 may be on-chip memory of SoC(s) 1604, which may store neural networks to be executed on GPU(s) 1608 and/or DLA. In at least one embodiment, data store(s) 1616 may be large enough in capacity to store multiple instances of neural networks for redundancy and safety. In at least one embodiment, data store(s) 1616 may comprise L2 or L3 cache(s).

In at least one embodiment, one or more of SoC(s) 1604 may include any number of processor(s) 1610 (e.g., embedded processors). In at least one embodiment, processor(s) 1610 may include a boot and power management processor that may be a dedicated processor and subsystem to handle boot power and management functions and related security enforcement. In at least one embodiment, boot and power management processor may be a part of SoC(s) 1604 boot sequence and may provide runtime power management services. In at least one embodiment, boot power and management processor may provide clock and voltage programming, assistance in system low power state transitions, management of SoC(s) 1604 thermals and temperature sensors, and/or management of SoC(s) 1604 power states. In at least one embodiment, each temperature sensor may be implemented as a ring-oscillator whose output frequency is proportional to temperature, and SoC(s) 1604 may use ring-oscillators to detect temperatures of CPU(s) 1606, GPU(s) 1608, and/or accelerator(s) 1614. In at least one embodiment, if temperatures are determined to exceed a threshold, then boot and power management processor may enter a temperature fault routine and put SoC(s) 1604 into a lower power state and/or put vehicle 1600 into a chauffeur to safe stop mode (e.g., bring vehicle 1600 to a safe stop).

In at least one embodiment, processor(s) 1610 may further include a set of embedded processors that may serve as an audio processing engine. In at least one embodiment, audio processing engine may be an audio subsystem that enables full hardware support for multi-channel audio over multiple interfaces, and a broad and flexible range of audio I/O interfaces. In at least one embodiment, audio processing engine is a dedicated processor core with a digital signal processor with dedicated RAM.

In at least one embodiment, processor(s) 1610 may further include an always on processor engine that may provide necessary hardware features to support low power sensor management and wake use cases. In at least one embodiment, always on processor engine may include, without limitation, a processor core, a tightly coupled RAM, supporting peripherals (e.g., timers and interrupt controllers), various I/O controller peripherals, and routing logic.

In at least one embodiment, processor(s) 1610 may further include a safety cluster engine that includes, without limitation, a dedicated processor subsystem to handle safety management for automotive applications. In at least one embodiment, safety cluster engine may include, without limitation, two or more processor cores, a tightly coupled RAM, support peripherals (e.g., timers, an interrupt controller, etc.), and/or routing logic. In a safety mode, two or more cores may operate, in at least one embodiment, in a lockstep mode and function as a single core with comparison logic to detect any differences between their operations. In at least one embodiment, processor(s) 1610 may further include a real-time camera engine that may include, without limitation, a dedicated processor subsystem for handling real-time camera management. In at least one embodiment, processor(s) 1610 may further include a high-dynamic range signal processor that may include, without limitation, an image signal processor that is a hardware engine that is part of camera processing pipeline.

In at least one embodiment, processor(s) 1610 may include a video image compositor that may be a processing block (e.g., implemented on a microprocessor) that implements video post-processing functions needed by a video playback application to produce final image for player window. In at least one embodiment, video image compositor may perform lens distortion correction on wide-view camera(s) 1670, surround camera(s) 1674, and/or on in-cabin monitoring camera sensor(s). In at least one embodiment, in-cabin monitoring camera sensor(s) are preferably monitored by a neural network running on another instance of SoC(s) 1604, configured to identify in cabin events and respond accordingly. In at least one embodiment, an in-cabin system may perform, without limitation, lip reading to activate cellular service and place a phone call, dictate emails, change vehicle's destination, activate or change vehicle's infotainment system and settings, or provide voice-activated web surfing. In at least one embodiment, certain functions are available to driver when vehicle is operating in an autonomous mode and are disabled otherwise.

In at least one embodiment, video image compositor may include enhanced temporal noise reduction for both spatial and temporal noise reduction. For example, in at least one embodiment, where motion occurs in a video, noise reduction weights spatial information appropriately, decreasing weight of information provided by adjacent frames. In at least one embodiment, where an image or portion of an image does not include motion, temporal noise reduction performed by video image compositor may use information from previous image to reduce noise in current image.

In at least one embodiment, video image compositor may also be configured to perform stereo rectification on input stereo lens frames. In at least one embodiment, video image compositor may further be used for user interface composition when operating system desktop is in use, and GPU(s) 1608 are not required to continuously render new surfaces. In at least one embodiment, when GPU(s) 1608 are powered on and active doing 3D rendering, video image compositor may be used to offload GPU(s) 1608 to improve performance and responsiveness.

In at least one embodiment, one or more of SoC(s) 1604 may further include a mobile industry processor interface ("MIPI") camera serial interface for receiving video and input from cameras, a high-speed interface, and/or a video input block that may be used for camera and related pixel input functions. In at least one embodiment, one or more of SoC(s) 1604 may further include an input/output controller(s) that may be controlled by software and may be used for receiving I/O signals that are uncommitted to a specific role.

In at least one embodiment, one or more of SoC(s) 1604 may further include a broad range of peripheral interfaces to enable communication with peripherals, audio encoders/decoders ("codecs"), power management, and/or other devices. SoC(s) 1604 may be used to process data from cameras (e.g., connected over Gigabit Multimedia Serial Link and Ethernet), sensors (e.g., LIDAR sensor(s) 1664, RADAR sensor(s) 1660, etc. that may be connected over Ethernet), data from bus 1602 (e.g., speed of vehicle 1600, steering wheel position, etc.), data from GNSS sensor(s) 1658 (e.g., connected over Ethernet or CAN bus), etc. In at least one embodiment, one or more of SoC(s) 1604 may further include dedicated high-performance mass storage controllers that may include their own DMA engines, and that may be used to free CPU(s) 1606 from routine data management tasks.

In at least one embodiment, SoC(s) 1604 may be an end-to-end platform with a flexible architecture that spans automation levels 3-5, thereby providing a comprehensive functional safety architecture that leverages and makes efficient use of computer vision and ADAS techniques for diversity and redundancy, provides a platform for a flexible, reliable driving software stack, along with deep learning tools. In at least one embodiment, SoC(s) 1604 may be faster, more reliable, and even more energy-efficient and space-efficient than conventional systems. For example, in at least one embodiment, accelerator(s) 1614, when combined with CPU(s) 1606, GPU(s) 1608, and data store(s) 1616, may provide for a fast, efficient platform for level 3-5 autonomous vehicles.

In at least one embodiment, computer vision algorithms may be executed on CPUs, which may be configured using high-level programming language, such as C programming language, to execute a wide variety of processing algorithms across a wide variety of visual data. However, in at least one embodiment, CPUs are oftentimes unable to meet performance requirements of many computer vision applications, such as those related to execution time and power consumption, for example. In at least one embodiment, many CPUs are unable to execute complex object detection algorithms in real-time, which is used in in-vehicle ADAS applications and in practical Level 3-5 autonomous vehicles.

Embodiments described herein allow for multiple neural networks to be performed simultaneously and/or sequentially, and for results to be combined together to enable Level 3-5 autonomous driving functionality. For example, in at least one embodiment, a CNN executing on DLA or discrete GPU (e.g., GPU(s) 1620) may include text and word recognition, allowing supercomputer to read and understand traffic signs, including signs for which neural network has not been specifically trained. In at least one embodiment, DLA may further include a neural network that is able to identify, interpret, and provide semantic understanding of sign, and to pass that semantic understanding to path planning modules running on CPU Complex.

In at least one embodiment, multiple neural networks may be run simultaneously, as for Level 3, 4, or 5 driving. For example, in at least one embodiment, a warning sign consisting of "Caution: flashing lights indicate icy conditions," along with an electric light, may be independently or collectively interpreted by several neural networks. In at least one embodiment, a sign itself may be identified as a traffic sign by a first deployed neural network (e.g., a neural network that has been trained) and a text "flashing lights indicate icy conditions" may be interpreted by a second deployed neural network, which informs vehicle's path planning software (preferably executing on CPU Complex) that when flashing lights are detected, icy conditions exist. In at least one embodiment, a flashing light may be identified by operating a third deployed neural network over multiple frames, informing vehicle's path-planning software of presence (or absence) of flashing lights. In at least one embodiment, all three neural networks may run simultaneously, such as within DLA and/or on GPU(s) 1608.

In at least one embodiment, a CNN for facial recognition and vehicle owner identification may use data from camera sensors to identify presence of an authorized driver and/or owner of vehicle 1600. In at least one embodiment, an always on sensor processing engine may be used to unlock vehicle when owner approaches driver door and turn on lights, and, in security mode, to disable vehicle when owner leaves vehicle. In this way, SoC(s) 1604 provide for security against theft and/or carjacking.

In at least one embodiment, a CNN for emergency vehicle detection and identification may use data from microphones 1696 to detect and identify emergency vehicle sirens. In at least one embodiment, SoC(s) 1604 use CNN for classifying environmental and urban sounds, as well as classifying visual data. In at least one embodiment, CNN running on DLA is trained to identify relative closing speed of emergency vehicle (e.g., by using Doppler effect). In at least one embodiment, CNN may also be trained to identify emergency vehicles specific to local area in which vehicle is operating, as identified by GNSS sensor(s) 1658. In at least one embodiment, when operating in Europe, CNN will seek to detect European sirens, and when in United States CNN will seek to identify only North American sirens. In at least one embodiment, once an emergency vehicle is detected, a control program may be used to execute an emergency vehicle safety routine, slowing vehicle, pulling over to side of road, parking vehicle, and/or idling vehicle, with assistance of ultrasonic sensor(s) 1662, until emergency vehicle(s) passes.

In at least one embodiment, vehicle 1600 may include CPU(s) 1618 (e.g., discrete CPU(s), or dCPU(s)), that may be coupled to SoC(s) 1604 via a high-speed interconnect (e.g., PCIe). In at least one embodiment, CPU(s) 1618 may include an X86 processor, for example. CPU(s) 1618 may be used to perform any of a variety of functions, including arbitrating potentially inconsistent results between ADAS sensors and SoC(s) 1604, and/or monitoring status and health of controller(s) 1636 and/or an infotainment system on a chip ("infotainment SoC") 1630, for example.

In at least one embodiment, vehicle 1600 may include GPU(s) 1620 (e.g., discrete GPU(s), or dGPU(s)), that may be coupled to SoC(s) 1604 via a high-speed interconnect (e.g., NVIDIA's NVLINK). In at least one embodiment, GPU(s) 1620 may provide additional artificial intelligence functionality, such as by executing redundant and/or different neural networks, and may be used to train and/or update neural networks based at least in part on input (e.g., sensor data) from sensors of vehicle 1600.

In at least one embodiment, vehicle 1600 may further include network interface 1624 which may include, without limitation, wireless antenna(s) 1626 (e.g., one or more wireless antennas 1626 for different communication protocols, such as a cellular antenna, a Bluetooth antenna, etc.). In at least one embodiment, network interface 1624 may be used to enable wireless connectivity over Internet with cloud (e.g., with server(s) and/or other network devices), with other vehicles, and/or with computing devices (e.g., client devices of passengers). In at least one embodiment, to communicate with other vehicles, a direct link may be established between vehicle 160 and other vehicle and/or an indirect link may be established (e.g., across networks and over Internet). In at least one embodiment, direct links may be provided using a vehicle-to-vehicle communication link. A vehicle-to-vehicle communication link may provide vehicle 1600 information about vehicles in proximity to vehicle 1600 (e.g., vehicles in front of, on side of, and/or behind vehicle 1600). In at least one embodiment, aforementioned functionality may be part of a cooperative adaptive cruise control functionality of vehicle 1600.

In at least one embodiment, network interface 1624 may include an SoC that provides modulation and demodulation functionality and enables controller(s) 1636 to communicate over wireless networks. In at least one embodiment, network interface 1624 may include a radio frequency front-end for up-conversion from baseband to radio frequency, and down conversion from radio frequency to baseband. In at least one embodiment, frequency conversions may be performed in any technically feasible fashion. For example, frequency conversions could be performed through well-known processes, and/or using super-heterodyne processes. In at least one embodiment, radio frequency front end functionality may be provided by a separate chip. In at least one embodiment, network interface may include wireless functionality for communicating over LTE, WCDMA, UMTS, GSM, CDMA2000, Bluetooth, Bluetooth LE, Wi-Fi, Z-Wave, ZigBee, LoRaWAN, and/or other wireless protocols.

In at least one embodiment, vehicle 1600 may further include data store(s) 1628 which may include, without limitation, off-chip (e.g., off SoC(s) 1604) storage. In at least one embodiment, data store(s) 1628 may include, without limitation, one or more storage elements including RAM, SRAM, dynamic random-access memory ("DRAM"), video random-access memory ("VRAM"), Flash, hard disks, and/or other components and/or devices that may store at least one bit of data.

In at least one embodiment, vehicle 1600 may further include GNSS sensor(s) 1658 (e.g., GPS and/or assisted GPS sensors), to assist in mapping, perception, occupancy grid generation, and/or path planning functions. In at least one embodiment, any number of GNSS sensor(s) 1658 may be used, including, for example and without limitation, a GPS using a USB connector with an Ethernet to Serial (e.g., RS-232) bridge.

In at least one embodiment, vehicle 1600 may further include RADAR sensor(s) 1660. RADAR sensor(s) 1660 may be used by vehicle 1600 for long-range vehicle detection, even in darkness and/or severe weather conditions. In at least one embodiment, RADAR functional safety levels may be ASIL B. RADAR sensor(s) 1660 may use CAN and/or bus 1602 (e.g., to transmit data generated by RADAR sensor(s) 1660) for control and to access object tracking data, with access to Ethernet to access raw data in some examples. In at least one embodiment, wide variety of RADAR sensor types may be used. For example, and without limitation, RADAR sensor(s) 1660 may be suitable for front, rear, and side RADAR use. In at least one embodiment, one or more of RADAR sensors(s) 1660 are Pulse Doppler RADAR sensor(s).

In at least one embodiment, RADAR sensor(s) 1660 may include different configurations, such as long-range with narrow field of view, short-range with wide field of view, short-range side coverage, etc. In at least one embodiment, long-range RADAR may be used for adaptive cruise control functionality. In at least one embodiment, long-range RADAR systems may provide a broad field of view realized by two or more independent scans, such as within a 250 m range. In at least one embodiment, RADAR sensor(s) 1660 may help in distinguishing between static and moving objects, and may be used by ADAS system 1638 for emergency brake assist and forward collision warning. Sensors 1660(*s*) included in a long-range RADAR system may include, without limitation, monostatic multimodal RADAR with multiple (e.g., six or more) fixed RADAR antennae and a high-speed CAN and FlexRay interface. In at least one embodiment, with six antennae, central four antennae may create a focused beam pattern, designed to record vehicle 1600's surroundings at higher speeds with minimal interference from traffic in adjacent lanes. In at least one embodiment, other two antennae may expand field of view, making it possible to quickly detect vehicles entering or leaving vehicle 1600's lane.

In at least one embodiment, mid-range RADAR systems may include, as an example, a range of up to 160 m (front) or 80 m (rear), and a field of view of up to 42 degrees (front) or 150 degrees (rear). In at least one embodiment, short-range RADAR systems may include, without limitation, any number of RADAR sensor(s) 1660 designed to be installed at both ends of rear bumper. When installed at both ends of rear bumper, in at least one embodiment, a RADAR sensor system may create two beams that constantly monitor blind spot in rear and next to vehicle. In at least one embodiment, short-range RADAR systems may be used in ADAS system 1638 for blind spot detection and/or lane change assist.

In at least one embodiment, vehicle 1600 may further include ultrasonic sensor(s) 1662. Ultrasonic sensor(s) 1662, which may be positioned at front, back, and/or sides of vehicle 1600, may be used for park assist and/or to create and update an occupancy grid. In at least one embodiment, a wide variety of ultrasonic sensor(s) 1662 may be used, and different ultrasonic sensor(s) 1662 may be used for different ranges of detection (e.g., 2.5 m, 4 m). In at least one embodiment, ultrasonic sensor(s) 1662 may operate at functional safety levels of ASIL B.

In at least one embodiment, vehicle 1600 may include LIDAR sensor(s) 1664. LIDAR sensor(s) 1664 may be used for object and pedestrian detection, emergency braking, collision avoidance, and/or other functions. In at least one embodiment, LIDAR sensor(s) 1664 may be functional safety level ASIL B. In at least one embodiment, vehicle 1600 may include multiple LIDAR sensors 1664 (e.g., two, four, six, etc.) that may use Ethernet (e.g., to provide data to a Gigabit Ethernet switch).

In at least one embodiment, LIDAR sensor(s) 1664 may be capable of providing a list of objects and their distances for a 360-degree field of view. In at least one embodiment, commercially available LIDAR sensor(s) 1664 may have an advertised range of approximately 100 m, with an accuracy of 2 cm-3 cm, and with support for a 100 Mbps Ethernet connection, for example. In at least one embodiment, one or more non-protruding LIDAR sensors 1664 may be used. In such an embodiment, LIDAR sensor(s) 1664 may be implemented as a small device that may be embedded into front, rear, sides, and/or corners of vehicle 1600. In at least one embodiment, LIDAR sensor(s) 1664, in such an embodiment, may provide up to a 120-degree horizontal and 35-degree vertical field-of-view, with a 200 m range even for low-reflectivity objects. In at least one embodiment, front-mounted LIDAR sensor(s) 1664 may be configured for a horizontal field of view between 45 degrees and 135 degrees.

In at least one embodiment, LIDAR technologies, such as 3D flash LIDAR, may also be used. 3D Flash LIDAR uses a flash of a laser as a transmission source, to illuminate surroundings of vehicle 1600 up to approximately 200 m. In at least one embodiment, a flash LIDAR unit includes, without limitation, a receptor, which records laser pulse transit time and reflected light on each pixel, which in turn corresponds to range from vehicle 1600 to objects. In at least one embodiment, flash LIDAR may allow for highly accurate and distortion-free images of surroundings to be generated with every laser flash. In at least one embodiment, four flash LIDAR sensors may be deployed, one at each side of vehicle 1600. In at least one embodiment, 3D flash LIDAR systems include, without limitation, a solid-state 3D staring array LIDAR camera with no moving parts other than a fan (e.g., a non-scanning LIDAR device). In at least one embodiment, flash LIDAR device(s) may use a 5 nanosecond class I (eye-safe) laser pulse per frame and may capture reflected laser light in form of 3D range point clouds and co-registered intensity data.

In at least one embodiment, vehicle may further include IMU sensor(s) 1666. In at least one embodiment, IMU sensor(s) 1666 may be located at a center of rear axle of vehicle 1600, in at least one embodiment. In at least one embodiment, IMU sensor(s) 1666 may include, for example and without limitation, accelerometer(s), magnetometer(s), gyroscope(s), magnetic compass(es), and/or other sensor types. In at least one embodiment, such as in six-axis applications, IMU sensor(s) 1666 may include, without limitation, accelerometers and gyroscopes. In at least one embodiment, such as in nine-axis applications, IMU sensor(s) 1666 may include, without limitation, accelerometers, gyroscopes, and magnetometers.

In at least one embodiment, IMU sensor(s) 1666 may be implemented as a miniature, high performance GPS-Aided Inertial Navigation System ("GPS/INS") that combines micro-electro-mechanical systems ("MEMS") inertial sensors, a high-sensitivity GPS receiver, and advanced Kalman filtering algorithms to provide estimates of position, velocity, and attitude. In at least one embodiment, IMU sensor(s) 1666 may enable vehicle 1600 to estimate heading without requiring input from a magnetic sensor by directly observing and correlating changes in velocity from GPS to IMU sensor(s) 1666. In at least one embodiment, IMU sensor(s) 1666 and GNSS sensor(s) 1658 may be combined in a single integrated unit.

In at least one embodiment, vehicle 1600 may include microphone(s) 1696 placed in and/or around vehicle 1600. In at least one embodiment, microphone(s) 1696 may be used for emergency vehicle detection and identification, among other things.

In at least one embodiment, vehicle 1600 may further include any number of camera types, including stereo camera(s) 1668, wide-view camera(s) 1670, infrared camera(s) 1672, surround camera(s) 1674, long-range camera(s) 1698, mid-range camera(s) 1676, and/or other camera types. In at least one embodiment, cameras may be used to capture image data around an entire periphery of vehicle 1600. In at least one embodiment, types of cameras used depends on vehicle 1600. In at least one embodiment, any combination of camera types may be used to provide necessary coverage around vehicle 1600. In at least one embodiment, number of cameras may differ depending on embodiment. For example, in at least one embodiment, vehicle 1600 could include six cameras, seven cameras, ten cameras, twelve cameras, or another number of cameras. Cameras may support, as an example and without limitation, Gigabit Multimedia Serial Link ("GMSL") and/or Gigabit Ethernet. In at least one embodiment, each of camera(s) is described with more detail previously herein with respect to FIG. 16A and FIG. 16B.

In at least one embodiment, vehicle 1600 may further include vibration sensor(s) 1642. In at least one embodiment, vibration sensor(s) 1642 may measure vibrations of components of vehicle 1600, such as axle(s). For example, in at least one embodiment, changes in vibrations may indicate a change in road surfaces. In at least one embodiment, when two or more vibration sensors 1642 are used, differences between vibrations may be used to determine friction or slippage of road surface (e.g., when difference in vibration is between a power-driven axle and a freely rotating axle).

In at least one embodiment, vehicle 1600 may include ADAS system 1638. ADAS system 1638 may include, without limitation, an SoC, in some examples. In at least one embodiment, ADAS system 1638 may include, without limitation, any number and combination of an autonomous/adaptive/automatic cruise control ("ACC") system, a cooperative adaptive cruise control ("CACC") system, a forward crash warning ("FCW") system, an automatic emergency braking ("AEB") system, a lane departure warning ("LDW)" system, a lane keep assist ("LKA") system, a blind spot warning ("BSW") system, a rear cross-traffic warning ("RCTW") system, a collision warning ("CW") system, a lane centering ("LC") system, and/or other systems, features, and/or functionality.

In at least one embodiment, ACC system may use RADAR sensor(s) 1660, LIDAR sensor(s) 1664, and/or any number of camera(s). In at least one embodiment, ACC system may include a longitudinal ACC system and/or a lateral ACC system. In at least one embodiment, longitudinal ACC system monitors and controls distance to vehicle immediately ahead of vehicle 1600 and automatically adjust speed of vehicle 1600 to maintain a safe distance from vehicles ahead. In at least one embodiment, lateral ACC system performs distance keeping, and advises vehicle 1600 to change lanes when necessary. In at least one embodiment, lateral ACC is related to other ADAS applications such as LC and CW.

In at least one embodiment, CACC system uses information from other vehicles that may be received via network interface 1624 and/or wireless antenna(s) 1626 from other vehicles via a wireless link, or indirectly, over a network connection (e.g., over Internet). In at least one embodiment, direct links may be provided by a vehicle-to-vehicle ("V2V") communication link, while indirect links may be provided by an infrastructure-to-vehicle ("I2V") communication link. In general, V2V communication concept provides information about immediately preceding vehicles (e.g., vehicles immediately ahead of and in same lane as vehicle 1600), while I2V communication concept provides information about traffic further ahead. In at least one embodiment, CACC system may include either or both I2V and V2V information sources. In at least one embodiment, given information of vehicles ahead of vehicle 1600, CACC system may be more reliable and it has potential to improve traffic flow smoothness and reduce congestion on road.

In at least one embodiment, FCW system is designed to alert driver to a hazard, so that driver may take corrective action. In at least one embodiment, FCW system uses a front-facing camera and/or RADAR sensor(s) 1660, coupled to a dedicated processor, DSP, FPGA, and/or ASIC, that is electrically coupled to driver feedback, such as a display, speaker, and/or vibrating component. In at least one embodiment, FCW system may provide a warning, such as in form of a sound, visual warning, vibration and/or a quick brake pulse.

In at least one embodiment, AEB system detects an impending forward collision with another vehicle or other object, and may automatically apply brakes if driver does not take corrective action within a specified time or distance parameter. In at least one embodiment, AEB system may use front-facing camera(s) and/or RADAR sensor(s) 1660, coupled to a dedicated processor, DSP, FPGA, and/or ASIC. In at least one embodiment, when AEB system detects a hazard, AEB system typically first alerts driver to take corrective action to avoid collision and, if driver does not take corrective action, AEB system may automatically apply brakes in an effort to prevent, or at least mitigate, impact of predicted collision. In at least one embodiment, AEB system, may include techniques such as dynamic brake support and/or crash imminent braking.

In at least one embodiment, LDW system provides visual, audible, and/or tactile warnings, such as steering wheel or seat vibrations, to alert driver when vehicle 1600 crosses lane markings. In at least one embodiment, LDW system does not activate when driver indicates an intentional lane departure, by activating a turn signal. In at least one embodiment, LDW system may use front-side facing cameras, coupled to a dedicated processor, DSP, FPGA, and/or ASIC, that is electrically coupled to driver feedback, such as a display, speaker, and/or vibrating component. In at least one embodiment, LKA system is a variation of LDW system. LKA system provides steering input or braking to correct vehicle 1600 if vehicle 1600 starts to exit lane.

In at least one embodiment, BSW system detects and warns driver of vehicles in an automobile's blind spot. In at least one embodiment, BSW system may provide a visual, audible, and/or tactile alert to indicate that merging or changing lanes is unsafe. In at least one embodiment, BSW system may provide an additional warning when driver uses a turn signal. In at least one embodiment, BSW system may use rear-side facing camera(s) and/or RADAR sensor(s) 1660, coupled to a dedicated processor, DSP, FPGA, and/or ASIC, that is electrically coupled to driver feedback, such as a display, speaker, and/or vibrating component.

In at least one embodiment, RCTW system may provide visual, audible, and/or tactile notification when an object is detected outside rear-camera range when vehicle 1600 is backing up. In at least one embodiment, RCTW system includes AEB system to ensure that vehicle brakes are applied to avoid a crash. In at least one embodiment, RCTW system may use one or more rear-facing RADAR sensor(s) 1660, coupled to a dedicated processor, DSP, FPGA, and/or ASIC, that is electrically coupled to driver feedback, such as a display, speaker, and/or vibrating component.

In at least one embodiment, conventional ADAS systems may be prone to false positive results which may be annoying and distracting to a driver, but typically are not catastrophic, because conventional ADAS systems alert driver and allow driver to decide whether a safety condition truly exists and act accordingly. In at least one embodiment, vehicle 1600 itself decides, in case of conflicting results, whether to heed result from a primary computer or a secondary computer (e.g., first controller 1636 or second controller 1636). For example, in at least one embodiment, ADAS system 1638 may be a backup and/or secondary computer for providing perception information to a backup computer rationality module. In at least one embodiment, backup computer rationality monitor may run a redundant diverse software on hardware components to detect faults in perception and dynamic driving tasks. In at least one embodiment, outputs from ADAS system 1638 may be provided to a supervisory MCU. In at least one embodiment, if outputs from primary computer and secondary computer conflict, supervisory MCU determines how to reconcile conflict to ensure safe operation.

In at least one embodiment, primary computer may be configured to provide supervisory MCU with a confidence score, indicating primary computer's confidence in chosen result. In at least one embodiment, if confidence score exceeds a threshold, supervisory MCU may follow primary computer's direction, regardless of whether secondary computer provides a conflicting or inconsistent result. In at least one embodiment, where confidence score does not meet threshold, and where primary and secondary computer indicate different results (e.g., a conflict), supervisory MCU may arbitrate between computers to determine appropriate outcome.

In at least one embodiment, supervisory MCU may be configured to run a neural network(s) that is trained and configured to determine, based at least in part on outputs from primary computer and secondary computer, conditions under which secondary computer provides false alarms. In at least one embodiment, neural network(s) in supervisory MCU may learn when secondary computer's output may be trusted, and when it cannot. For example, in at least one embodiment, when secondary computer is a RADAR-based FCW system, a neural network(s) in supervisory MCU may learn when FCW system is identifying metallic objects that are not, in fact, hazards, such as a drainage grate or manhole cover that triggers an alarm. In at least one embodiment, when secondary computer is a camera-based LDW system, a neural network in supervisory MCU may learn to override LDW when bicyclists or pedestrians are present and a lane departure is, in fact, safest maneuver. In at least one embodiment, supervisory MCU may include at least one of a DLA or GPU suitable for running neural network(s) with associated memory. In at least one embodiment, supervisory MCU may comprise and/or be included as a component of SoC(s) 1604.

In at least one embodiment, ADAS system 1638 may include a secondary computer that performs ADAS functionality using traditional rules of computer vision. In at least one embodiment, secondary computer may use classic computer vision rules (if-then), and presence of a neural network(s) in supervisory MCU may improve reliability, safety and performance. For example, in at least one embodiment, diverse implementation and intentional non-identity makes overall system more fault-tolerant, especially to faults caused by software (or software-hardware interface) functionality. For example, in at least one embodiment, if there is a software bug or error in software running on primary computer, and non-identical software code running on secondary computer provides same overall result, then supervisory MCU may have greater confidence that overall result is correct, and bug in software or hardware on primary computer is not causing material error.

In at least one embodiment, output of ADAS system 1638 may be fed into primary computer's perception block and/or primary computer's dynamic driving task block. For example, in at least one embodiment, if ADAS system 1638 indicates a forward crash warning due to an object immediately ahead, perception block may use this information when identifying objects. In at least one embodiment, secondary computer may have its own neural network which is trained and thus reduces risk of false positives, as described herein.

In at least one embodiment, vehicle 1600 may further include infotainment SoC 1630 (e.g., an in-vehicle infotainment system (IVI)). Although illustrated and described as an SoC, infotainment system 1630, in at least one embodiment, may not be an SoC, and may include, without limitation, two or more discrete components. In at least one embodiment, infotainment SoC 1630 may include, without limitation, a combination of hardware and software that may be used to provide audio (e.g., music, a personal digital assistant, navigational instructions, news, radio, etc.), video (e.g., TV, movies, streaming, etc.), phone (e.g., hands-free calling), network connectivity (e.g., LTE, WiFi, etc.), and/or information services (e.g., navigation systems, rear-parking assistance, a radio data system, vehicle related information such as fuel level, total distance covered, brake fuel level, oil level, door open/close, air filter information, etc.) to vehicle 1600. For example, infotainment SoC 1630 could include radios, disk players, navigation systems, video players, USB and Bluetooth connectivity, carputers, in-car entertainment, WiFi, steering wheel audio controls, hands free voice control, a heads-up display ("HUD"), HMI display 1634, a telematics device, a control panel (e.g., for controlling and/or interacting with various components, features, and/or systems), and/or other components. In at least one embodiment, infotainment SoC 1630 may further be used to provide information (e.g., visual and/or audible) to user(s) of vehicle, such as information from ADAS system 1638, autonomous driving information such as planned vehicle maneuvers, trajectories, surrounding environment information (e.g., intersection information, vehicle information, road information, etc.), and/or other information.

In at least one embodiment, infotainment SoC 1630 may include any amount and type of GPU functionality. In at least one embodiment, infotainment SoC 1630 may communicate over bus 1602 (e.g., CAN bus, Ethernet, etc.) with other devices, systems, and/or components of vehicle 1600. In at least one embodiment, infotainment SoC 1630 may be coupled to a supervisory MCU such that GPU of infotainment system may perform some self-driving functions in event that primary controller(s) 1636 (e.g., primary and/or backup computers of vehicle 1600) fail. In at least one embodiment, infotainment SoC 1630 may put vehicle 1600 into a chauffeur to safe stop mode, as described herein.

In at least one embodiment, vehicle 1600 may further include instrument cluster 1632 (e.g., a digital dash, an electronic instrument cluster, a digital instrument panel, etc.). In at least one embodiment, instrument cluster 1632 may include, without limitation, a controller and/or supercomputer (e.g., a discrete controller or supercomputer). In at least one embodiment, instrument cluster 1632 may include, without limitation, any number and combination of a set of instrumentation such as a speedometer, fuel level, oil pressure, tachometer, odometer, turn indicators, gearshift position indicator, seat belt warning light(s), parking-brake warning light(s), engine-malfunction light(s), supplemental restraint system (e.g., airbag) information, lighting controls, safety system controls, navigation information, etc. In some examples, information may be displayed and/or shared among infotainment SoC 1630 and instrument cluster 1632. In at least one embodiment, instrument cluster 1632 may be included as part of infotainment SoC 1630, or vice versa.

Inference and/or training logic 715 are used to perform inferencing and/or training operations associated with one or more embodiments. Details regarding inference and/or training logic 715 are provided below in conjunction with FIGS. 7A and/or 7B. In at least one embodiment, inference and/or training logic 715 may be used in system FIG. 16A for inferencing or predicting operations based, at least in part, on weight parameters calculated using neural network training operations, neural network functions and/or architectures, or neural network use cases described herein.

Figure 16B:
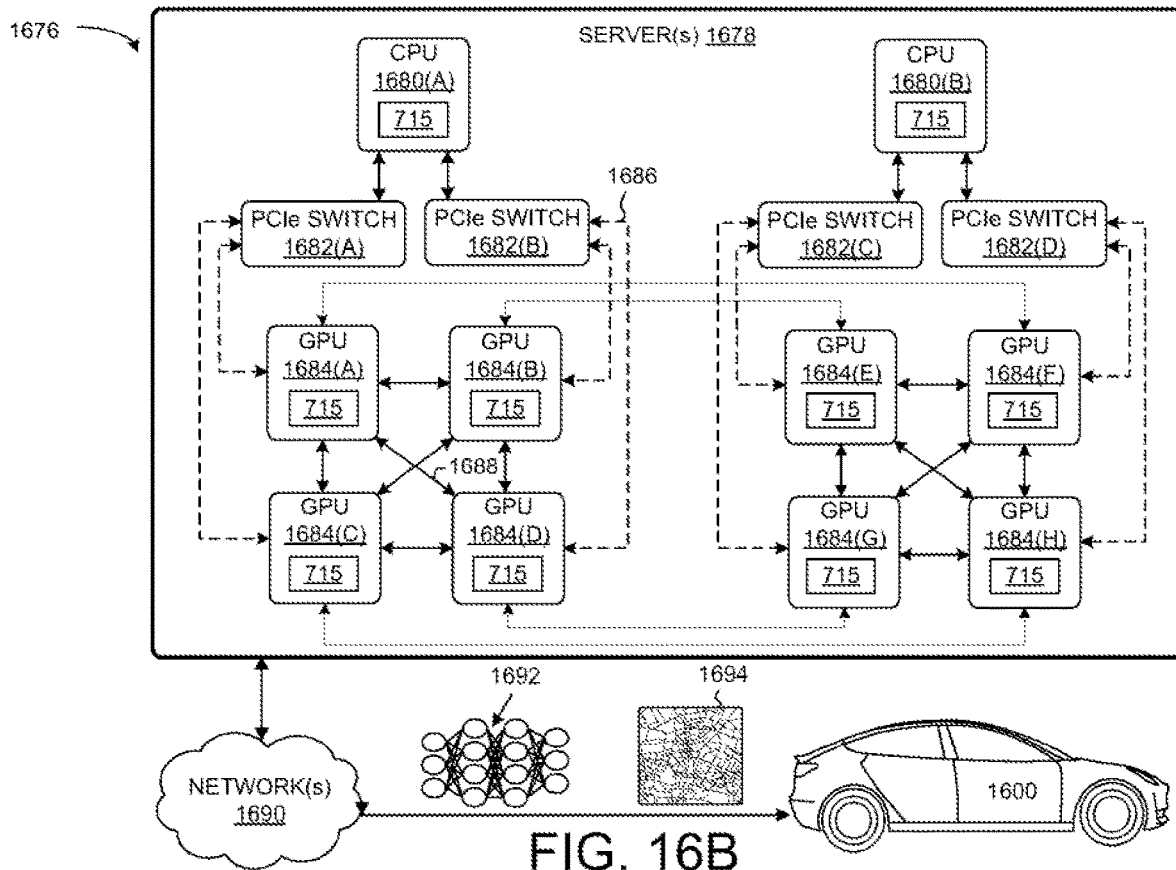

FIG. 16B is a diagram of a system 1676 for communication between cloud-based server(s) and autonomous vehicle 1600 of FIG. 16A, according to at least one embodiment. In at least one embodiment, system 1676 may include, without limitation, server(s) 1678, network(s) 1690, and any number and type of vehicles, including vehicle 1600. In at least one embodiment, server(s) 1678 may include, without limitation, a plurality of GPUs 1684(A)-1684(H) (collectively referred to herein as GPUs 1684), PCIe switches 1682(A)-1682(D) (collectively referred to herein as PCIe switches 1682), and/or CPUs 1680(A)-1680(B) (collectively referred to herein as CPUs 1680). GPUs 1684, CPUs 1680, and PCIe switches 1682 may be interconnected with high-speed interconnects such as, for example and without limitation, NVLink interfaces 1688 developed by NVIDIA and/or PCIe connections 1686. In at least one embodiment, GPUs 1684 are connected via an NVLink and/or NVSwitch SoC and GPUs 1684 and PCIe switches 1682 are connected via PCIe interconnects. In at least one embodiment, although eight GPUs 1684, two CPUs 1680, and four PCIe switches 1682 are illustrated, this is not intended to be limiting. In at least one embodiment, each of server(s) 1678 may include, without limitation, any number of GPUs 1684, CPUs 1680, and/or PCIe switches 1682, in any combination. For example, in at least one embodiment, server(s) 1678 could each include eight, sixteen, thirty-two, and/or more GPUs 1684.

In at least one embodiment, server(s) 1678 may receive, over network(s) 1690 and from vehicles, image data representative of images showing unexpected or changed road conditions, such as recently commenced road-work. In at least one embodiment, server(s) 1678 may transmit, over network(s) 1690 and to vehicles, neural networks 1692, updated neural networks 1692, and/or map information 1694, including, without limitation, information regarding traffic and road conditions. In at least one embodiment, updates to map information 1694 may include, without limitation, updates for HD map 1622, such as information regarding construction sites, potholes, detours, flooding, and/or other obstructions. In at least one embodiment, neural networks 1692, updated neural networks 1692, and/or map information 1694 may have resulted from new training and/or experiences represented in data received from any number of vehicles in environment, and/or based at least in part on training performed at a data center (e.g., using server(s) 1678 and/or other servers).

In at least one embodiment, server(s) 1678 may be used to train machine learning models (e.g., neural networks) based at least in part on training data. In at least one embodiment, training data may be generated by vehicles, and/or may be generated in a simulation (e.g., using a game engine). In at least one embodiment, any amount of training data is tagged (e.g., where associated neural network benefits from supervised learning) and/or undergoes other pre-processing. In at least one embodiment, any amount of training data is not tagged and/or pre-processed (e.g., where associated neural network does not require supervised learning). In at least one embodiment, once machine learning models are trained, machine learning models may be used by vehicles (e.g., transmitted to vehicles over network(s) 1690, and/or machine learning models may be used by server(s) 1678 to remotely monitor vehicles.

In at least one embodiment, server(s) 1678 may receive data from vehicles and apply data to up-to-date real-time neural networks for real-time intelligent inferencing. In at least one embodiment, server(s) 1678 may include deep-learning supercomputers and/or dedicated AI computers powered by GPU(s) 1684, such as a DGX and DGX Station machines developed by NVIDIA. However, in at least one embodiment, server(s) 1678 may include deep learning infrastructure that use CPU-powered data centers.

In at least one embodiment, deep-learning infrastructure of server(s) 1678 may be capable of fast, real-time inferencing, and may use that capability to evaluate and verify health of processors, software, and/or associated hardware in vehicle 1600. For example, in at least one embodiment, deep-learning infrastructure may receive periodic updates from vehicle 1600, such as a sequence of images and/or objects that vehicle 1600 has located in that sequence of images (e.g., via computer vision and/or other machine learning object classification techniques). In at least one embodiment, deep-learning infrastructure may run its own neural network to identify objects and compare them with objects identified by vehicle 1600 and, if results do not match and deep-learning infrastructure concludes that AI in vehicle 1600 is malfunctioning, then server(s) 1678 may transmit a signal to vehicle 1600 instructing a fail-safe computer of vehicle 1600 to assume control, notify passengers, and complete a safe parking maneuver.

In at least one embodiment, server(s) 1678 may include GPU(s) 1684 and one or more programmable inference accelerators (e.g., NVIDIA's TensorRT 3). In at least one embodiment, combination of GPU-powered servers and inference acceleration may make real-time responsiveness possible. In at least one embodiment, such as where performance is less critical, servers powered by CPUs, FPGAs, and other processors may be used for inferencing. In at least one embodiment, inference and/or training logic 715 are used to perform one or more embodiments. Details regarding inference and/or training logic 715 are provided below in conjunction with FIGS. 7A and/or 7B.

Other variations are within spirit of present disclosure. Thus, while disclosed techniques are susceptible to various modifications and alternative constructions, certain illustrated embodiments thereof are shown in drawings and have been described above in detail. It should be understood, however, that there is no intention to limit disclosure to specific form or forms disclosed, but on contrary, intention is to cover all modifications, alternative constructions, and equivalents falling within spirit and scope of disclosure, as defined in appended claims.

Use of terms "a" and "an" and "the" and similar referents in context of describing disclosed embodiments (especially in context of following claims) are to be construed to cover both singular and plural, unless otherwise indicated herein or clearly contradicted by context, and not as a definition of a term. Terms "comprising," "having," "including," and "containing" are to be construed as open-ended terms (meaning "including, but not limited to,") unless otherwise noted. Term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within range, unless otherwise indicated herein and each separate value is incorporated into specification as if it were individually recited herein. Use of term "set" (e.g., "a set of items") or "subset," unless otherwise noted or contradicted by context, is to be construed as a nonempty collection comprising one or more members. Further, unless otherwise noted or contradicted by context, term "subset" of a corresponding set does not necessarily denote a proper subset of corresponding set, but subset and corresponding set may be equal.

Conjunctive language, such as phrases of form "at least one of A, B, and C," or "at least one of A, B and C," unless specifically stated otherwise or otherwise clearly contradicted by context, is otherwise understood with context as used in general to present that an item, term, etc., may be either A or B or C, or any nonempty subset of set of A and B and C. For instance, in illustrative example of a set having three members, conjunctive phrases "at least one of A, B, and C" and "at least one of A, B and C" refer to any of following sets: {A}, {B}, {C}, {A, B}, {A, C}, {B, C}, {A, B, C}. Thus, such conjunctive language is not generally intended to imply that certain embodiments require at least one of A, at least one of B, and at least one of C each to be present. In addition, unless otherwise noted or contradicted by context, term "plurality" indicates a state of being plural (e.g., "a plurality of items" indicates multiple items). A plurality is at least two items, but can be more when so indicated either explicitly or by context. Further, unless stated otherwise or otherwise clear from context, phrase "based on" means "based at least in part on" and not "based solely on."

Operations of processes described herein can be performed in any suitable order unless otherwise indicated herein or otherwise clearly contradicted by context. In at least one embodiment, a process such as those processes described herein (or variations and/or combinations thereof) is performed under control of one or more computer systems configured with executable instructions and is implemented as code (e.g., executable instructions, one or more computer programs or one or more applications) executing collectively on one or more processors, by hardware or combinations thereof. In at least one embodiment, code is stored on a computer-readable storage medium, for example, in form of a computer program comprising a plurality of instructions executable by one or more processors. In at least one embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In at least one embodiment, code (e.g., executable code or source code) is stored on a set of one or more non-transitory computer-readable storage media having stored thereon executable instructions (or other memory to store executable instructions) that, when executed (i.e., as a result of being executed) by one or more processors of a computer system, cause computer system to perform operations described herein. A set of non-transitory computer-readable storage media, in at least one embodiment, comprises multiple non-transitory computer-readable storage media and one or more of individual non-transitory storage media of multiple non-transitory computer-readable storage media lack all of code while multiple non-transitory computer-readable storage media collectively store all of code. In at least one embodiment, executable instructions are executed such that different instructions are executed by different processors— for example, a non-transitory computer-readable storage medium store instructions and a main central processing unit ("CPU") executes some of instructions while a graphics processing unit ("GPU") executes other instructions. In at least one embodiment, different components of a computer system have separate processors and different processors execute different subsets of instructions.

Accordingly, in at least one embodiment, computer systems are configured to implement one or more services that singly or collectively perform operations of processes described herein and such computer systems are configured with applicable hardware and/or software that enable performance of operations. Further, a computer system that implements at least one embodiment of present disclosure is a single device and, in another embodiment, is a distributed computer system comprising multiple devices that operate differently such that distributed computer system performs operations described herein and such that a single device does not perform all operations.

Use of any and all examples, or exemplary language (e.g., "such as") provided herein, is intended merely to better illuminate embodiments of disclosure and does not pose a limitation on scope of disclosure unless otherwise claimed. No language in specification should be construed as indicating any non-claimed element as essential to practice of disclosure.

All references, including publications, patent applications, and patents, cited herein are hereby incorporated by reference to same extent as if each reference were individually and specifically indicated to be incorporated by reference and were set forth in its entirety herein.

In description and claims, terms "coupled" and "connected," along with their derivatives, may be used. It should be understood that these terms may be not intended as synonyms for each other. Rather, in particular examples, "connected" or "coupled" may be used to indicate that two or more elements are in direct or indirect physical or electrical contact with each other. "Coupled" may also mean that two or more elements are not in direct contact with each other, but yet still co-operate or interact with each other.

Unless specifically stated otherwise, it may be appreciated that throughout specification terms such as "processing," "computing," "calculating," "determining," or like, refer to action and/or processes of a computer or computing system, or similar electronic computing device, that manipulate and/or transform data represented as physical, such as electronic, quantities within computing system's registers and/or memories into other data similarly represented as physical quantities within computing system's memories, registers or other such information storage, transmission or display devices.

In a similar manner, term "processor" may refer to any device or portion of a device that processes electronic data from registers and/or memory and transform that electronic data into other electronic data that may be stored in registers and/or memory. As non-limiting examples, "processor" may be a CPU or a GPU. A "computing platform" may comprise one or more processors. As used herein, "software" processes may include, for example, software and/or hardware entities that perform work over time, such as tasks, threads, and intelligent agents. Also, each process may refer to multiple processes, for carrying out instructions in sequence or in parallel, continuously or intermittently. Terms "system" and "method" are used herein interchangeably insofar as system may embody one or more methods and methods may be considered a system.

In present document, references may be made to obtaining, acquiring, receiving, or inputting analog or digital data into a subsystem, computer system, or computer-implemented machine. Obtaining, acquiring, receiving, or inputting analog and digital data can be accomplished in a variety of ways such as by receiving data as a parameter of a function call or a call to an application programming interface. In some implementations, process of obtaining, acquiring, receiving, or inputting analog or digital data can be accomplished by transferring data via a serial or parallel interface. In another implementation, process of obtaining, acquiring, receiving, or inputting analog or digital data can be accomplished by transferring data via a computer network from providing entity to acquiring entity. References may also be made to providing, outputting, transmitting, sending, or presenting analog or digital data. In various examples, process of providing, outputting, transmitting, sending, or presenting analog or digital data can be accomplished by transferring data as an input or output parameter of a function call, a parameter of an application programming interface or inter-process communication mechanism.

Although discussion above sets forth example implementations of described techniques, other architectures may be used to implement described functionality, and are intended to be within scope of this disclosure. Furthermore, although specific distributions of responsibilities are defined above for purposes of discussion, various functions and responsibilities might be distributed and divided in different ways, depending on circumstances.

Furthermore, although subject matter has been described in language specific to structural features and/or methodological acts, it is to be understood that subject matter claimed in appended claims is not necessarily limited to specific features or acts described. Rather, specific features and acts are disclosed as exemplary forms of implementing the claims.

What is claimed is:

1. A computer-implemented method, comprising:
receiving image data including a representation of a face of a person over a period of time;
determining, from at least a portion of the image data, a set of blink parameters for the person;
determining context data for a time at which the image data was generated, the context data relating to one or more environmental conditions associated with a vehicle operated by the person;
determining an action context based, at least in part, on the context data;
selecting a baseline for the action context;
passing the set of blink parameters and the action context to at least a first neural network to generate at least a first drowsiness prediction for the person relative to the baseline, wherein the action context is utilized to account for variations in the set of blink parameters due to the one or more environmental conditions;
passing a blink frequency determination to at least a second neural network to generate at least a second drowsiness prediction;

determining an overall drowsiness prediction based, at least, on the first drowsiness prediction and the second drowsiness prediction;

determining the overall drowsiness prediction exceeds a threshold; and activating a driver assistance protocol for the vehicle.

2. The computer-implemented method of claim 1, wherein the one or more environmental conditions relate to at least one of a road configuration, brightness, weather, time of day, location, speed, or number of surrounding objects.

3. The computer-implemented method of claim 1, further comprising:

determining the one or more environmental conditions using data from one or more cameras, sensors, global positioning system (GPS) signals, or network data sources.

4. The computer-implemented method of claim 1, further comprising:

determining a blink scenario based at least in part upon the one or more environmental conditions; and determining the first drowsiness prediction using one or more blink thresholds corresponding to the blink scenario.

5. The computer-implemented method of claim 1, further comprising:

determining, using the image, an identity of the person;

identifying a blink profile for the person including one or more blink behaviors specific to the person; and generating at least the first drowsiness prediction based further upon data for the one or more blink behaviors.

6. The computer-implemented method of claim 1, further comprising:

identifying a set of facial landmarks in the image data;

determining, from the image data, eye state information indicating whether the eyes of the person are fully or partially open or closed;

determining, from the image data, head pose information for the person;

determining, based at least in part upon the set of facial landmarks, the head pose information, and the eye state information, the set of blink parameters; and determining, from the eye state information, the blink frequency information for the recent period of time.

7. The computer-implemented method of claim 6, wherein the first neural network and the second neural network are long short term memory (LSTM) networks, and wherein the first drowsiness prediction and the second drowsiness prediction generated by the LSTM networks correspond to Karolinska Sleepiness Scale (KSS) values.

8. The computer-implemented method of claim 6, wherein at least a subset of the set of blink parameters are determined using aspect ratio information calculated from the set of facial landmarks.

9. The computer-implemented method of claim 1, wherein the context data is provided as input to the first neural network as one or more feature vectors determined from the context data.

10. A system, comprising:

a camera to capture image data including a representation of a face of a person over a period of time;

one or more processors; and memory including instructions that, when executed by the one or more processors, cause the system to:

determine, from at least a portion of the image data, a set of blink parameters for the person;

determine context data for a time at which the image data was captured, the context data relating to one or more environmental conditions associated with a vehicle operated by the person;

determine an action context based, at least in part, on the context data;

select a baseline for the action context;

generate, using the set of blink parameters and the action context with at least a first neural network, at least a first drowsiness prediction for the person relative to the baseline, wherein the action context is utilized to account for variations in the set of blink parameters due to the one or more environmental conditions;

generate, using blink frequency information with at least a second neural network, a second drowsiness prediction for the person;

determine an overall drowsiness prediction based, at least, on the first drowsiness prediction and the second drowsiness prediction;

determine the overall drowsiness prediction exceeds a threshold; and activate a driver assistance protocol for the vehicle.

11. The system of claim 10, wherein the instructions if performed by the one or more processors further cause the system to:

determine the one or more environmental conditions using data from one or more cameras, sensors, global positioning system (GPS) signals, or network data sources, wherein the one or more environmental conditions relate to at least one of a road configuration, brightness, weather, time of day, location, speed, or number of surrounding objects.

12. The system of claim 10, wherein the instructions if performed by the one or more processors further cause the system to:

determine a blink scenario based at least in part upon the one or more environmental conditions; and determine the first drowsiness prediction using one or more blink thresholds corresponding to the blink scenario.

13. The system of claim 10, wherein the instructions if performed by the one or more processors further cause the system to:

determine, using the image, an identity of the person;

identify a blink profile for the person including one or more blink behaviors specific to the person; and generate at least the first drowsiness prediction based further upon data for the one or more blink behaviors.

14. The system of claim 10, wherein the instructions if performed by the one or more processors further cause the system to:

identify a set of facial landmarks in the image data;

determine, from the image data, eye state information indicating whether the eyes of the person are fully or partially open or closed;

determine, from the image data, head pose information for the person;

determine, based at least in part upon the set of facial landmarks, the head pose information, and the eye state information, the set of blink parameters;

determine, from the eye state information, the blink frequency information for the recent period of time.

15. The system of claim 14, wherein the first neural network and the second neural network are long short term memory (LSTM) networks, and wherein the first drowsiness prediction and the second drowsiness prediction generated by the LSTM networks correspond to Karolinska Sleepiness Scale (KSS) values.

16. The system of claim 10, wherein the system comprises at least one of:
- a system for performing simulation operations;
- a system for performing simulation operations to test or validate autonomous machine applications;
- a system for rendering graphical output;
- a system for performing deep learning operations;
- a system implemented using an edge device;
- a system incorporating one or more Virtual Machines (VMs);
- a system implemented at least partially in a data center; or
- a system implemented at least partially using cloud computing resources.

17. A non-transitory computer-readable storage medium including instructions that, when executed by one or more processors, cause the one or more processors to:
- obtain image data including a representation of a face of a person;
- determine, from at least a portion of the image data, a set of blink parameters for the person;
- determine context data for a time at which the image data was captured, the context data relating to one or more environmental conditions associated with a vehicle operated by the person;
- determine an action context based, at least in part, on the context data;
- select a baseline for the action context;
- generate, using the set of blink parameters and the action context with at least a first neural network, at least a first drowsiness prediction for the person relative to the baseline, wherein the action context is utilized to account for variations in the set of blink parameters due to the one or more environmental conditions;
- generate, using blink frequency information with at least a second neural network, a second drowsiness prediction for the person;
- determine an overall drowsiness prediction based, at least, on the first drowsiness prediction and the second drowsiness prediction;
- determine the overall drowsiness prediction exceeds a threshold; and
- activate a driver assistance protocol for the vehicle.

18. The non-transitory computer-readable storage medium of claim 17, wherein the instructions when performed further cause the one or more processors to:
- determine the one or more environmental conditions using data from one or more cameras, sensors, global positioning system (GPS) signals, or network data sources, wherein the one or more environmental conditions relate to at least one of a road configuration, brightness, weather, time of day, location, speed, or number of surrounding objects.

19. The non-transitory computer-readable storage medium of claim 17, wherein the instructions when performed further cause the one or more processors to:
- determine, using the image, an identity of the person;
- identify a blink profile for the person including one or more blink behaviors specific to the person; and
- generate at least the first drowsiness prediction based further upon data for the one or more blink behaviors.

20. The non-transitory computer-readable storage medium of claim 17, wherein the instructions when performed further cause the one or more processors to:
- identify a set of facial landmarks in the image data;
- determine, from the image data, eye state information indicating whether the eyes of the person are fully or partially open or closed;
- determine, from the image data, head pose information for the person;
- determine, based at least in part upon the set of facial landmarks, the head pose information, and the eye state information, the set of blink parameters;
- determine, from the eye state information, the blink frequency information for the recent period of time.

* * * * *